US011890297B2

(12) United States Patent
Xu et al.

(10) Patent No.: US 11,890,297 B2
(45) Date of Patent: Feb. 6, 2024

(54) COMBINATION THERAPY FOR HIV WITH ADENOSINE DERIVATIVE AND CAPSID INHIBITORS

(71) Applicant: Brii Biosciences, Inc., Durham, NC (US)

(72) Inventors: Lianhong Xu, Durham, NC (US); Zhi Hong, Durham, NC (US)

(73) Assignee: Brii Biosciences, Inc., Durham, NC (US)

( * ) Notice: Subject to any disclaimer, the term of this patent is extended or adjusted under 35 U.S.C. 154(b) by 0 days.

(21) Appl. No.: 17/583,815

(22) Filed: Jan. 25, 2022

(65) Prior Publication Data
US 2022/0249532 A1  Aug. 11, 2022

Related U.S. Application Data

(60) Provisional application No. 63/141,445, filed on Jan. 25, 2021.

(51) Int. Cl.
| | | |
|---|---|---|
| A61K 31/70 | (2006.01) | |
| A01N 43/04 | (2006.01) | |
| A61K 31/7076 | (2006.01) | |
| A61K 45/06 | (2006.01) | |
| A61P 31/18 | (2006.01) | |

(52) U.S. Cl.
CPC .......... *A61K 31/7076* (2013.01); *A61K 45/06* (2013.01); *A61P 31/18* (2018.01)

(58) Field of Classification Search
None
See application file for complete search history.

(56) References Cited

U.S. PATENT DOCUMENTS

| | | | |
|---|---|---|---|
| 7,339,053 B2 | 3/2008 | Kohgo et al. | |
| 7,625,877 B2 | 12/2009 | Kohgo et al. | |
| 8,039,614 B2 | 10/2011 | Kohgo et al. | |
| 10,071,985 B2 * | 9/2018 | Graupe | C07F 5/025 |
| 10,752,636 B2 | 8/2020 | Bacon et al. | |
| 2018/0002366 A1 | 1/2018 | Girijavallabhan et al. | |
| 2022/0288098 A1 | 9/2022 | Xu | |

FOREIGN PATENT DOCUMENTS

| | | |
|---|---|---|
| WO | WO-2005025583 A2 | 3/2005 |
| WO | WO-2007022073 A2 | 2/2007 |
| WO | WO-2017053216 A2 | 3/2017 |
| WO | WO-2018035359 A1 | 2/2018 |
| WO | WO-2018145021 A1 | 8/2018 |
| WO | WO-2019035904 A1 | 2/2019 |
| WO | WO-2020044257 A1 | 3/2020 |
| WO | WO-2020178767 A1 | 9/2020 |
| WO | WO-2021021717 A1 | 2/2021 |
| WO | WO-2022159877 A1 | 7/2022 |

OTHER PUBLICATIONS

Markowitz, Martin, and Stefan G. Sarafianos. "EFdA (4'-ethynyl-2-fluoro-2'-deoxyadenosine, MK-8591): a novel HIV-1 reverse transcriptase translocation inhibitor." Current Opinion in HIV and AIDS 13.4 (2018): 294.*
Solyev, Pavel N., et al. "Synthesis and anti-HIV properties of new carbamate prodrugs of AZT." Chemical Biology & Drug Design 80.6 (2012): 947-952.*
Hayakawa et al., "Potential of 4'-C-substituted nucleosides for the treatment of HIV-1," Antiviral Chemistry & Chemotherapy, 15: 169-187, Aug. 2004.
International Search Report and Written Opinion for International Application No. PCT/US2022/013669 dated May 23, 2022, 12 pages.
Invitation to Pay for International Application No. PCT/US2022/013669 dated Mar. 28, 2022, 3 pages.
Iyidogan et al., "Current Perspectives on HIV-1 Antiretroviral Drug Resistance," Viruses, Oct. 2014, 6, pp. 4095-4139.
Ohrui et al., "Syntheses of 4'-C-Ethynyl-β-D-arabino-and 4'-C-Ethynyl-2'-deoxy-β-D-ribo-pentofuranosylpyrimidines and -purines and Evaluation of Their Anti-HIV Activity," Journal of Medicinal Chemistry, Nov. 2000, 43, pp. 4516-4525.
Pauwels, Rudi, "Aspects of successful drug discovery and development", Antiviral Research 71(2-3), Sep. 2006, pp. 77-89.
Singh et al., "Long-Acting Anti-HIV Drugs Targeting HIV-1 Reverse Transcriptase and Integrase," Pharmaceuticals, 12, 62, Jun. 2019, 14 pages.
PCT Third Party Observation issued in International Application No. PCT/US2022/013669 dated May 25, 2023, 2 pages.
Non-Final Office Action issued in U.S. Appl. No. 18/176,204 dated May 9, 2023, 19 pages.
Response to Non-Final Action issued in U.S. Appl. No. 18/176,204, filed Aug. 8, 2023, 15 pages.
Extended European Search Report for European Application No. EP20848596.1 dated Sep. 15, 2023, 9 pages.
International Preliminary Report on Patentability for International Application No. PCT/US2022/013669 dated Aug. 3, 2023, 8 pages.
Kageyama et al., "Enantioselective total synthesis of the potent anti-HIV nucleoside EFdA". Organic Letters. Oct. 7, 2011; 13(19): 5264-6.

* cited by examiner

*Primary Examiner* — Patrick T Lewis
(74) *Attorney, Agent, or Firm* — COOLEY LLP

(57) ABSTRACT

The present disclosure is directed to methods of treating or preventing RNA virus infections and retroviral diseases, such as HIV and AIDS, comprising administering to a subject in need an effective amount of (a) a capsid inhibitor and (b) an adenosine derivative disclosed herein. Compositions comprising an effective amount of an adenosine derivative and an effective amount of a capsid (CA) inhibitor are also provided.

41 Claims, 1 Drawing Sheet

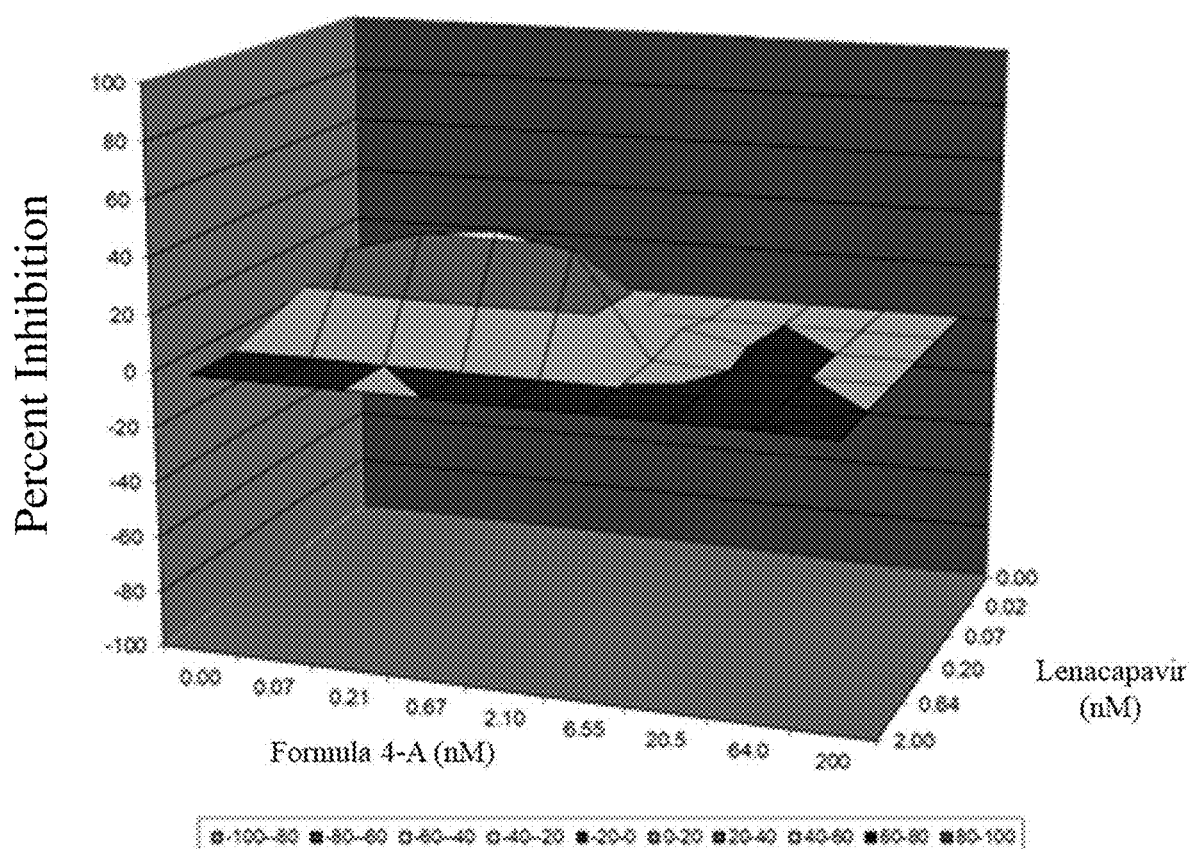

COMBINATION THERAPY FOR HIV WITH ADENOSINE DERIVATIVE AND CAPSID INHIBITORS

CROSS REFERENCE TO RELATED APPLICATIONS

This application claims the benefit of and priority to U.S. Provisional Application Ser. No. 63/141,445, filed Jan. 25, 2021, which is herein incorporated by reference in its entirety.

FIELD

This disclosure is directed to adenosine derivative prodrugs that can inhibit reverse transcriptase. This disclosure is also directed to pharmaceutical compositions comprising an adenosine derivative prodrug and a capsid inhibitor that can be used for the treatment or prevention of acquired immunodeficiency syndrome (AIDS), HIV-1, HIV-2, multidrug resistant HIV or a combination thereof.

BACKGROUND

Retroviruses such as human immunodeficiency virus (HIV) have been linked to the immunosuppressive disease known as acquired immunodeficiency syndrome (AIDS). Multiple strains of retrovirus, such as HIV type-1 (HIV-1) and type-2 (HIV-2) are known to be related to the diseases. The HIV retrovirus infected individuals can be initially asymptomatic, but then develop AIDS related complex (ARC) followed by AIDS. Replication of HIV by a host cell requires integration of the viral genome into the DNA of host cells. A key step in the process involves transcription of the viral RNA genome into DNA via an enzyme known as reverse transcriptase (RT).

A reverse transcriptase typically can have multiple enzymatic functions that can act (1) as an RNA-dependent DNA polymerase transcribing a single-stranded DNA copy of the viral RNA (first DNA), (2) as a ribonuclease destroying the original viral RNA and frees the DNA just produced from the original RNA, and (3) as a DNA-dependent DNA polymerase producing a second, complementary DNA strand using the first DNA strand as a template. The two DNA strands then form double-stranded DNA, which is integrated into the genome of the host cells by an integrase enzyme.

A number of compounds can inhibit reverse transcriptase (RT) activity. These compounds can be useful for the treatment of HIV infection in humans by inhibiting HIV replication in infected cells or individuals. Examples of the compounds approved for use in treating HIV infection and AIDS include nucleoside RT inhibitors (NRTI) such as 3'-azido-3'-deoxythymidine (AZT, also known as Zidovudine (ZDV), azidothymidine (AZT)), 2',3'-dideoxyinosine (ddI), 2',3'-dideoxycytidine (ddC), d4T, 3TC, abacavir, emtricitabine, and tenofovir disoproxil fumarate, as well as non-nucleoside RT inhibitors (NNRTI) such as nevirapine, delavirdine, efavirenz, rilpivirine and doravirine (DHHS guidelines: https://aidsinfo.nih.gov/understanding-hiv-aids, Iyidogan & Anderson, Viruses, 6, 4095-4139, 2014, doi: 10.3390/v6104095; Hayakawa et al., Antiviral Chem & Chemotherapy, 15:169-187, 2004; Ohrui et al., J. Med. Chem. 43, 4516-4525, 2000; Pauwels, Antiviral Research, 71, 77-89, 2006.).

An adenosine derivative EFdA (4'-ethynyl-2-fluoro-2'-deoxyadenosine, also known as MK-8591, islatravir) is a long-acting (LA) NRTI that has been demonstrated to have anti-HIV activity via inhibiting reverse transcriptase by preventing translocation (U.S. Pat. Nos. 7,339,053, 7,625,877, 8,039,614. Singh et al., Pharmaceuticals, 12, 62, 2019, DOI: 10.3390/ph12020062, each of which is incorporated by reference herein in its entirety). This compound has broad inhibitory activity and potency for different subtypes and mutations including HIV-1, HIV-2, and multidrug resistant (MDR) and wildtype (WT) strains, and reverse transcriptase inhibitor (RTI) resistant viruses. Some modified EFdA analogs and prodrugs have been described in U.S. Patent Publication No.: 2018/0002366, incorporated by reference herein in its entirety.

A common issue that arises from the treatment of HIV infection with anti-retroviral inhibitory compounds is resistance of the viruses to the inhibitors. Such resistance is typically the result of mutations that occur in the reverse transcriptase segment of the pol gene. The continued use of antiviral compounds, such as the inhibitory compounds, to prevent HIV infection will inevitably result in the emergence of new resistant strains of HIV. Therefore, there is a continuing need for new RT inhibitors that are effective against HIV strains including mutant HIV and multidrug-resistant HIV strains.

Another common issue is the medication adherence. Medication adherence is essential for individuals with HIV to have successful therapy over a lifetime. Adherence to a daily regimen can be challenging, which also has negative impact on the patient's quality of life with daily reminders of their HIV status. Increasing patient adherence to a drug regimen can potentially be achieved through reducing the dosing frequency. Therefore, there is a need to identify long-acting compounds or regimens (for example, once a week, once a month or once every two-month therapy) for patients to overcome these challenges tied to taking daily, oral medication.

SUMMARY

The present disclosure, which addresses these and other problems, is related to adenosine derivatives and compositions thereof that can be used to treat retroviral diseases such as HIV and AIDS and RNA virus infections.

In some embodiments, the present disclosure provides compositions comprising an effective dosage of:
(a) a capsid (CA) inhibitor; and
(b) an adenosine derivative or pharmaceutically acceptable salt, tautomer, or solvate thereof,
wherein the adenosine derivative is a compound having a structure of formula (1):

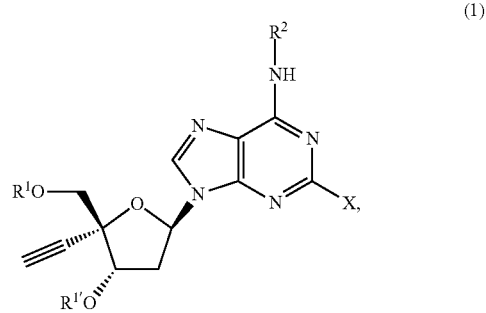

or a pharmaceutically acceptable salt, tautomer, or solvate thereof, wherein:

R¹, R¹', and R² each is independently H, —C(O)N(R³)(R³'), —C(O)OR⁴, —R⁵, -L¹-R⁵, or —Z-L⁴-R⁵, provided that at least one of R¹ and R² is not H;

R³, R³' and R⁴ each is independently H, C1-C10 alkyl, C2-C10 alkenyl, C3-C10 cycloalkyl, 3- to 10-membered heterocycloalkyl, aryl, or heteroaryl;

R⁵ is:

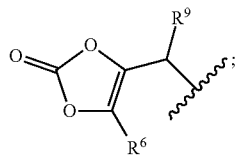

R⁶ is H, C1-C10 alkyl, C2-C10 alkenyl, C3-C10 cycloalkyl, 3- to 10-membered heterocycloalkyl, aryl, or heteroaryl;

L¹-R⁵ is —(C1-C10 alkylene)-N(R⁷)—R⁵, —(C1-C10 alkylene)-O—R⁵, —(C1-C10 alkylene)-S—R⁵, —(C2-C10 alkenylene)-N(R⁷)—R⁵, —(C2-C10 alkenylene)-O—R⁵, —(C2-C10 alkenylene)-S—R⁵, —C(O)O—R⁵, —C(O)O-L²-N(R⁷)—R⁵, —C(O)O-L²-O—R⁵, —C(O)O-L²-S—R⁵, —C(O)O-L²-C(O)O—R⁵, —C(O)O-L²-C(O)N(R⁷)—R⁵, —C(O)O-L²-C(O)N(R⁷)-L³-N(R⁷)—R⁵, —C(O)O-L²-C(O)N(R⁷)-L³-O—R⁵, —C(O)O-L²-C(O)N(R⁷)-L³-S—R⁵, —C(O)N(R⁷)—R⁵, —C(O)N(R⁷)-L²-N(R⁷)—R⁵, —C(O)N(R⁷)-L²-O—R⁵, —C(O)N(R⁷)-L²-S—R⁵, —C(O)N(R⁷)-L²-C(O)O—R⁵, —C(O)N(R⁷)-L²-C(O)N(R⁸)—R⁵—, —C(O)N(R⁷)-L²-C(O)N(R⁸)-L³-N(R⁷)—R⁵, —C(O)O-L²-N(R⁷)C(O)O—R⁵, —C(O)N(R⁸)-L²-N(R⁷)C(O)O—R⁵, —C(O)O-L²-N(R⁷)C(O)N(R⁸)—R⁵, —C(O)N(R⁷)-L²-N(R⁷)C(O)N(R⁸)—R⁵, —C(O)N(R⁷)-L²-C(O)N(R⁸)-L³-O—R⁵ or —C(O)N(R⁷)-L²-C(O)N(R⁸)-L³-S—R⁵;

—Z— is —C(O)—, —C(O)O—, or —C(O)N(R⁷)—;

L⁴-R⁵ is —(C1-C10 alkylene)-N(R⁷)—R⁵, —(C1-C10 alkylene)-O—R⁵, —(C1-C10 alkyl)-S—R⁵, —(C2-C10 alkenylene)-N(R⁷)—R⁵, —(C2-C10 alkenylene)-O—R⁵ or —(C2-C10 alkenylene)-S—R⁵;

R⁷ and R⁸ each is independently H, C1-C10 alkyl, or C2-C10 alkenyl;

R⁹ is independently H, —F, C1-C10 alkyl, or C2-C10 alkenyl;

L² and L³ each is —(C1-C10 alkylene)-, or —(C2-C10 alkenylene)-; and

X is a halogen atom.

In some embodiments, the compositions further comprise a pharmaceutically acceptable carrier.

In some embodiments, the present disclosure provides methods of treating or preventing an HIV infection, comprising administering to a subject in need thereof an effective amount of:

(a) a capsid (CA) inhibitor; and (b) an adenosine derivative or pharmaceutically acceptable salt, tautomer, or solvate thereof, wherein the adenosine derivative is a compound of formula (1) having the structure:

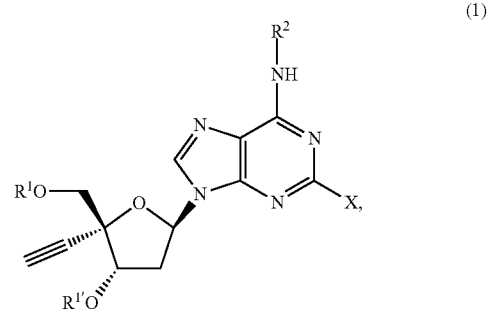

or a pharmaceutically acceptable salt, tautomer, or solvate thereof, wherein:

R¹, R1', and R² each is independently H, —C(O)N(R³)(R³'), —C(O)OR⁴, —R⁵, -L¹-R⁵, or —Z-L⁴-R⁵, provided that at least one of R¹ and R² is not H;

R³, R³' and R⁴ each is independently H, C1-C10 alkyl, C2-C10 alkenyl, C3-C10 cycloalkyl, 3- to 10-membered heterocycloalkyl, aryl, or heteroaryl;

R⁵ is:

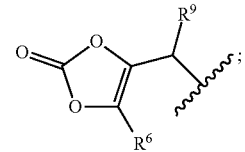

R⁶ is H, C1-C10 alkyl, C2-C10 alkenyl, C3-C10 cycloalkyl, 3- to 10-membered heterocycloalkyl, aryl, or heteroaryl;

-L¹-R⁵ is —(C1-C10 alkylene)-N(R⁷)—R⁵, —(C1-C10 alkylene)-O—R⁵, —(C1-C10 alkylene)-S—R⁵, —(C2-C10 alkenylene)-N(R⁷)—R⁵, —(C2-C10 alkenylene)-O—R⁵, —(C2-C10 alkenylene)-S—R⁵, —C(O)O—R⁵, —C(O)O-L²-N(R⁷)—R⁵, —C(O)O-L²-O—R⁵, —C(O)O-L²-S—R⁵, —C(O)O-L²-C(O)O—R⁵, —C(O)O-L²-C(O)N(R⁷)—R⁵, —C(O)O-L²-C(O)N(R⁷)-L³-N(R⁷)—R⁵, —C(O)O-L²-C(O)N(R⁷)-L³-O—R⁵, —C(O)O-L²-C(O)N(R⁷)-L³-S—R⁵, —C(O)N(R⁷)—R⁵, —C(O)N(R⁷)-L²-N(R⁷)—R⁵, —C(O)N(R⁷)-L²-O—R⁵, —C(O)N(R⁷)-L²-S—R⁵, —C(O)N(R⁷)-L²-C(O)O—R⁵, —C(O)N(R⁷)-L²-C(O)N(R⁸)—R⁵—, —C(O)N(R⁷)-L²-C(O)N(R⁸)-L³-N(R⁷)—R⁵, —C(O)O-L²-N(R⁷)C(O)O—R⁵, —C(O)N(R⁸)-L²-N(R⁷)C(O)O—R⁵, —C(O)O-L²-N(R⁷)C(O)N(R⁸)—R⁵, —C(O)N(R⁷)-L²-N(R⁷)C(O)N(R⁸)—R⁵, —C(O)N(R⁷)-L²-C(O)N(R⁸)-L³-O—R⁵ or —C(O)N(R⁷)-L²-C(O)N(R⁸)-L³-S—R⁵;

—Z— is —C(O)—, —C(O)O—, or —C(O)N(R⁷)—;

-L⁴-R⁵ is —(C1-C10 alkylene)-N(R⁷)—R⁵, —(C1-C10 alkylene)-O—R⁵, —(C1-C10 alkyl)-S—R⁵, —(C2-C10 alkenylene)-N(R⁷)—R⁵, —(C2-C10 alkenylene)-O—R⁵ or —(C2-C10 alkenylene)-S—R⁵;

R⁷ and R⁸ each is independently H, C1-C10 alkyl, or C2-C10 alkenyl;

R⁹ is independently H, —F, C1-C10 alkyl, or C2-C10 alkenyl;

$L^2$ and $L^3$ each is —(C1-C10 alkylene)-, or —(C2-C10 alkenylene)-; and
X is a halogen atom.
In some embodiments of formula (1), $R^1$, $R^{1'}$, and $R^2$ are each independently:
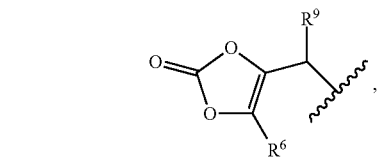
(9)
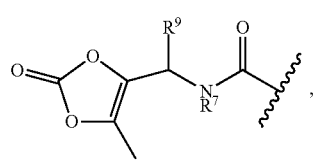
(10)
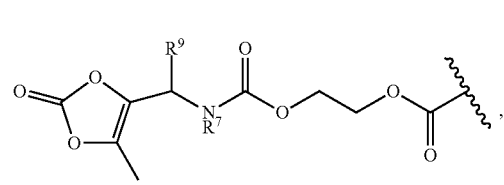
(11)
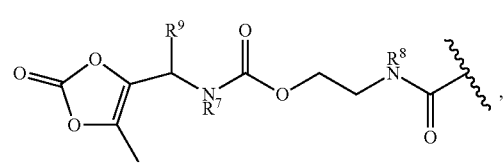
(12)
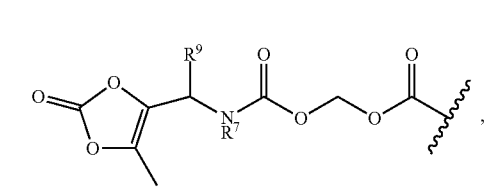
(13)
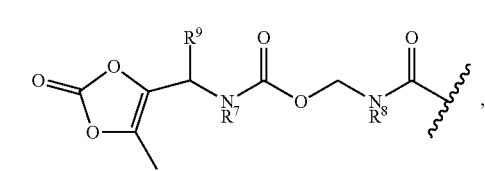
(14)
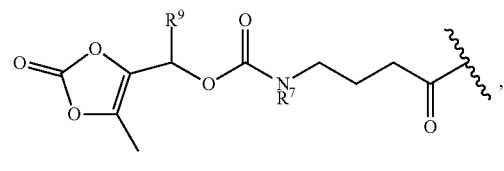
(15)
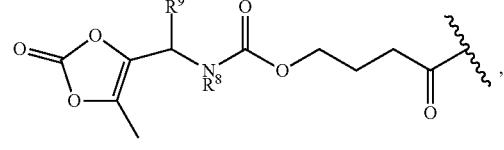
(16)
-continued
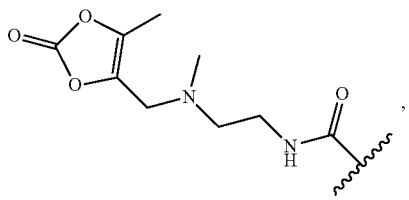
(17)
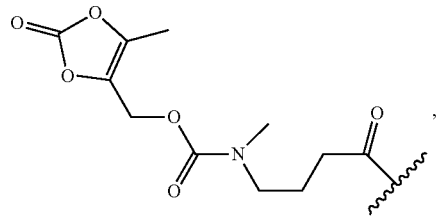
(18)
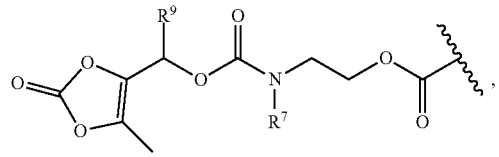
(19)
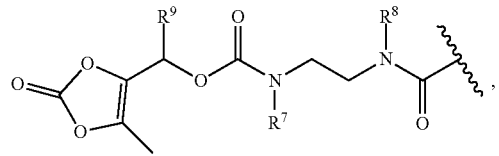
(20)
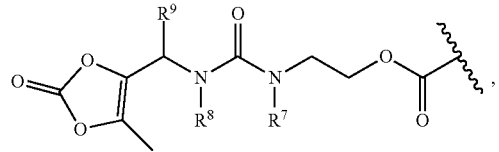
(21)
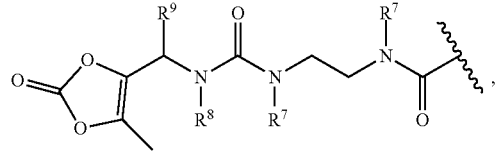
(22)
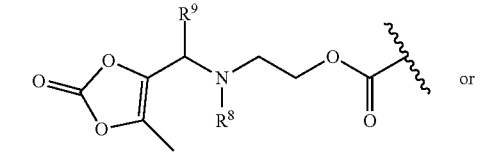
(23)
or
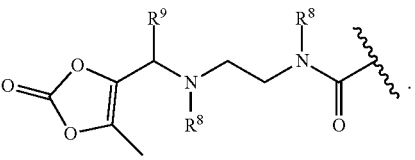
(24)

In some embodiments, the adenosine derivative is selected from the group consisting of:

formula (2-A)

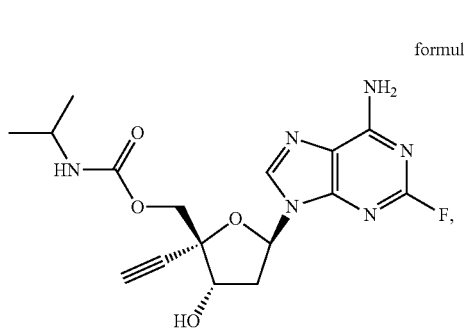

formula (3-A)

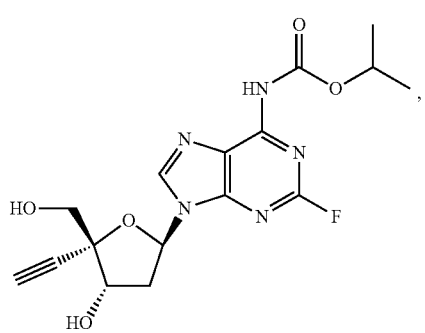

formula (4-A)

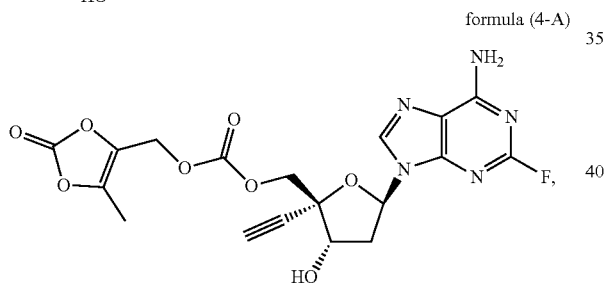

formula (5-A)

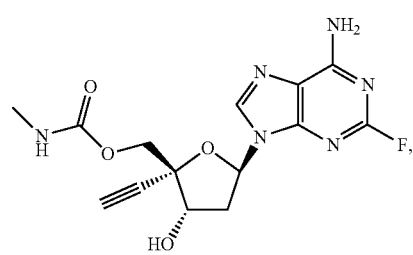

formula (6-A)

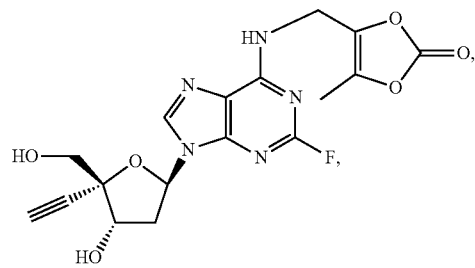

formula (7-A)

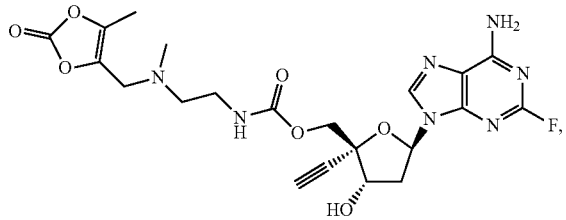

formula (8-A)

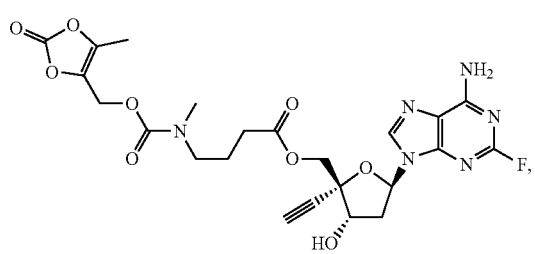

formula (4-C)

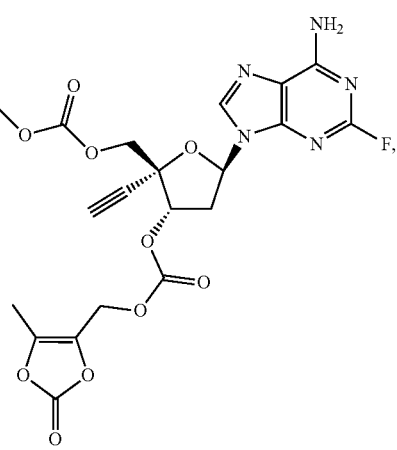

or a pharmaceutically acceptable salt, tautomer, or solvate thereof.

In some embodiments, the adenosine derivative is a compound having the structure:

(4-A)

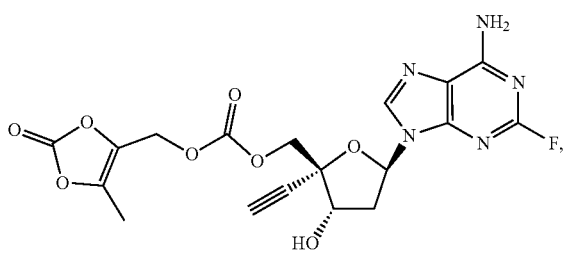

or a pharmaceutically acceptable salt, tautomer, or solvate thereof.

In some embodiments, the CA inhibitor is a compound having the structure:

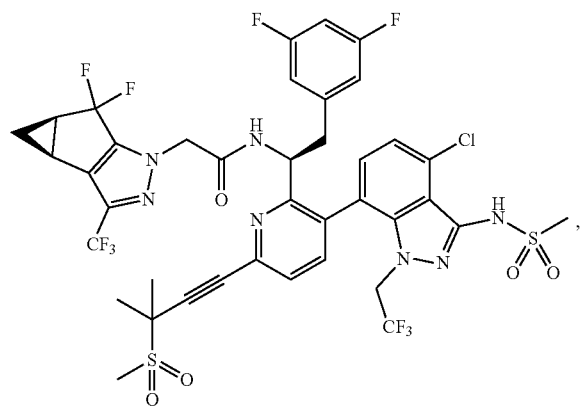 [SMILES: CC(C)(C#Cc1ccc(-c2ccc(Cl)c3c(NS(C)(=O)=O)nn(CC(F)(F)F)c23)c([C@H](Cc2cc(F)cc(F)c2)NC(=O)Cn2nc(C(F)(F)F)c3c2C(F)(F)[C@@H]2C[C@H]32)n1)S(C)(=O)=O]

or a pharmaceutically acceptable salt, tautomer, or solvate thereof.

BRIEF DESCRIPTION OF THE FIGURES

FIG. 1. A representative non-limiting example of a Mean 3-D Surface Plot of Formula 4-A and lenacapavir antiviral drug interactions.

DETAILED DESCRIPTION

Following are more detailed descriptions of various concepts related to, and embodiments of, methods and apparatus according to the present disclosure. It should be appreciated that various aspects of the subject matter introduced above and discussed in greater detail below may be implemented in any of numerous ways, as the subject matter is not limited to any particular manner of implementation. Examples of specific implementations and applications are provided primarily for illustrative purposes.

Definitions

As used herein, the term "alkyl" or "alkyl group" refers to a fully saturated, straight or branched hydrocarbon chain having from one to twelve carbon atoms, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes C6 alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

As used herein, the term "alkylene" or "alkylene chain" refers to a fully saturated, straight or branched divalent hydrocarbon chain radical, and having from one to twelve carbon atoms. Non-limiting examples of $C_1$-$C_{12}$ alkylene include methylene, ethylene, propylene, n-butylene, and the like. The alkylene chain is attached to the rest of the molecule through a single bond and to a radical group (e.g., those described herein) through a single bond. The points of attachment of the alkylene chain to the rest of the molecule and to the radical group can be through one carbon or any two carbons within the chain. Unless stated otherwise specifically in the specification, an alkylene chain can be optionally substituted.

As used herein, the term "alkenyl" or "alkenyl group" refers to a linear or branched chain aliphatic hydrocarbon radical containing at least one carbon-carbon double bond and having a number of carbon atoms in the specified range. For example, "C2-C10 alkenyl" (or "$C_2$-$C_{10}$ alkenyl") refers to any of alkenyl having 2 to 10 carbon atoms that is linear or branched, or isomers. In another example C2-C6 alkenyl can have 1-butenyl, 2-butenyl, 3-butenyl, isobutenyl, 1-propenyl, 2-propenyl, and ethenyl (or vinyl). The points of attachment of the alkylene chain to the rest of the molecule and to the radical group can be through one carbon or any two carbons within the chain. Unless stated otherwise specifically in the specification, an alkylene chain can be optionally substituted.

As used herein, the term "alkenylene" or "alkenylene chain" refers to an unsaturated, straight or branched divalent hydrocarbon chain radical having one or more olefins and from two to twelve carbon atoms. Non-limiting examples of $C_2$-$C_{12}$ alkenylene include ethenylene, propenylene, n-butenylene, and the like. The alkenylene chain is attached to the rest of the molecule through a single bond and to a radical group (e.g., those described herein) through a single bond. The points of attachment of the alkenylene chain to the rest of the molecule and to the radical group can be through one carbon or any two carbons within the chain. Unless stated otherwise specifically in the specification, an alkenylene chain can be optionally substituted.

As used herein, the term "cycloalkyl" refers to a stable non-aromatic monocyclic or polycyclic fully saturated hydrocarbon consisting solely of carbon and hydrogen atoms, which can include fused or bridged ring systems, having from three to twenty carbon atoms (e.g., having from three to ten carbon atoms) and which is attached to the rest of the molecule by a single bond. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, 7,7-dimethyl-bicyclo[2.2.1]heptanyl, and the like. In some embodiments, "cycloalkyl" refers to any monocyclic ring of an alkane having a number of carbon atoms in the specified range. For example, "C3-C10 cycloalkyl" (or "$C_3$-$C_{10}$ cycloalkyl") refers to monocyclic ring of an alkane having 3 to 10 carbon atoms, such as cyclopropyl, cyclobutyl, cyclopentyl, cyclohexyl, and cycloheptyl. Unless otherwise stated specifically in the specification, a cycloalkyl group can be optionally substituted.

As used herein, the term heterocycloalkyl," "heterocyclic ring" or "heterocycle" refers to a saturated, or partially saturated 3- to 20-membered ring which consists of two to nineteen carbon atoms and from one to six heteroatoms selected from the group consisting of nitrogen, oxygen and sulfur, and which is attached to the rest of the molecule by a single bond. Unless stated otherwise specifically in the specification, the heterocycloalkyl can be a monocyclic, bicyclic, tricyclic or tetracyclic ring system, which can include fused or bridged ring systems; and the nitrogen, carbon or sulfur atoms in the heterocycloalkyl can be optionally oxidized, e.g., to form an N-oxide, sulfoxide, or sulfone and/or the nitrogen atom can be optionally quaternized, e.g., to form a quaternary ammonium cation. Examples of such heterocycloalkyls include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, 1-oxo-thiomorpholinyl, and 1,1-dioxo-thiomorpholinyl. In some embodiments, "3- to 10-membered heterocycloalkyl" refers to a cycloalkyl comprising one or more heteroatoms, selected from the group consisting of N, O, and S. In some embodiments, "heterocycloalkyl", "heterocyclic ring" or "heterocycle" refers to a 3-10 member ring structure having carbon atoms and one or more heteroatoms selected from N, O, S or a combination thereof as members of the ring structure. Unless stated otherwise specifically in the specification, a heterocycloalkyl group can be optionally substituted and include saturated and/or unsaturated rings.

As used herein, the term "halogen" (or "halo") refers to fluorine, chlorine, bromine and iodine (alternatively referred to as fluoro (—F), chloro (—Cl), bromo (—Br), and iodo (—I)).

As used herein, the term "aryl" refers to a hydrocarbon ring system comprising hydrogen, 6 to 18 carbon atoms and at least one aromatic ring, and which is attached to the rest of the molecule by a single bond. For purposes of the present disclosure, the aryl can be a monocyclic, bicyclic, tricyclic or tetracyclic ring system, which can include fused or bridged ring systems. Aryls include, but are not limited to, aryls derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, "aryl" refers to phenyl or one or more fused cyclic hydrocarbon ring systems in which at least one ring is aromatic. Unless stated otherwise specifically in the specification, the "aryl" can be optionally substituted.

As used herein, the term "heteroaryl" refers to a 5- to 20-membered ring system comprising hydrogen atoms, one to nineteen carbon atoms, one to six heteroatoms selected from the group consisting of nitrogen, oxygen and sulfur, at least one aromatic ring, and which is attached to the rest of the molecule by a single bond. For purposes of the present disclosure, the heteroaryl can be a monocyclic, bicyclic, tricyclic or tetracyclic ring system, which can include fused or bridged ring systems; and the nitrogen, carbon or sulfur atoms in the heteroaryl can be optionally oxidized, e.g., to form an N-oxide, sulfoxide, or sulfone and/or the nitrogen atom can be optionally quaternized, e.g., to form a quaternary ammonium cation. Non-limiting examples of heteroaryls can include pyridyl, pyrrolyl, pyrazinyl, pyrimidinyl, pyridazinyl, triazinyl, thienyl, furanyl, imidazolyl, pyrazolyl, triazolyl triazolyl (i.e., 1,2,3-triazolyl or 1,2,4-triazolyl), tetrazolyl, oxazolyl, isooxazolyl, oxadiazolyl (i.e., the 1,2,3-, 1,2,4-, 1,2,5-(furazanyl), or 1,3,4-isomer), oxatriazolyl, thiazolyl, isothiazolyl, and thiadiazolyl. Suitable 9- and 10-membered heterobicyclic, fused ring systems include, for example, benzofuranyl, indolyl, indazolyl, naphthyridinyl, isobenzofuranyl, benzopiperidinyl, benzisoxazolyl, benzoxazolyl, chromenyl, quinolinyl, isoquinolinyl, cinnolinyl, quinazolinyl, tetrahydro uinolinyl, tetrahydroisoquinolinyl, isoindolyl, benzodioxolyl, benzopiperidinyl, benzisoxazolyl, benzoxazolyl, chromanyl, isochromanyl, benzothienyl, benzofuranyl, imidazo[1,2-a]pyridinyl, benzotriazolyl, dihydroindolyl, dihydroisoindolyl, indazolyl, indolinyl, isoindolinyl, quinoxalinyl, quinazolinyl, 2,3-dihydrobenzofuranyl, and 2,3-dihydrobenzo-1,4-dioxinyl. Unless stated otherwise specifically in the specification, a heteroaryl group can be optionally substituted.

It is understood that, unless expressly stated to the contrary in a particular context, any of the various cyclic rings and ring systems described herein may be attached to the rest of the compound at any ring atom (i.e., any carbon atom or any heteroatom) provided that the attachment is chemically allowed.

As used herein, the term "substituted" means any of the groups described herein (e.g., alkyl, alkenyl, alkynyl, alkoxy, aryl, aralkyl, carbocyclyl, cycloalkyl, cycloalkenyl, cycloalkynyl, haloalkyl, heterocyclyl, and/or heteroaryl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents.

As used herein, the term "isomer" refers to a structural isomer, such as a group or an atom positioned at different locations of a molecule; stereoisomer, such as a chiral isomer, enantiomers, diastereomers and cis/trans isomers; a tautomer, such as amino isomer, imino isomer, or a combination thereof. In non-limiting examples, an adenosine derivative of the present disclosure can have an amino isomer, an imino isomer or a combination thereof. In another non-limiting example, in instances where an —OH substituent is permitted on a heteroaromatic ring and keto-enol tautomerism is possible, it is understood that the substituent might in fact be present, in whole or in part, in the oxo (=O) form. A mixture of isomers can also be suitable. A mixture of isomers can comprise the respective isomers in all ratios. A salt of an isomer can also be suitable. An adenosine derivative of the present disclosure can comprise isomers thereof, one or more salts thereof, one or more solvates including hydrates thereof, solvated salts thereof or a mixture thereof. Absolute stereochemistry or isomer configuration may be determined by X-ray crystallography, by Vibrational Circular Dichroism (VCD) spectroscopy analysis or a combination thereof.

The adenosine derivatives can be identified by names based on the nomenclature recommended by International Union of Pure and Applied Chemistry (IUPAC) or based on nucleosides (Nucleoside-based nomenclature). The adenosine derivatives can also be identified by chemical structure drawings. Unless expressly stated to the contrary in a particular context, the names and the structures may be used interchangeably.

Any of the atoms in a compound disclosed herein may exhibit their natural isotopic abundances, or one or more of the atoms may be artificially enriched in a particular isotope having the same atomic number, but an atomic mass or mass number different from the atomic mass or mass number predominantly found in nature. The present disclosure is meant to include all suitable isotopic variations of the compounds disclosed herein.

The compounds can be administered in the form of pharmaceutically acceptable salts or solvates. The term "pharmaceutically acceptable salt" refers to a salt or a solvate which is not biologically or otherwise undesirable (e.g., is neither toxic nor otherwise deleterious to the recipient or subject thereof). A mixture of a compound disclosed herein and one or more salts or solvates thereof is also contemplated herein. Illustrative examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

Furthermore, compounds disclosed herein can exist in amorphous form and/or one or more crystalline forms, or a combination thereof.

The term "retrovirus" or "retroviral infection" refers to a virus that uses RNA as its genetic material. When a retrovirus infects a cell, it makes a DNA copy of its genome that is inserted into the DNA of the host cell.

The term "RNA virus infection" refers to a disease caused by an RNA virus, such as the common cold, influenza, SARS, COVID-19, hepatitis C, hepatitis E, West Nile fever, Ebola virus disease, rabies, polio, and measles.

The term "HIV infection" refers to a disease caused by the human immunodeficiency virus (HIV), such as HIV-1 and HIV-2. In some cases, the HIV infection can be caused by wild-type HIV-1, NRTI-resistant HIV-1, HIV-2, HIV having M184V mutations, HIV having K65R, or multidrug resistant HIV. The term "AIDS" refers to acquired immunodeficiency syndrome, which is caused by HIV infection and an advanced form of the disease.

The term "prodrug" refers to a compound that may be converted under physiological conditions or by solvolysis to a biologically active compound described herein. Thus, the term "prodrug" refers to a precursor of a biologically active compound that is pharmaceutically acceptable. A prodrug may be a biologically inactive or substantially inactive compound which can be metabolized in the body, i.e., in vivo, to produce a drug having a desired activity. The term "substantially inactive" means that a prodrug can have about 1% to about 10% of the activity of the corresponding drug or after being metabolized in vivo, percentage based on weight of the prodrug. In some embodiments, the term "substantially inactive" means that a prodrug has less than about 5% of the activity of the corresponding drug or after being metabolized in vivo, percentage based on weight of the prodrug. The doses for a prodrug and its biologically active compound are considered to be does-equivalent when they are the same molar amount.

The term "anti-HIV agent", "anti-viral agent" or a grammatical variant refers to a compound, a mixture of one or more compounds, a formulation, a chemical agent or a biological agent such as antibody, protein, peptides, nucleotide, other biological compound, or a combination thereof, that can be directly or indirectly effective in the inhibition of HIV, the treatment or prophylaxis of HIV infection, and/or the treatment, prophylaxis or delay in the onset or progression of AIDS and/or diseases or conditions arising therefrom or associated therewith, an RNA virus infection, or a combination thereof. The anti-HIV agents can comprise HIV antiviral agents, immunomodulators, anti-infectives, vaccines or a combination thereof useful for treating HIV infection or AIDS. Examples of antiviral agents for Treating HIV infection or AIDS include, but are not limited to, under respective trademarks or registered trademarks with respective owners, abacavir (ABC, Ziagen®), abacavir+lamivudine (Epzicom®), abacavir+lamivudine+zidovudine (Trizivir®), amprenavir (Agenerase®), atazanavir (Reyataz®), AZT (zidovudine, azidothymidine or Retrovir®), capravirine, darunavir (Prezista®), ddC (zalcitabine, dideoxycytidine or Hivid®), ddI (didanosine, dideoxyinosine or Videx®), ddI (enteric coated, Videx EC®), delavirdine (DLV or Rescriptor®), dolutegravir (Tivicay®), doravirine (MK-1439), efavirenz (EFV, Sustiva®, Stocrin®), efavirenz+emtricitabine+tenofovir DF (Atripla®), EFdA (4'-ethynyl-2-fluoro-2'-deoxyadenosine), elvitegravir, cabotegravir, dolutegravir, bictegravir, emtricitabine (FTC, Emtriva®), emtricitabine+tenofovir DF (Truvada®), emvirine (Coactinon®), enfuvirtide (Fuzeon®), enteric coated didanosine (Videx EC®), etravirine (TMC-125), fosamprenavir calcium (Lexiva®), indinavir (Crixivan®, lamivudine (3TC, Epivir®), lamivudine+zidovudine (Combivir®), lopinavir, lopinavir+ritonavir (Kaletra®), maraviroc (Selzentry®), nelfinavir (Viracept®), nevirapine (NVP, Viramune®), PPL-100 (also known as PL-462) (Ambrilia), raltegravir (MK-0518 or Isentress'''), rilpivirine (Edurant®), ritonavir (Norvir®), saquinavir (Invirase®, or Fortovase®), stavudine (d4T, didehydrodeoxythymidine or Zerit®), tenofovir DF (DF=disoproxil fumarate, TDF, Viread®), Tenofovir (hexadecyloxypropyl (CMX-157), Tenofovir alafenamide fumarate (GS-7340), tipranavir (Aptivus®) and vicriviroc. Some of the anti-HIV agents shown above can be used in a salt form; for example, abacavir sulfate, delavirdine mesylate, indinavir sulfate, atazanavir sulfate, nelfinavir mesylate, saquinavir mesylate or other salts. An anti-HIV agent can have one or more activities such as entry inhibitor (EI), fusion inhibitor (FI); integrase inhibitor (InI); protease inhibitor (PI); nucleoside reverse transcriptase inhibitor (nRTI or NRTI) or non-nucleoside reverse transcriptase inhibitor (nnRTI or NNRTI). An anti-HIV agent can comprise two or more agents disclosed herein. The adenosine derivative of the present disclosure can be an anti-HIV agent along or in combination with other anti-HIV agent or agents.

Unless expressly stated to the contrary, all ranges cited herein are inclusive. It is to be understood that any range cited herein includes within its scope all of the sub-ranges within that range. For example, a dosage in a range of from "100 to 2000 mg" means the dosage of 100 mg, 101 mg, 101.1 mg, 101.01 mg and so on, and 2000 mg including all dosages within the range. In another non-limiting example, a time range of "1 to 8 days" means 1 day, 2, days, 3 days, 4 days, 5 days, 6 days, 7 days, and 8 days including all times subranges or each and every individual time point or time points within the range. In yet another non-limiting example, a heteroaryl ring described as comprising in a range of from "1 to 4 heteroatoms" means the ring can comprise 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, or 4 heteroatoms. In other examples, C1-C10 alkyl means an alkyl comprises 1, 2, 3, 4, 5, 6, 7, 8, 9 and 10 carbon atoms including all sub-ranges. Thus, a C1-C10 alkyl can be a methyl, ethyl, C4 alkyl, C5 alkyl, C6 alkyl, C7 alkyl, C8 alkyl, C9 alkyl and C10 alkyl, linear or branched. C1-C10 alkyl can be a —CH$_2$—, —C$_2$H$_4$—, —C$_3$H$_6$—, —C$_4$H$_8$—, —C$_5$H$_{10}$—, —C$_6$H$_{12}$—, —C$_7$H$_{17}$—, —C$_8$H$_{18}$—, —C$_9$H$_{18}$— or —C$_{10}$H$_{20}$—, linear or a branched. Similarly, C2-C10 alkenyl means an alkenyl comprises 2, 3, 4, 5, 6, 7, 8, 9 and 10 carbon atoms, linear or branched, including all sub-ranges. A linear or a branched alkenyl can be suitable. A C$_3$-C$_{10}$ cycloalkyl means a cycloalkyl comprises 3, 4, 5, 6, 7, 8, 9 and 10 carbon atoms, linear or branched.

Unless otherwise indicated, open terms for example "contain," "containing," "include," "including," and the like mean comprising.

The singular forms "a", "an", and "the" are used herein to include plural references unless the context clearly dictates otherwise. Accordingly, unless the contrary is indicated, the numerical parameters set forth in this application are approximations that may vary depending upon the desired properties sought to be obtained by the present disclosure.

The term "about" and its grammatical equivalents in relation to a reference numerical value and its grammatical equivalents as used herein can include a range of values plus or minus 10% from that value, such as a range of values plus or minus 10%, 9%, 8%, 7%, 6%, 5%, 4%, 3%, 2%, or 1% from that value. For example, the amount "about 10" includes amounts from 9 to 11.

The term "injection" refers to intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Other non-parenteral route can include, such as a topical, epidermal or mucosal route of administration, e.g., intranasally, orally, vaginally, rectally, sublingually or topically. The pharmaceutical composition can be in the form of sterile aqueous solutions or dispersions. The pharmaceutical composition can also be formulated in a microemulsion, liposome, or other ordered structure suitable to high drug concentration.

COMPOUNDS OF THE DISCLOSURE

In some embodiments, the present disclosure provides an adenosine derivative having a structure of formula (1):

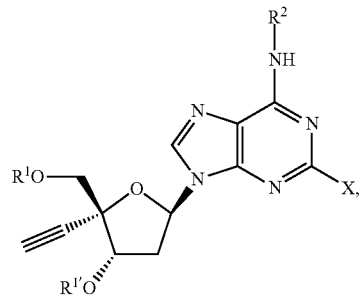

or a pharmaceutically acceptable salt, tautomer, or solvate thereof,
wherein:
$R^1$, $R^{1'}$, and $R^2$ each is independently H, —C(O)N($R^3$)($R^{3'}$), —C(O)O$R^4$, —$R^5$, -$L^1$-$R^5$, or —Z-$L^4$-$R^5$, provided that least one of $R^1$ and $R^2$ is not H;
$R^3$, $R^{3'}$ and $R^4$ each is independently H, C1-C10 alkyl, C2-C10 alkenyl, C3-C10 cycloalkyl, 3- to 10-membered heterocycloalkyl, aryl, or heteroaryl;
$R^5$ is:

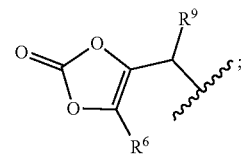

$R^6$ is H, C1-C10 alkyl, C2-C10 alkenyl, C3-C10 cycloalkyl, 3- to 10-membered heterocycloalkyl, aryl, or heteroaryl;
-$L^1$-$R^5$ is —(C1-C10 alkylene)-N($R^7$)—$R^5$, —(C1-C10 alkylene)-O—$R^5$, —(C1-C10 alkylene)-S—$R^5$, —(C2-C10 alkenylene)-N($R^7$)—$R^5$, —(C2-C10 alkenylene)-O—$R^5$, —(C2-C10 alkenylene)-S—$R^5$, —C(O)O—$R^5$, —C(O)O-$L^2$-N($R^7$)—$R^5$, —C(O)O-$L^2$-O—$R^5$, —C(O)O-$L^2$-S—$R^5$, —C(O)O-$L^2$-C(O)O—$R^5$, —C(O)O-$L^2$-C(O)N($R^7$)—$R^5$, —C(O)O-$L^2$-C(O)N($R^7$)-$L^3$-N($R^7$)—$R^5$, —C(O)O-$L^2$-C(O)N($R^7$)-$L^3$-O—

R$^5$, —C(O)O-L$^2$-C(O)N(R$^7$)-L$^3$-S—R$^5$, —C(O)N(R$^7$)—R$^5$, —C(O)N(R$^7$)-L$^2$-N(R$^7$)—R$^5$, —C(O)N(R$^7$)-L$^2$-O—R$^5$, —C(O)N(R$^7$)-L$^2$-S—R$^5$, —C(O)N(R$^7$)-L$^2$-C(O)O—R$^5$, —C(O)N(R$^7$)-L$^2$-C(O)N(R$^8$)—R$^5$—, —C(O)N(R$^7$)-L$^2$-C(O)N(R$^8$)-L$^3$-N(R$^7$)—R$^5$, —C(O)O-L$^2$-N(R$^7$)C(O)O—R$^5$, —C(O)N(R$^8$)-L$^2$-N(R$^7$)C(O)O—R$^5$, —C(O)O-L$^2$-N(R$^7$)C(O)N(R$^8$)—R$^5$, —C(O)N(R$^7$)-L$^2$-N(R$^7$)C(O)N(R$^8$)—R$^5$, —C(O)N(R$^7$)-L$^2$-C(O)N(R$^8$)-L$^3$-O—R$^5$ or —C(O)N(R$^7$)-L$^2$-C(O)N(R$^8$)-L$^3$-S—R$^5$;

—Z— is —C(O)—, —C(O)O—, or —C(O)N(R$^7$)—;

-L$^4$-R$^5$ is —(C1-C10 alkylene)-N(R$^7$)—R$^5$, —(C1-C10 alkylene)-O—R$^5$, —(C1-C10 alkylene)-S—R$^5$, —(C2-C10 alkenylene)-N(R$^7$)—R$^5$, —(C2-C10 alkenylene)-O—R$^5$ or —(C2-C10 alkenylene)-S—R$^5$;

R$^7$ and R$^8$ each is independently H, C1-C10 alkyl, or C2-C10 alkenyl;

R$^9$ is independently H, —F, C1-C10 alkyl, or C2-C10 alkenyl;

L$^2$ and L$^3$ each is divalent —(C1-C10 alkylene)-, or —(C2-C10 alkenylene)-; and X is a halogen atom.

An adenosine derivative of the present disclosure can be free from a monophosphate group, diphosphate group, tri-phosphate group or a combination thereof. In some embodiments, the R$^1$, R$^{1'}$ or R$^2$ group of an adenosine derivative of the present disclosure is free from a monophosphate group, diphosphate group, tri-phosphate group or a combination thereof. Non-limiting examples of adenosine derivatives having a halogen atom are shown in formulas (1)-(8) and (4-B).

In some embodiments of formula (1), the C1-C10 alkyl and C2-C10 alkenyl is linear or branched. In some embodiments, the compounds of formula (1) comprise a combination of C1-C10 alkyl, C2-C10 alkenyl, C3-C10 cycloalkyl, 3- to 10-membered heterocycloalkyl, aryl and heteroaryl groups.

In some embodiments, R$^1$ and R$^{1'}$ each is independently selected from one of formulas 9-24. In some embodiments, R$^2$ is H, —COO(C1-C3 alkyl) or

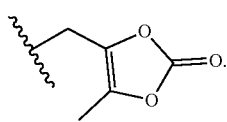 [SMILES: *Cc1oc(=O)oc1C]

In some embodiments, R$^2$ is H.

In some embodiments, R$^2$ is selected from one of formulas 9-24. In some embodiments, R$^1$ and R$^{1'}$ each is independently H, —COO(C1-C3 alkyl) or

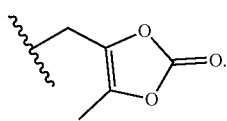

In some embodiments, R$^1$ is H, —COO(C1-C3 alkyl) or

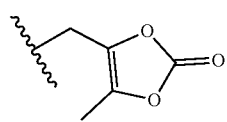 [SMILES: *Cc1oc(=O)oc1C]

and R$^{1'}$ is H. In some embodiments, R$^{1'}$ is H, —COO(C1-C3 alkyl) or

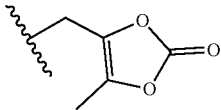 [SMILES: *Cc1oc(=O)oc1C]

and R is H.

In some embodiments, R$^3$ and R$^{3'}$ each is independently H, C1-C5 alkyl, C2-C5 alkenyl, C3-C6 cycloalkyl, 3- to 6-membered heterocycloalkyl, phenyl, or 5- to 6-membered heteroaryl. In some embodiments, R$^3$ and R$^{3'}$ each is independently H, C1-C5 alkyl, C3-C6 cycloalkyl, 3- to 6-membered heterocycloalkyl, phenyl, or 5- to 6-membered heteroaryl. In some embodiments, R$^3$ and R$^{3'}$ each is independently H or C1-C5 alkyl. In some embodiments, R$^3$ and R$^{3'}$ each is independently H or C1-C3 alkyl. In some embodiments, R$^3$ and R$^{3'}$ each is independently H, methyl, ethyl, or isopropyl.

In some embodiments, R$^4$ is H, C1-C5 alkyl, C2-C5 alkenyl, C3-C6 cycloalkyl, 3- to 6-membered heterocycloalkyl, phenyl, or 5- to 6-membered heteroaryl. In some embodiments, R$^4$ is H, C1-C5 alkyl, C3-C6 cycloalkyl, 3- to 6-membered heterocycloalkyl, phenyl, or 5- to 6-membered heteroaryl. In some embodiments, R$^4$ is H or C1-C5 alkyl. In some embodiments, R$^4$ is H or C1-C3 alkyl. In some embodiments, R$^4$ is H, methyl, ethyl, or isopropyl.

In some embodiments of formula (1), R$^1$ is H and R$^2$ is —C(O)N(R$^3$)(R$^{3'}$). In some embodiments, R$^1$ is —C(O)N(R$^3$)(R$^{3'}$) and R$^2$ is H. In some embodiments, R$^3$ is C1-C5 alkyl or C3-C6 cycloalkyl and R$^{3'}$ is H. In some embodiments, R$^3$ is methyl, ethyl, or isopropyl and R$^{3'}$ is H. In some embodiments, R$^3$ is methyl and R$^{3'}$ is H.

In some embodiments of formula (1), R$^1$ is H and R$^2$ is —R$^5$ or -L$^1$-R$^5$. In some embodiments, R$^1$ is -L$^1$-R$^5$ and R$^2$ is H. In some embodiments, -L$^1$-R$^5$ is —C(O)N(R$^7$)-L$^2$-N(R$^7$)—R$^5$, —C(O)O-L$^2$-OR$^5$, —C(O)N(R$^7$)-L$^2$-N(R$^7$)—C(O)O—R$^5$, —C(O)O-L$^2$-N(R$^7$)—C(O)O—R$^5$, —C(O)N(R$^7$)-L$^2$-N(R$^8$)—C(O)N(R$^8$)—R$^5$, or —C(O)O-L$^2$-N(R$^8$)—C(O)N(R$^8$)—R$^5$. In some embodiments, R$^5$ is

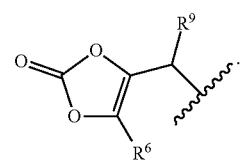

In some embodiments, R$^6$ is C1-C5 alkyl. In some embodiments, R$^6$ is methyl, ethyl, or isopropyl. In some embodiments, R$^6$ is methyl. In some embodiments, R$^7$ is H or Me. In some embodiments, R$^9$ is H, F, or C1-C5 alkyl. In some embodiments, R$^9$ is H, F, or Me. In some embodiments, R$^9$ is H. In some embodiments, L$^2$ is C2-C5 alkylene. In some embodiments, L$^2$ is ethylene or propylene. In some embodiments, L$^2$ is ethylene.

In some embodiments of formula (1), R$^1$ is —C(O)O—R$^5$ or —R$^5$ and R$^2$ is H. In some embodiments, R$^1$ is H and R$^2$ is —C(O)O—R$^5$ or —R$^5$. In some embodiments, R$^5$ is

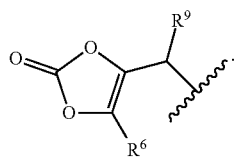

In some embodiments, $R^6$ is C1-C5 alkyl. In some embodiments, $R^6$ is methyl, ethyl, or isopropyl. In some embodiments, $R^6$ is methyl. In some embodiments, $R^9$ is H, F, or Me. In some embodiments, $R^9$ is H.

In some embodiments of formula (1), $R^1$ is -$L^1$-$R^5$. In some embodiments, $R^{1'}$ is H or -$L^1$-$R^5$. In some embodiments, $R^{1'}$ is H. In some embodiments, $R^{1'}$ is -$L^1$-$R^5$. In some embodiments, $R^1$ is -$L^1$-$R^5$ and $R^{1'}$ is H. In some embodiments, $R^1$ is -$L^1$-$R^5$ and $R^{1'}$ is -$L^1$-$R^5$. In some embodiments, $R^1$ is -$L^1$-$R^5$, $R^{1'}$ is H, and $R^2$ is H. In some embodiments, $R^1$ is -$L^1$-$R^5$, $R^{1'}$ is -$L^1$-$R^5$, and $R^2$ is H. In some embodiments, -$L^1$-$R^5$ is selected from the group consisting of —(C1-C10 alkylene)-N($R^7$)—$R^5$, —(C1-C10 alkylene)-O—$R^5$, —C(O)O-$L^2$-N($R^7$)—$R^5$, —C(O)O-$L^2$-O—$R^5$, —C(O)O-$L^2$-C(O)O—$R^5$, —C(O)O-$L^2$-C(O)N($R^7$)—$R^5$, —C(O)N($R^7$)—$R^5$, —C(O)N($R^7$)-$L^2$-N($R^7$)—$R^5$, —C(O)N($R^7$)-$L^2$-O—$R^5$, —C(O)O-$L^2$-N($R^7$)C(O)O—$R^5$, —C(O)N($R^8$)-$L^2$-N($R^7$)C(O)O—$R^5$, —C(O)O-$L^2$-N($R^7$)C(O)N($R^8$)—$R^5$, —C(O)N($R^7$)-$L^2$-N($R^7$)C(O)N($R^8$)—$R^5$, —C(O)N($R^7$)-$L^2$-C(O)O—$R^5$, and —C(O)N($R^7$)-$L^2$-C(O)N($R^8$)—$R^5$—. In some embodiments, -$L^1$-$R^5$ is selected from the group consisting of —C(O)O—$R^5$, —C(O)O-$L^2$-N($R^7$)—$R^5$, —C(O)O-$L^2$-N($R^7$)C(O)O—$R^5$, —C(O)N($R^8$)-$L^2$-N($R^7$)C(O)O—$R^5$, —C(O)O-$L^2$-N($R^7$)C(O)N($R^8$)—$R^5$, —C(O)N($R^7$)-$L^2$-N($R^7$)C(O)N($R^8$)—$R^5$, —C(O)N($R^7$)-$L^2$-N($R^7$)—$R^5$, and —C(O)N($R^7$)-$L^2$-C(O)N($R^8$)—$R^5$—. In some embodiments, -$L^1$-$R^5$ is —C(O)O—$R^5$. In some embodiments, $R^2$ is H.

The divalent linker $L^1$ can also comprise one or more repeats of a same group or a combination of different groups. In some embodiments, $L^1$ comprises —C(O)O— and C1-C10 alkylene. In some embodiments, $L^1$ comprises two or more repeats of —C(O)O—. In some embodiments, $L^1$ comprises two or more repeats of —C(O)O(CH$_2$)$_n$—. In some embodiments, $L^1$ comprises two or more repeats of —C(O)N($R^7$)—. In some embodiments, $L^1$ comprises two or more repeats of —C(O)N($R^7$)(CH$_2$)$_n$—. In some embodiments, $L^1$ comprises a combination of —C(O)O—, C1-C10 alkylene, and —C(O)N($R^7$)—. In some embodiments, $L^1$ comprises a combination of —C(O)O—, —(CH$_2$)$_n$— and —C(O)N($R^7$)—. In some embodiments, $L^1$ comprises a combination of —C(O)N($R^7$)— and C1-C10 alkylene. In some embodiments, $L^1$ comprises two or more repeats of —C(O)O(CH$_2$)$_n$—C(O)N($R^7$)—. In some embodiments, $L^1$ is —C(O)O—. In some embodiments, $L^1$ is —C(O)N($R^7$)—. In some embodiments, n is an integer from 0 to 10. In some embodiments, n is an integer from 1 to 3. As understood in the art, the above combinations are non-limiting examples, and other chemically possible combinations of $L^1$ are also contemplated by the present disclosure.

In some embodiments, $R^6$ is H, C1-C5 alkyl, C2-C4 alkenyl, C3-C6 cycloalkyl, 3- to 6-membered heterocycloalkyl, phenyl, or 5- to 6-membered heteroaryl. In some embodiments, $R^6$ is H, C1-C10 alkyl, C2-C10 alkenyl, or C3-C10 cycloalkyl. In some embodiments, $R^6$ is H, C1-C5 alkyl, C2-C5 alkenyl, or C3-C6 cycloalkyl. In some embodiments, $R^6$ is H, C1-C3 alkyl, or C2-C4 alkenyl. In some embodiments, $R^6$ is C1-C10 alkyl. In some embodiments, $R^6$ is C1-C5 alkyl. In some embodiments, $R^6$ is C1-C3 alkyl. In some embodiments, $R^6$ is selected from the group consisting of H, methyl, ethyl, isopropyl, and cyclopropyl. In some embodiments, $R^6$ is methyl, ethyl, or isopropyl. In some embodiments, $R^6$ is methyl. In some embodiments, $R^6$ is isopropyl.

In some embodiments, $R^7$ and $R^8$ each is independently H, C1-C10 alkyl, or C3-C6 cycloalkyl. In some embodiments, $R^7$ and $R^8$ each is independently H, C1-C5 alkyl, or C3-C6 cycloalkyl. In some embodiments, $R^7$ and $R^8$ each is independently H or C1-C5 alkyl. In some embodiments, the C1-C5 alkyl is methyl, ethyl, or isopropyl. In some embodiments, the C3-C6 cycloalkyl is cyclopropyl. In some embodiments, $R^7$ and $R^8$ each is independently H, methyl, ethyl, isopropyl, or cyclopropyl.

In some embodiments, $R^7$ is H or C1-C10 alkyl. In some embodiments, $R^7$ is H or C1-C5 alkyl. In some embodiments, the C1-C5 alkyl is methyl, ethyl, or isopropyl. In some embodiments, $R^7$ is H or Me. In some embodiments, $R^7$ is H.

In some embodiments, $R^8$ is H or C1-C10 alkyl. In some embodiments, $R^8$ is H or C1-C5 alkyl. In some embodiments, $R^8$ is H or Me. In some embodiments, $R^8$ is H.

In some embodiments, $R^9$ is H, F, C1-C10 alkyl, or C2-C10 alkenyl. In some embodiments $R^9$ is H, F, C1-C5 alkyl, or C2-C5 alkenyl. In some embodiments, $R^9$ is H, F, or C1-C5 alkyl. In some embodiments, $R^9$ is H, F, or C1-C3 alkyl. In some embodiments, $R^9$ is H or C1-C3 alkyl. In some embodiments, $R^9$ is C1-C3 alkyl. In some embodiments, $R^9$ is H, F, or Me. In some embodiments, $R^9$ is H, F, Me, or isopropyl. In some embodiments, $R^9$ is H or Me. In some embodiments, $R^9$ is H or F. In some embodiments, $R^9$ is H.

An adenosine derivative of the present disclosure can comprise one or more isomers thereof. An isomer can comprise a chiral isomer, also known as stereoisomer, that comprises one or more chiral centers, a tautomer that can interconvert via the relocation of a hydrogen atom and double bond, such as amino isomer, imino isomer, or a combination thereof. In non-limiting examples, an adenosine derivative can have an amino isomer, an imino isomer or a combination thereof. In further non-limiting examples, an adenosine derivative can comprise enantiomers, diastereomers and cis/trans isomers, tautomers or a combination thereof. An isomer that can have reverse transcriptase inhibitor (RTI) activity in vivo is also included.

In some embodiments of formula (1), X is a halogen atom selected from the group consisting of fluorine, chlorine, bromine and iodine (alternatively referred to as fluoro (F), chloro (Cl), bromo (Br), and iodo (I)). In some embodiments, X is F. In some embodiments, X is Cl. In some embodiments, X is Br.

In some embodiments, the adenosine derivative of the present disclosure comprises $R^1$, $R^{1'}$, and $R^2$, each independently comprising one or more 5- to 10-membered heterocyclic rings. In some embodiments, $R^1$, $R^{1'}$, or $R^2$ each independently comprises a 5-membered heterocyclic ring, a 6-membered heterocyclic ring, or a 6-10-membered heterocyclic ring. In some embodiments, $R^1$, $R^{1'}$, and $R^2$ each independently comprises a 6-10-membered heterocyclic ring. In some embodiments, $R^1$, $R^{1'}$, and $R^2$ each independently comprises a 5-membered heterocyclic ring. In some embodiments, $R^1$, $R^{1'}$, and $R^2$ each independently comprises a 6-membered heterocyclic ring. A heterocyclic ring of the present disclosure can have one or more substituents. In some embodiments, the 5-membered heterocyclic ring comprises 1 to 4 heteroatoms selected from the group consisting of N, O, S. In some embodiments, the 5-membered heterocyclic ring comprises 1 to 3 O atoms. In some embodiments, the 5-membered ring is a cyclic carbonate. In further embodiments, $R^1$, $R^{1'}$, and $R^2$ each independently comprises a 5-membered heterocyclic ring of formulas 9-24 disclosed herein. In even further embodiments, an adenosine derivative of the present disclosure comprises $R^1$, $R^{1'}$, and $R^2$ that each independently comprises an aforementioned —$R^5$, -$L^1$-$R^5$, —Z-$L^4$-$R^5$ group. In some embodiments, the —$R^5$, -$L^1$-$R^5$, —Z-$L^4$-$R^5$ is selected from formulas 9-24:

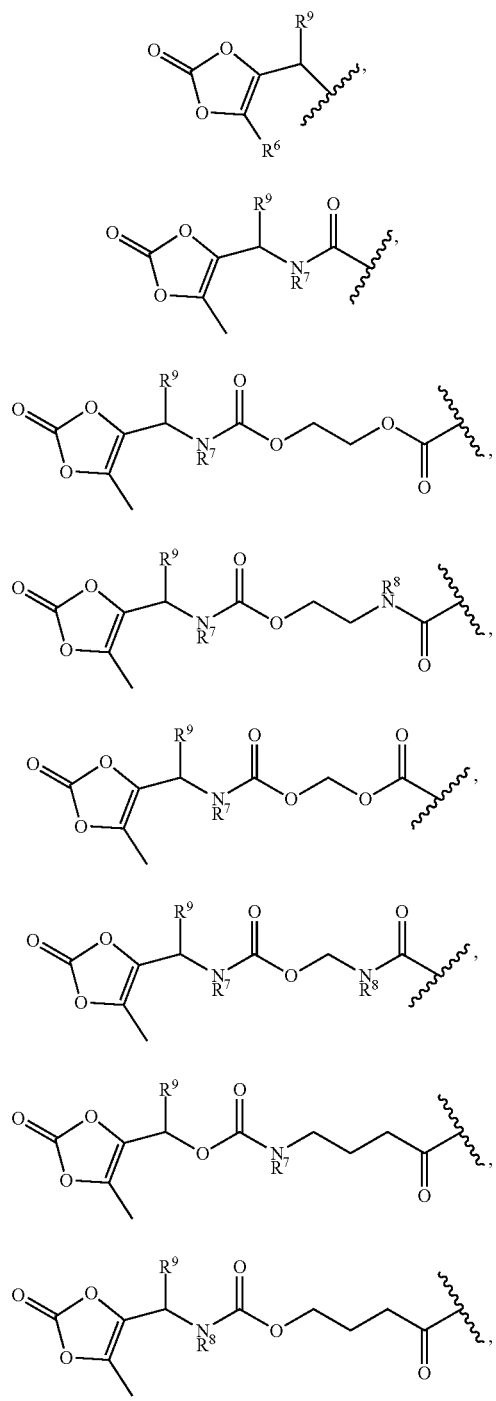

In some embodiments, —R$^5$, -L$^1$-R$^5$, —Z-L$^4$-R$^5$ is selected from group consisting of:

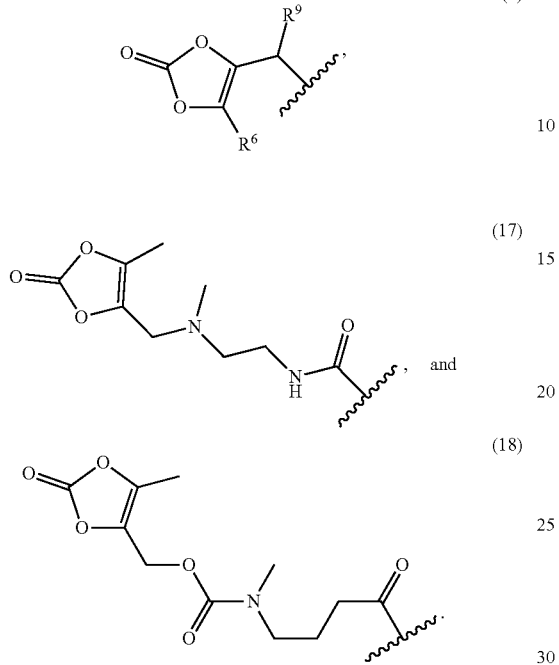

In some embodiments, an adenosine derivative of the present disclosure comprises R$^1$ and R$^{1'}$ that each is independently H, —C(O)N(R$^3$)(R$^{3'}$) or —C(O)OR$^4$ and R$^2$ that is —C(O)N(R$^3$)(R$^{3'}$), —C(O)OR$^4$ or one of formulas 9-24.

In some embodiments, an adenosine derivative of the present disclosure comprises R$^1$ and R$^{1'}$ that each is independently —C(O)N(R$^3$)(R$^{3'}$) or —C(O)OR$^4$ and R$^2$ that is H, —C(O)N(R$^3$)(R$^{3'}$), —C(O)OR$^4$ or one of formulas 9-24.

In some embodiments, an adenosine derivative of the present disclosure comprises R$^2$ that is H, —C(O)N(R$^3$)(R$^{3'}$) or —C(O)OR$^4$ and R$^1$ that is —C(O)N(R$^3$)(R$^{3'}$) or —C(O)OR$^4$ or one of formulas 9-24.

In some embodiments, an adenosine derivative of the present disclosure comprises R$^2$ that is —C(O)N(R$^3$)(R$^{3'}$) or —C(O)OR$^4$ and R$^1$ that is H, —C(O)N(R$^3$)(R$^{3'}$) —C(O)OR$^4$ or one of formulas 9-24.

In some embodiments, an adenosine derivative of the present disclosure comprises R$^1$ and R$^{1'}$ that each is H, —C(O)N(R$^3$)(R$^{3'}$), —C(O)OR$^4$, —R$^5$, -L$^1$-R$^5$, —Z-L$^4$-R$^5$ or one of one of formulas 9-24 and R$^2$ that is —C(O)N(R$^3$)(R$^{3'}$), —C(O)OR$^4$, —R$^5$, -L$^1$-R$^5$, —Z-L$^4$-R$^5$ or one of formulas 9-24.

In some embodiments, an adenosine derivative of the present disclosure comprises R$^1$ that is —C(O)N(R$^3$)(R$^{3'}$), —C(O)OR$^4$, —R$^5$, -L$^1$-R$^5$, —Z-L$^4$-R$^5$ or one of one of formulas 9-24 and R$^2$ that is H, —C(O)N(R$^3$)(R$^{3'}$), —C(O)OR$^4$, —R$^5$, -L$^1$-R$^5$, —Z-L$^4$-R$^5$ or one of formulas 9-24.

In some embodiments, each of R$^1$, R$^{1'}$ and R$^2$ is independently selected from one of formulas 9-24.

In some embodiments, the present disclosure is directed to an adenosine derivative having the structure of formula (1a):

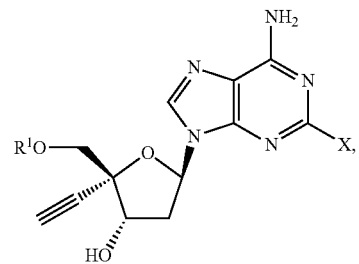

or pharmaceutically acceptable salt, tautomer, or solvate thereof, wherein R$^1$ and X are as defined above for formula (1).

In some embodiments, the present disclosure is directed to an adenosine derivative having the structure of formula (1b):

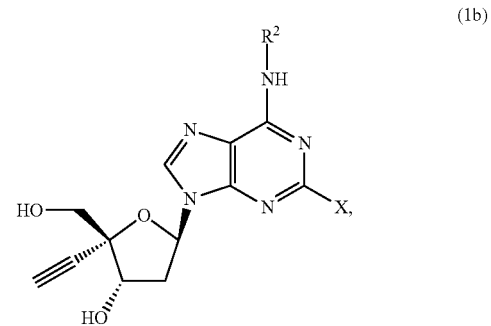

or pharmaceutically acceptable salt, tautomer, or solvate thereof, wherein R$^2$ and X are as defined above for formula (1).

In some embodiments, the adenosine derivative of the present disclosure is selected from the group consisting of:

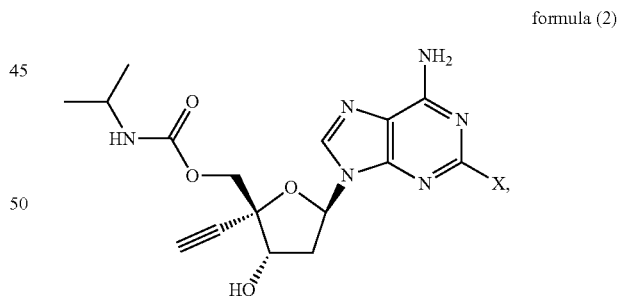

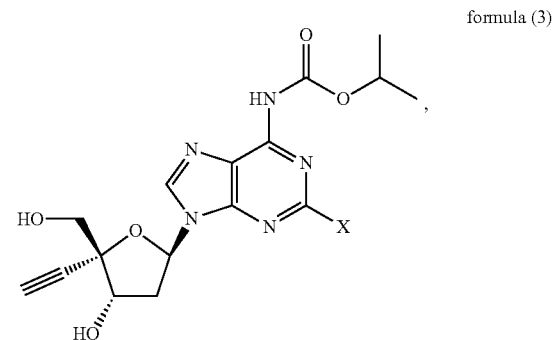

formula (4)
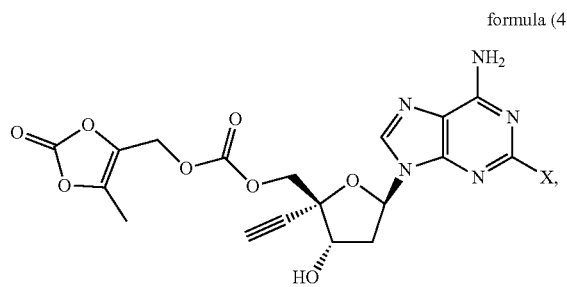
formula (5)
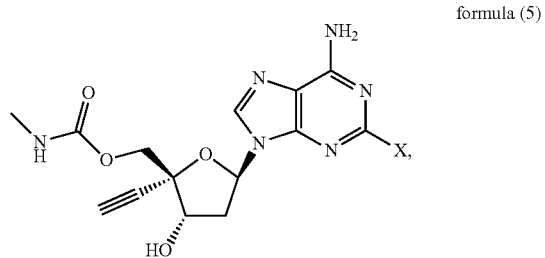
formula (6)
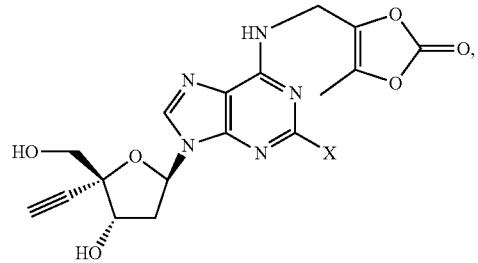
formula (7)
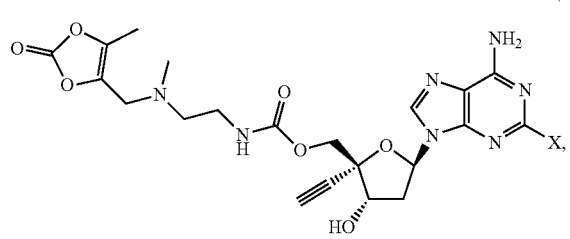
formula (8)
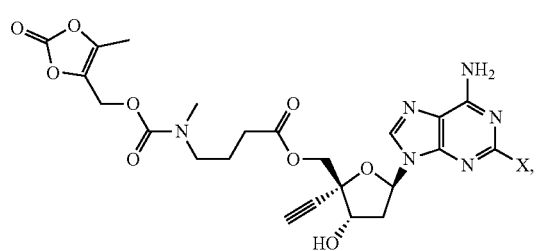
formula (4-B)
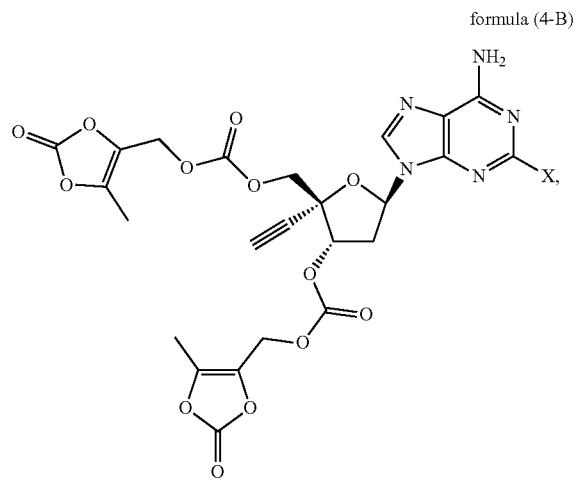
or a pharmaceutically acceptable salt, tautomer, or solvate thereof, wherein X is a described herein.
In some embodiments, X is Cl, F or Br. In some embodiments, X is F.
In further embodiments, an adenosine derivative of the present disclosure is selected from the group consisting of:
formula (2-A)
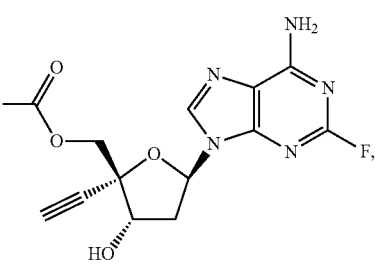
formula (3-A)
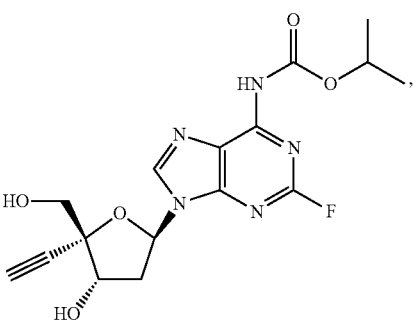
formula (4-A)
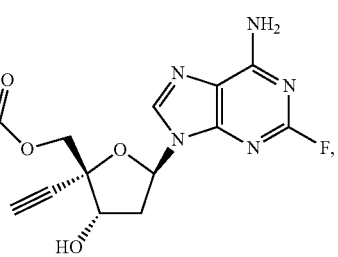

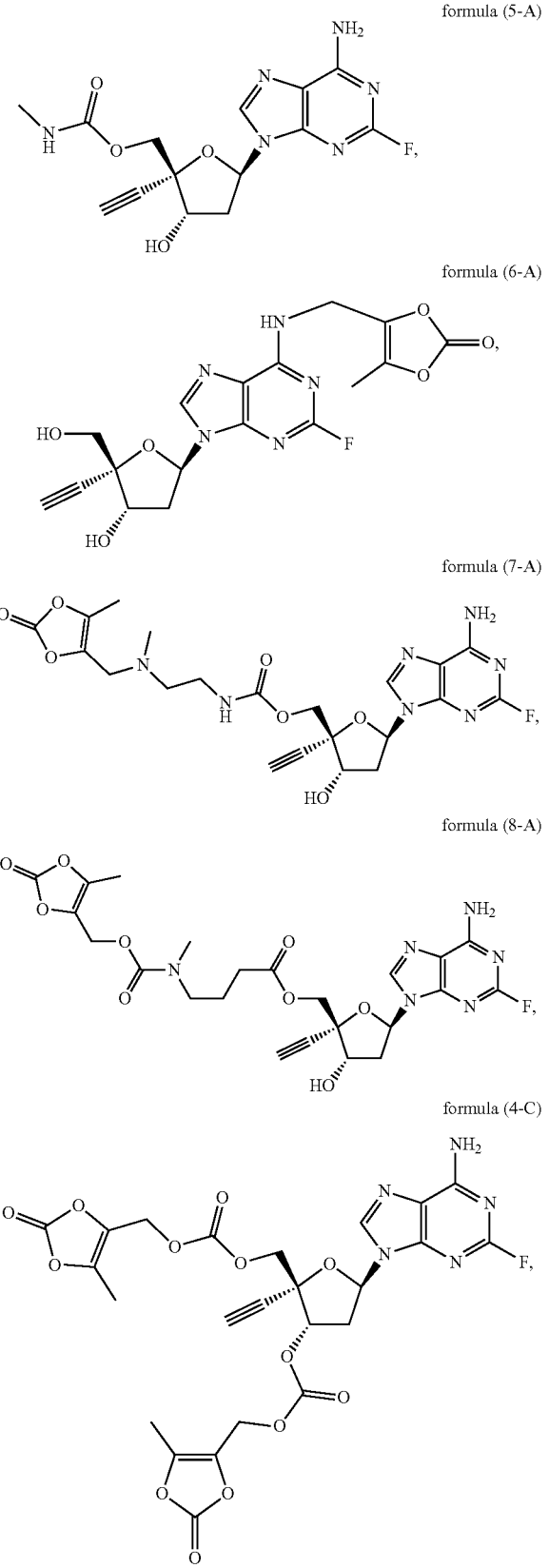

or pharmaceutically acceptable salt, tautomer, or solvate thereof.

In some embodiments, the adenosine derivative of the present disclosure is a compound selected from the group consisting of ((2R,3S,5R)-5-(6-amino-2-fluoro-9H-purin-9-yl)-2-ethynyl-3-hydroxytetrahydrofuran-2-yl)methyl isopropylcarbamate, isopropyl (9-((2R,4S,5R)-5-ethynyl-4-hydroxy-5-(hydroxymethyl)tetrahydrofuran-2-yl)-2-fluoro-9H-purin-6-yl)carbamate, ((2R,3S,5R)-5-(6-amino-2-fluoro-9H-purin-9-yl)-2-ethynyl-3-hydroxytetrahydrofuran-2-yl)methyl ((5-methyl-2-oxo-1,3-dioxol-4-yl)methyl) carbonate, ((2R,3S,5R)-5-(6-amino-2-fluoro-9H-purin-9-yl)-2-ethynyl-3-hydroxytetrahydrofuran-2-yl)methyl methylcarbamate, 4-(((9-((2R,4S,5R)-5-ethynyl-4-hydroxy-5-(hydroxymethyl)tetrahydrofuran-2-yl)-2-fluoro-9H-purin-6-yl)amino)methyl)-5-methyl-1,3-dioxol-2-one, ((2R,3S,5R)-5-(6-amino-2-fluoro-9H-purin-9-yl)-2-ethynyl-3-hydroxytetrahydrofuran-2-yl)methyl (2-(methyl((5-methyl-2-oxo-1,3-dioxol-4-yl)methyl)amino)ethyl)carbamate, [(2R,3S,5R)-5-(6-amino-2-fluoro-purin-9-yl)-2-ethynyl-3-hydroxy-tetrahydrofuran-2-yl]methyl 4-[methyl-[(5-methyl-2-oxo-1,3-dioxol-4-yl)methoxycarbonyl]amino] butanoate, and a pharmaceutically acceptable salt thereof.

In some embodiments, the adenosine derivative of the present disclosure is an isomer of formula (1)-(8), formula (1a), formula (1b), or formula (1-A)-(8-A). In some embodiments, the isomer is a stereoisomer, e.g., an enantiomer or a diastereomer. In some embodiments, the isomer is an inhibitor of reverse transcriptase having in vivo activity.

An adenosine derivative of the present disclosure can undergo conversion to a target drug and can comprise reverse transcriptase inhibitor activity in vivo, reverse transcriptase chain terminator activity in vivo, DNA translocation inhibitor activity in vivo, or a combination thereof.

An adenosine derivative of the present disclosure can be a prodrug that has no or limited activity in its original (i.e., parent) form shown herein and can be metabolized in vivo to exhibit the desired activity of a target drug, including a reverse transcriptase inhibitor activity, a reverse transcriptase chain terminator activity, DNA translocation inhibitor activity, or a combination thereof.

Not wishing to be bound by a particular mechanism or theory, Applicants discovered that the adenosine derivatives of the present disclosure can be metabolized in vivo to produce a compound or a mixture of compounds similar to or the same as a target drug 4'-ethynyl-2-fluoro-2'-deoxyadenosine (EFdA) that has reverse transcriptase inhibitor and other antiviral activities.

As disclosed herein an adenosine derivative of the present disclosure can comprise isomers (e.g., enantiomers, diastereomers, and/or tautomers) thereof, one or more pharmaceutically acceptable salts thereof, one or more solvates including hydrates thereof, solvated salts thereof or a mixture thereof.

Adenosine derivatives are also described in WO 2021/021717, which is incorporated herein by reference in its entirety.

COMPOSITIONS OF THE DISCLOSURE

The present disclosure provides pharmaceutical compositions comprising an adenosine derivative disclosed herein or pharmaceutically acceptable salt, tautomer, or solvate thereof. In some embodiments, the composition further comprises a pharmaceutically acceptable carrier.

In some embodiments, the present disclosure provides pharmaceutical compositions comprising an effective dosage of (a) a capsid (CA) inhibitor; and (b) an adenosine derivative disclosed herein or pharmaceutically acceptable salt, tautomer, or solvate thereof. In some embodiments, the composition further comprises a pharmaceutically acceptable carrier.

In some embodiments, the present disclosure provides pharmaceutical compositions comprising (1) an effective dosage of (a) a capsid (CA) inhibitor; and (b) an adenosine derivative disclosed herein or pharmaceutically acceptable salt, tautomer, or solvate thereof; and (2) a pharmaceutically acceptable carrier.

In some embodiments, the CA inhibitor is lenacapavir. Lenacapavir, as used herein, refers to a compound having the structure:

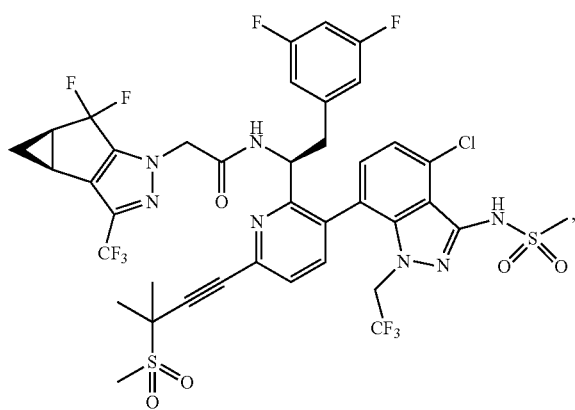 [SMILES: CC(C)(C#Cc1ccc(-c2ccc(Cl)c3c(NS(C)(=O)=O)nn(CC(F)(F)F)c23)c([C@H](Cc2cc(F)cc(F)c2)NC(=O)Cn2nc(C(F)(F)F)c3c2C(F)(F)[C@@H]2C[C@H]32)n1)S(C)(=O)=O]

a pharmaceutically acceptable salt, tautomer, or solvate thereof, or a combination thereof. Commercially available lenacapavir can be suitable is the disclosed compositions.

In some embodiments, the pharmaceutical compositions of the present disclosure comprise an effective dosage of (a) an anti-HIV agent; and (b) an adenosine derivative disclosed herein or pharmaceutically acceptable salt, tautomer, or solvate thereof. In some embodiments, the composition further comprises a pharmaceutically acceptable carrier.

In some embodiments, the anti-HIV agent is selected from the group consisting of abacavir, abacavir sulfate, lamivudine, amprenavir, atazanavir, atazanavir sulfate, AZT, bictagrevir, cabotegravir, darunavir, dideoxycytidine, dideoxyinosine, dolutegravir, doravirine, efavirenz, emtricitabine, tenofovir disoproxil fumarate, tenofovir alafenamide, 4'-ethynyl-2-fluoro-2'-deoxyadenosine, elvitegravir, etravirine, fosamprenavir calcium, indinavir, indinavir sulfate, lamivudine, lopinavir, a combination of lopinavir and ritonavir, darunavir, a combination of darunavir and cobicistat, maraviroc, nelfinavir, nelfinavir mesylate, nevirapine, PPL-100, raltegravir, rilpivirine, stavudine, tipranavir, vicriviroc, one or more capsid (CA) inhibitors, GS-6207 (lenacapavir), and combinations thereof. In some embodiments, the anti-HIV agent is a capsid (CA) inhibitor. In some embodiments, the anti-HIV agent is lenacapavir.

In some embodiments, the anti-HIV agent is a reverse transcriptase inhibitor. In some embodiments, the reverse transcriptase inhibitor is selected from the group consisting of 3'-azido-3'-deoxythymidine (AZT), 2',3'-dideoxyinosine (ddI), 2',3'-dideoxycytidine (ddC), d4T, 3TC, abacavir, emtricitabine, tenofovir disoproxil fumarate, nevirapine, delavirdine, efavirenz, rilpivirine and doravirine.

The compositions of the present disclosure can be used to treat a disease, including, but not limited to, Acquired Immune Deficiency Syndrome (AIDS), wild-type HIV-1, NRTI-resistant HIV-1, HIV-2, HIV having M184V mutations, HIV having K65R, multidrug resistant HIV, or an RNA virus infection. In some embodiments, the disease is human immunodeficiency virus 1 (HIV-1). In some embodiments, the HIV-1 is multi-drug resistant.

In some embodiments, the composition of the present disclosure comprises an adenosine derivative of formula (1):

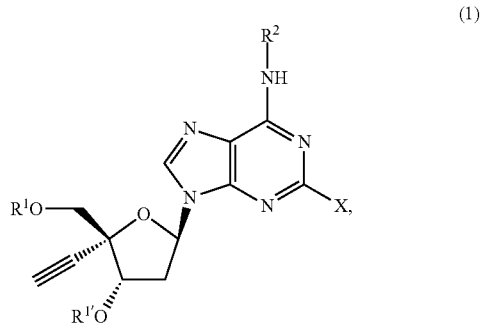

or pharmaceutically acceptable salt, tautomer, or solvate thereof,
wherein:
$R^1$, $R^{1'}$, and $R^2$ each is independently H, —C(O)N($R^3$)($R^{3'}$), —C(O)O$R^4$, —$R^5$, -$L^1$-$R^5$, or —Z-$L^4$-$R^5$, wherein at least one of $R^1$ and $R^2$ is not H;
$R^3$, $R^{3'}$ and $R^4$ each is independently H, C1-C10 alkyl, C2-C10 alkenyl, C3-C10 cycloalkyl, 3- to 10-membered heterocycloalkyl, aryl, or heteroaryl;
$R^5$ is:

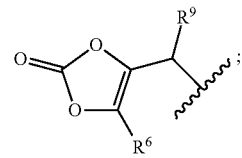

$R^6$ is H, C1-C10 alkyl, C2-C10 alkenyl, C3-C10 cycloalkyl, 3- to 10-membered heterocycloalkyl, aryl, or heteroaryl;
-$L^1$-$R^5$ is —(C1-C10 alkylene)-N($R^7$)—$R^5$, —(C1-C10 alkylene)-O—$R^5$, —(C1-C10 alkyl)-S—$R^5$, —(C2-C10 alkenylene)-N($R^7$)—$R^5$, —(C2-C10 alkenylene)-O—$R^5$, —(C2-C10 alkenylene)-S—$R^5$, —C(O)O—$R^5$, —C(O)O-$L^2$-N($R^7$)—$R^5$, —C(O)O-$L^2$-O—$R^5$, —C(O)O-$L^2$-S—$R^5$, —C(O)O-$L^2$-C(O)O—$R^5$, —C(O)O-$L^2$-C(O)N($R^7$)—$R^5$, —C(O)O-$L^2$-C(O)N($R^7$)-$L^3$-N($R^7$)—$R^5$, —C(O)O-$L^2$-C(O)N($R^7$)-$L^3$-O—$R^5$, —C(O)O-$L^2$-C(O)N($R^7$)-$L^3$-S—$R^5$, —C(O)N($R^7$)—$R^5$, —C(O)N($R^7$)-$L^2$-N($R^7$)—$R^5$, —C(O)N($R^7$)-$L^2$-O—$R^5$, —C(O)N($R^7$)-$L^2$-S—$R^5$, —C(O)N($R^7$)-$L^2$-C(O)O—$R^5$, —C(O)N($R^7$)-$L^2$-C(O)N($R^8$)—$R^5$—, —C(O)N($R^7$)-$L^2$—C(O)N($R^8$)-$L^3$-N($R^7$)—$R^5$, —C(O)O-$L^2$-N($R^7$)C(O)O—$R^5$, —C(O)N($R^8$)-$L^2$-N($R^7$)C(O)O—$R^5$, —C(O)O-$L^2$-N($R^7$)C(O)N($R^8$)—$R^5$, —C(O)N($R^7$)-$L^2$-N($R^7$)C(O)N($R^8$)—$R^5$, —C(O)N($R^7$)-$L^2$-C(O)N($R^8$)-$L^3$-O—$R^5$ or —C(O)N($R^7$)-$L^2$-C(O)N($R^8$)-$L^3$-S—$R^5$;
—Z— is —C(O)—, —C(O)O—, or —C(O)N($R^7$)—;
-$L^4$-$R^5$ is —(C1-C10 alkylene)-N($R^7$)—$R^5$, —(C1-C10 alkylene)-O—$R^5$, —(C1-C10 alkylene)-S—$R^5$, —(C2-C10 alkenylene)-N($R^7$)—$R^5$, —(C2-C10 alkenylene)-O—$R^5$ or —(C2-C10 alkenylene)-S—$R^5$;

$R^7$ and $R^8$ each is independently H, C1-C10 alkyl, or C2-C10 alkenyl;

$R^9$ is independently H, —F, C1-C10 alkyl, or C2-C10 alkenyl;

$L^2$ and $L^3$ each is divalent —(C1-C10 alkylene)-, or —(C2-C10 alkenylene)-; and X is a halogen atom.

In some embodiments of formula (1), the C1-C10 alkyl and C2-C10 alkenyl is linear or branched. In some embodiments, the adenosine derivative of the pharmaceutical compositions comprises a combination of C1-C10 alkyl, C2-C10 alkenyl, C3-C10 cycloalkyl, 3- to 10-membered heterocycloalkyl, aryl and heteroaryl.

In some embodiments, the adenosine derivative disclosed herein includes a divalent linker $L^1$ that comprises one or more repeats of a same group or a combination of different groups as disclosed herein. Non-limiting examples of the linker $L^1$ and other chemically possible combinations include those described above, e.g., in formula (1).

In some embodiments, $R^1$, $R^{1'}$, and $R^2$ each is independently $R^5$, -$L^1$-$R^5$ or —Z-$L^4$-$R^5$. In some embodiments, the structure of $R^5$, -$L^1$-$R^5$ and —Z-$L^4$-$R^5$ is:

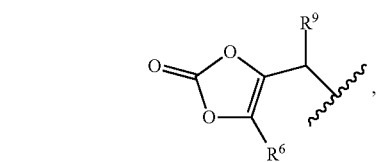
(9)

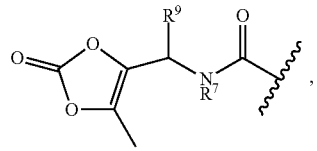
(10)

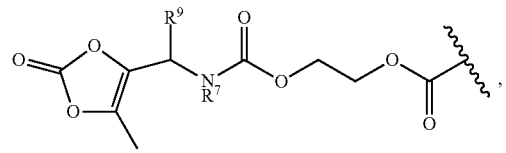
(11)

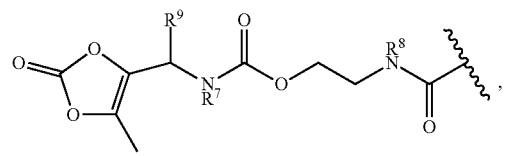
(12)

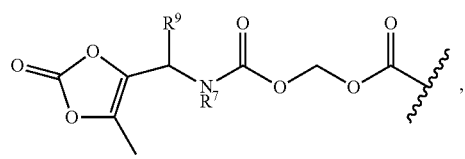
(13)

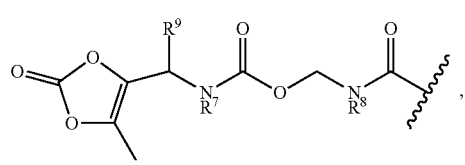
(14)

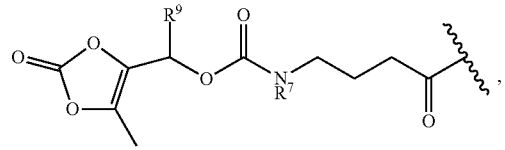
(15)

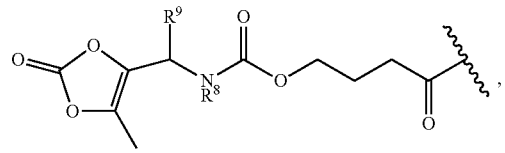
(16)

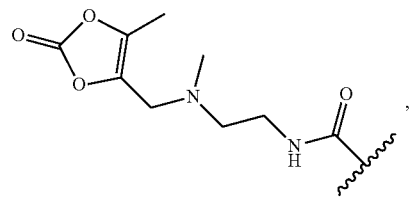
(17)

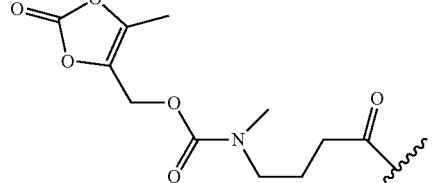
(18)

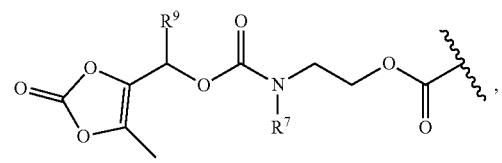
(19)

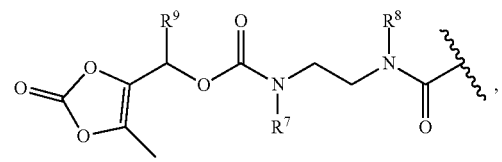
(20)

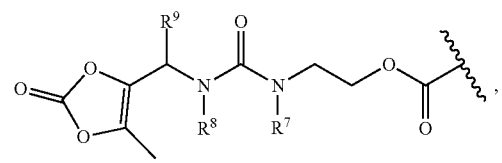
(21)

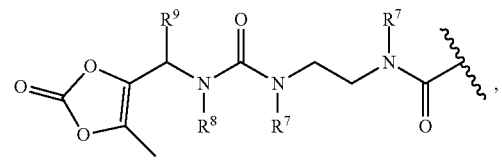
(22)

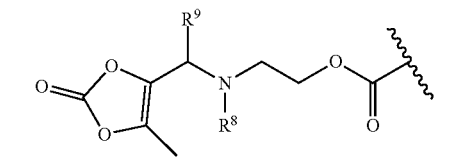
(23)

or

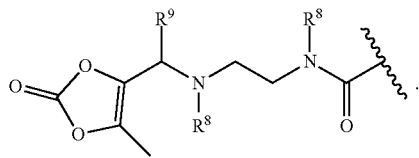

(24)

In some embodiments, a pharmaceutical composition of the present disclosure comprises an adenosine derivative disclosed herein, wherein $R^1$ and $R^{1'}$ H, —C(O)N($R^3$)($R^{3'}$) or —C(O)O$R^4$ and $R^2$ is —C(O)N($R^3$)($R^{3'}$), —C(O)O$R^4$ or one of formulas 9-24.

In some embodiments, a pharmaceutical composition of the present disclosure comprises an adenosine derivative disclosed herein, wherein $R^1$ is —C(O)N($R^3$)($R^{3'}$) or —C(O)O$R^4$ and $R^2$ is H, —C(O)N($R^3$)($R^{3'}$), —C(O)O$R^4$ or one of formulas 9-24.

In some embodiments, a pharmaceutical composition of the present disclosure comprises an adenosine derivative disclosed herein, wherein $R^2$ is H, —C(O)N($R^3$)($R^{3'}$) or —C(O)O$R^4$ and $R^1$ is —C(O)N($R^3$)($R^{3'}$) or —C(O)O$R^4$ or one of formulas 9-24.

In some embodiments, a pharmaceutical composition of the present disclosure comprises an adenosine derivative disclosed herein, wherein $R^2$ is —C(O)N($R^3$)($R^{3'}$) or —C(O)O$R^4$ and $R^1$ and $R^{1'}$ is each independently H, —C(O)N($R^3$)($R^{3'}$), —C(O)O$R^4$ or one of formulas 9-24.

In some embodiments, a pharmaceutical composition of the present disclosure comprises an adenosine derivative disclosed herein, wherein $R^1$ and $R^{1'}$ each is independently H, —C(O)N($R^3$)($R^{3'}$), —C(O)O$R^4$, —$R^5$, -$L^1$-$R^5$, —Z-$L^4$-$R^5$ or one of one of formulas 9-24 and $R^2$ is —C(O)N($R^3$)($R^{3'}$), —C(O)O$R^4$, —$R^5$, -$L^1$-$R^5$, —Z-$L^4$-$R^5$ or one of formulas 9-24.

In some embodiments, a pharmaceutical composition of the present disclosure comprises an adenosine derivative disclosed herein, wherein $R^1$ is —C(O)N($R^3$)($R^{3'}$), —C(O)O$R^4$, —$R^5$, -$L^1$-$R^5$, —Z-$L^4$-$R^5$ or one of one of formulas 9-24 and $R^2$ is H, —C(O)N($R^3$)($R^{3'}$), —C(O)O$R^4$, —$R^5$, -$L^1$-$R^5$, —Z-$L^4$-$R^5$ or one of formulas 9-24.

In some embodiments, a pharmaceutical composition of the present disclosure comprises an adenosine derivative disclosed herein, wherein $R^1$, $R^{1'}$, and $R^2$ each is independently selected from one of formulas 9-24.

In some embodiments, $R^3$, $R^{3'}$ and $R^4$ each is independently H, C1-C10 alkyl, C2-C10 alkenyl, or C3-C10 cycloalkyl. In some embodiments, $R^3$, $R^{3'}$ and $R^4$ each is independently H, C1-C5 alkyl, C2-C5 alkenyl, or C3-C6 cycloalkyl. In some embodiments, $R^3$, $R^{3'}$ and $R^4$ each is independently H or C1-C5 alkyl. In some embodiments, the C1-C5 alkyl is methyl, ethyl, or isopropyl. In some embodiments, $R^3$, $R^{3'}$ and $R^4$ each is independently H, methyl, or isopropyl.

In some embodiments, $R^6$ is H, C1-C5 alkyl, C2-C4 alkenyl, C3-C6 cycloalkyl, 3- to 6-membered heterocycloalkyl, phenyl, or 5- to 6-membered heteroaryl. In some embodiments, $R^6$ is H, C1-C10 alkyl, C2-C10 alkenyl, or C3-C10 cycloalkyl. In some embodiments, $R^6$ is H, C1-C5 alkyl, C2-C5 alkenyl, or C3-C6 cycloalkyl. In some embodiments, $R^6$ is H, C1-C3 alkyl, or C2-C4 alkenyl. In some embodiments, $R^6$ is C1-C10 alkyl. In some embodiments, $R^6$ is C1-C5 alkyl. In some embodiments, $R^6$ is C1-C3 alkyl. In some embodiments, $R^6$ is selected from the group consisting of H, methyl, ethyl, isopropyl, and cyclopropyl. In some embodiments, $R^6$ is methyl, ethyl, or isopropyl. In some embodiments, $R^6$ is methyl. In some embodiments, $R^6$ is isopropyl.

In some embodiments, $R^7$ and $R^8$ each is independently H, C1-C10 alkyl, or C3-C6 cycloalkyl. In some embodiments, $R^7$ and $R^8$ each is independently H, C1-C5 alkyl, or C3-C6 cycloalkyl. In some embodiments, $R^7$ and $R^8$ each is independently H or C1-C5 alkyl. In some embodiments, the C1-C5 alkyl is methyl, ethyl, or isopropyl. In some embodiments, the C3-C6 cycloalkyl is cyclopropyl. In some embodiments, $R^7$ and $R^8$ each is independently H, methyl, ethyl, isopropyl, or cyclopropyl.

In some embodiments, $R^7$ is H or C1-C10 alkyl. In some embodiments, $R^7$ is H or C1-C5 alkyl. In some embodiments, the C1-C5 alkyl is methyl, ethyl, or isopropyl. In some embodiments, $R^7$ is H or Me. In some embodiments, $R^7$ is H.

In some embodiments, $R^8$ is H or C1-C10 alkyl. In some embodiments, $R^8$ is H or C1-C5 alkyl. In some embodiments, $R^8$ is H or Me. In some embodiments, $R^8$ is H.

In some embodiments, $R^9$ is H, F, C1-C10 alkyl, or C2-C10 alkenyl. In some embodiments $R^9$ is H, F, C1-C5 alkyl, or C2-C5 alkenyl. In some embodiments, $R^9$ is H, F, or C1-C5 alkyl. In some embodiments, $R^9$ is H, F, or C1-C3 alkyl. In some embodiments, $R^9$ is H or C1-C3 alkyl. In some embodiments, $R^9$ is C1-C3 alkyl. In some embodiments, $R^9$ is H, F, or Me. In some embodiments, $R^9$ is H, F, Me, or isopropyl. In some embodiments, $R^9$ is H or Me. In some embodiments, $R^9$ is H or F. In some embodiments, $R^9$ is H.

In some embodiments, X is a halogen atom selected from the group consisting of fluorine, chlorine, bromine and iodine (alternatively referred to as fluoro (F), chloro (Cl), bromo (Br), and iodo (I)). In one embodiment, X is F. In another embodiment, X is Cl. In yet another embodiment, X is Br. Non-limiting examples of adenosine derivatives of the present disclosure are provided herein.

In some embodiments, the composition of the present disclosure comprises an adenosine derivative of formula (1a):

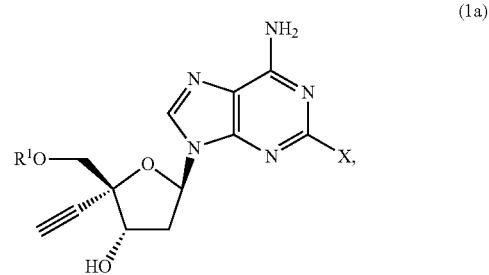

(1a)

or pharmaceutically acceptable salt, tautomer, or solvate thereof, wherein $R^1$ and X are as defined above for formula (1).

In some embodiments, the composition of the present disclosure comprises an adenosine derivative of formula (1b):

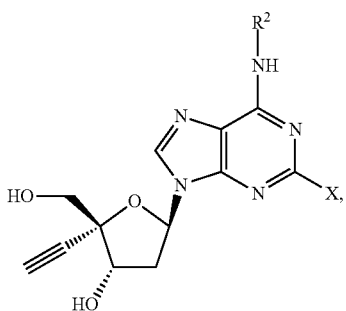
(1b)

or pharmaceutically acceptable salt, tautomer, or solvate thereof, wherein $R^2$ and X are as defined above for formula (1).

In some embodiments, the pharmaceutical composition of the present disclosure comprises an adenosine derivative having a formula selected from the group consisting of:

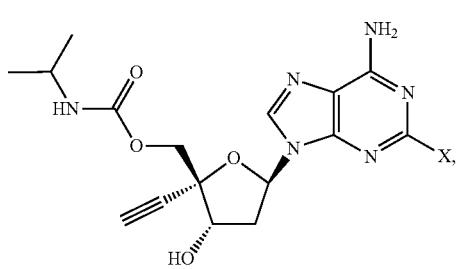
formula (2)

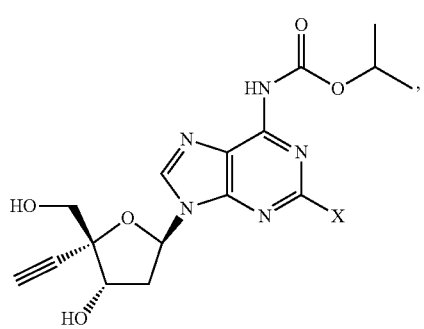
formula (3)

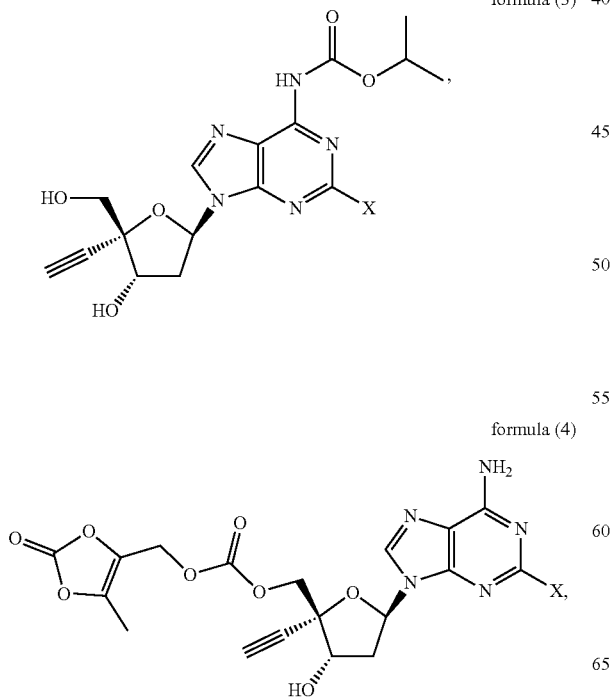
formula (4)

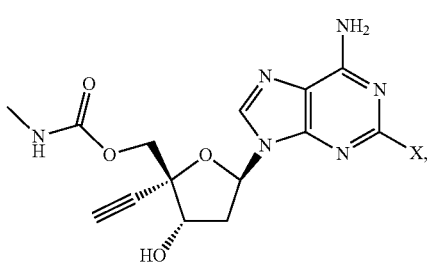
formula (5)

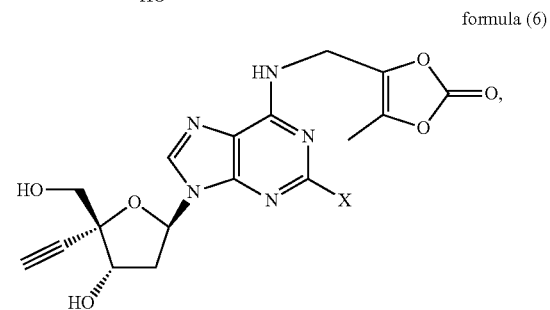
formula (6)

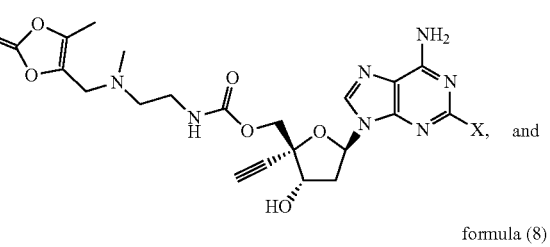
formula (7)

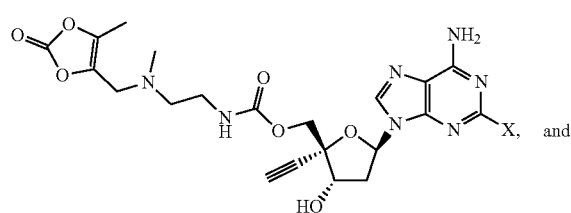
formula (8)

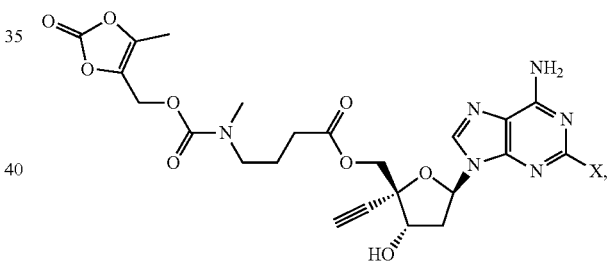
formula (4-B)

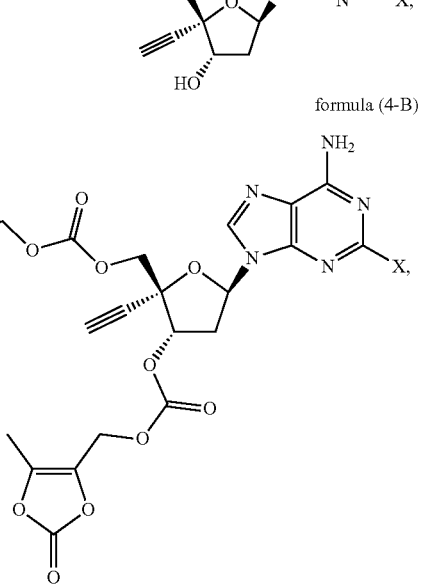

or a pharmaceutically acceptable salt, tautomer, solvate, or a combination thereof.

In some embodiments, X is Cl, F or Br. In some embodiments, X is F.

In some embodiments, the pharmaceutical composition of the present disclosure comprises an adenosine derivative having a formula selected from the group consisting of:

formula (2-A)

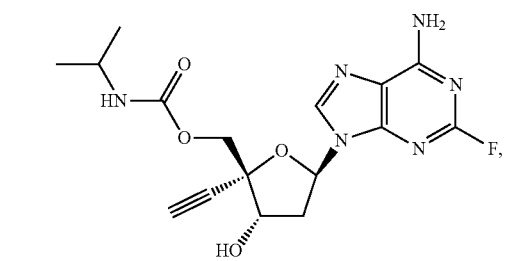

formula (3-A)

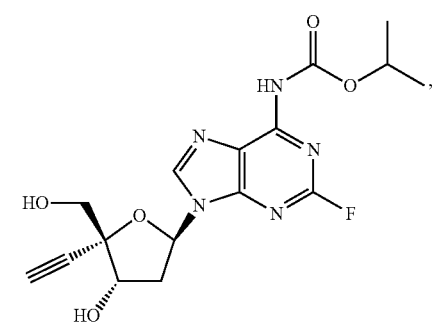

formula (4-A)

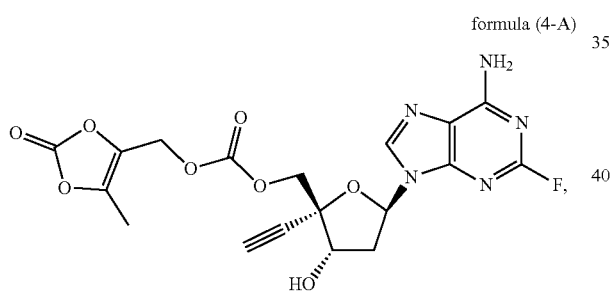

formula (5-A)

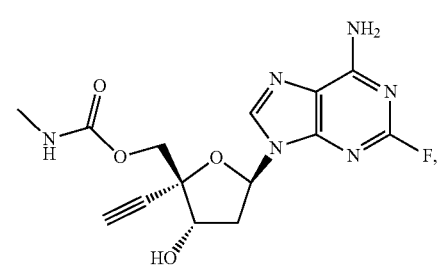

formula (6-A)

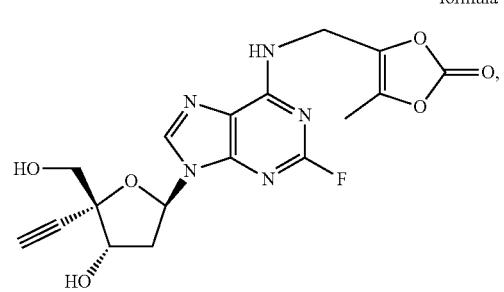

formula (7-A)

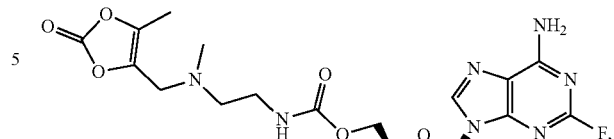

formula (8-A)

formula (4-C)

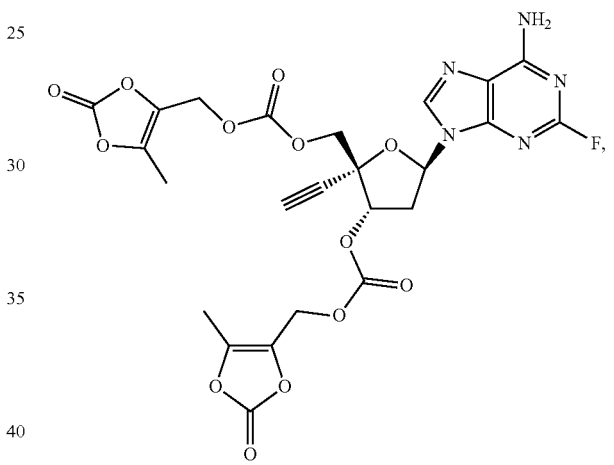

a stereoisomer thereof, a pharmaceutically acceptable salt thereof, or a combination thereof.

In some embodiments, the adenosine derivative of the pharmaceutical composition is a compound of formula (1)-(8), formula (1a), formula (1b), formula (1-A)-(8-A), formula (4-B), or formula (4-C).

In some embodiments, the adenosine derivative of the pharmaceutical composition is an isomer of formula (1)-(8), formula (1a), formula (1b), formula (1-A)-(8-A), formula (4-B), or formula (4-C). Isomers described above, such as tautomers, enantiomers, diastereomers, cis/trans isomers or a combination thereof can be suitable. In some embodiments, the isomer is a stereoisomer, e.g., an enantiomer or a diastereomer. In some embodiments, the isomer is an inhibitor of reverse transcriptase having in vivo activity.

As disclosed herein, the pharmaceutical composition of the present disclosure can comprise an adenosine derivative selected from the group consisting of: ((2R,3S,5R)-5-(6-amino-2-fluoro-9H-purin-9-yl)-2-ethynyl-3-hydroxytetrahydrofuran-2-yl)methyl isopropylcarbamate, isopropyl (9-((2R,4S,5R)-5-ethynyl-4-hydroxy-5-(hydroxymethyl) tetrahydrofuran-2-yl)-2-fluoro-9H-purin-6-yl)carbamate, ((2R,3S,5R)-5-(6-amino-2-fluoro-9H-purin-9-yl)-2-ethynyl-3-hydroxytetrahydrofuran-2-yl)methyl ((5-methyl-2- oxo-1,3-dioxol-4-yl)methyl) carbonate, ((2R,3S,5R)-5-(6-amino-2-fluoro-9H-purin-9-yl)-2-ethynyl-3-hydroxytetrahydrofuran-2-yl)methyl methylcarbamate, 4-(((9-((2R,4S,5R)-5-ethynyl-4-hydroxy-5-(hydroxymethyl)tetrahydrofuran-2-yl)-2-fluoro-9H-purin-6-yl)amino)methyl)-5-methyl-1,3-dioxol-2-one, ((2R,3S,5R)-5-(6-amino-2-fluoro-9H-purin-9-yl)-2-ethynyl-3-hydroxytetrahydrofuran-2-yl)methyl (2-(methyl((5-methyl-2-oxo-1,3-dioxol-4-yl)methyl)amino)ethyl)carbamate, [(2R,3S,5R)-5-(6-amino-2-fluoro-purin-9-yl)-2-ethynyl-3-hydroxy-tetrahydrofuran-2-yl]methyl 4-[methyl-[(5-methyl-2-oxo-1,3-dioxol-4-yl)methoxycarbonyl]amino]butanoate, and pharmaceutically acceptable salts thereof.

As disclosed above, a pharmaceutical composition of the present disclosure comprising an adenosine derivative can be free from monophosphate group, diphosphate group, tri-phosphate group or a combination thereof. In some embodiments, an $R^1$ and/or $R^2$ group of an adenosine derivative of disclosed herein is free from monophosphate group, diphosphate group, tri-phosphate group or a combination thereof.

In some embodiments, the pharmaceutical composition of the present disclosure comprises 10 mg to 2000 mg, e.g., about 10 mg, about 25 mg, about 50 mg, about 75 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, or about 2000 mg of an adenosine derivative disclosed herein or a pharmaceutically acceptable salt, tautomer, or solvate thereof, including all ranges and values therebetween. In some embodiments, the pharmaceutical composition of the present disclosure comprises 100 mg to 2000 mg, 100 mg to 1900 mg, 100 mg to 1800 mg, 100 mg to 1700 mg, 100 mg to 1600 mg, 100 mg to 1500 mg, 100 mg to 1400 mg, 100 mg to 1300 mg, 100 mg to 1200 mg, 100 mg to 1100 mg, 100 mg to 1000 mg, 100 mg to 900 mg, 100 mg to 800 mg, 100 mg to 700 mg, 100 mg to 600 mg, 100 mg to 500 mg, 100 mg to 400 mg or 100 mg to 300 mg, 200 mg to 1000 mg, 300 mg to 1000 mg, 400 mg to 1000 mg, 500 mg to 1000 mg, 600 mg to 1000 mg, 700 mg to 1000 mg, 800 mg to 1000 mg, 900 mg to 1000 mg, 200 mg to 1200 mg, 300 mg to 1200 mg, 400 mg to 1200 mg, 500 mg to 1200 mg, 600 mg to 1200 mg, 700 mg to 1200 mg, 800 mg to 1200 mg, 900 mg to 1200 mg, 1000 mg to 1200, 200 mg to 2000 mg, 300 mg to 2000 mg, 400 mg to 2000 mg, 500 mg to 2000 mg, 600 mg to 2000 mg, 700 mg to 2000 mg, 800 mg to 2000 mg, 900 mg to 2000 mg, or 1000 mg to 2000 of an adenosine derivative disclosed herein or a pharmaceutically acceptable salt, tautomer, or solvate thereof. In some embodiments, the pharmaceutical composition comprises 700 mg to 2000 mg of an adenosine derivative disclosed herein or a pharmaceutically acceptable salt, tautomer, or solvate thereof. In some embodiments, the pharmaceutical composition comprises 700 mg to 1200 mg of an adenosine derivative disclosed herein or a pharmaceutically acceptable salt, tautomer, or solvate thereof.

In some embodiments, the pharmaceutical composition of the present disclosure comprises 10 mg to 2000 mg, e.g., about 10 mg, about 25 mg, about 50 mg, about 75 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, or about 2000 mg of an anti-HIV agent, including all ranges and values therebetween. In some embodiments, the pharmaceutical composition comprises 100 mg to 2000 mg, 100 mg to 1800 mg, 100 mg to 1600 mg, 100 mg to 1500 mg, 100 mg to 1400 mg, 100 mg to 1200 mg, 100 mg to 1100 mg, 100 mg to 1000 mg, 100 mg to 900 mg, 100 mg to 800 mg, 100 mg to 700 mg, 100 mg to 600 mg, 100 mg to 500 mg, 100 mg to 400 mg or 100 mg to 300 mg, 200 mg to 1200 mg, 300 mg to 1200 mg, 400 mg to 1200 mg, 500 mg to 1200 mg, 600 mg to 1200 mg, 700 mg to 1200 mg, 800 mg to 1200 mg, 900 mg to 1200 mg, 1000 mg to 1200, 1000 mg to 2000 mg of an anti-HIV agent. In some embodiments, the pharmaceutical composition comprises 700 mg to 1000 mg of the anti-HIV agent.

In some embodiments, the pharmaceutical composition of the present disclosure comprises 10 mg to 2000 mg, e.g., about 10 mg, about 25 mg, about 50 mg, about 75 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, or about 2000 mg of a CA inhibitor, e.g., lenacapavir. In some embodiments, the pharmaceutical composition comprises 100 mg to 2000 mg, 100 mg to 1800 mg, 100 mg to 1600 mg, 100 mg to 1500 mg, 100 mg to 1400 mg, 100 mg to 1200 mg, 100 mg to 1100 mg, 100 mg to 1000 mg, 100 mg to 900 mg, 100 mg to 800 mg, 100 mg to 700 mg, 100 mg to 600 mg, 100 mg to 500 mg, 100 mg to 400 mg or 100 mg to 300 mg, 200 mg to 1200 mg, 300 mg to 1200 mg, 400 mg to 1200 mg, 500 mg to 1200 mg, 600 mg to 1200 mg, 700 mg to 1200 mg, 800 mg to 1200 mg, 900 mg to 1200 mg, 1000 mg to 1200, 1000 mg to 2000 mg of a CA inhibitor, e.g., lenacapavir. In some embodiments, the pharmaceutical composition comprises 700 mg to 1000 mg of the CA inhibitor.

The pharmaceutical compositions of the present disclosure can further comprise a pharmaceutically acceptable carrier.

Non-limiting examples of pharmaceutically acceptable carriers include a pharmaceutical excipients surfactant, emulsifier, filler, carrier, isotonicifier, dispersing agent, viscosity modifier, resuspending agent, buffer or a combination thereof. Pharmaceutical excipients typically do not have properties of a medicinal or drug active ingredient, also known as active pharmaceutical ingredient (API) and are typically used to streamline the manufacture process or packaging of the active ingredients, or to deliver an API to a patient or other subject. Pharmaceutical acceptable carrier, excipients or inactive ingredients from the Inactive Ingredients Database available from US FDA (https://www.fda.gov/drugs/drug-approvals-and-databases/inactive-ingredients-database-download) can be suitable. Some of Generally Recognized As Safe (GRAS) food substances available form US FDA's GRAS Substances (SCOGS) Database (https://www.fda.gov/food/generally-recognized-safe-gras/gras-substances-scogs-database) can also be suitable.

In some embodiments of the present disclosure, the pharmaceutical acceptable carrier comprises acacia, animal oils, benzyl alcohol, benzyl benzoate, calcium stearate, carbomers, cetostearyl alcohol, cetyl alcohol, cholesterol, cyclodextrins, dextrose, diethanolamine, emulsifying wax, ethylene glycol palmitostearate, glycerin, glycerin monostearate, glycerol stearate, glyceryl monooleate, glyceryl monostearate, hydrous, histidine, hydrochloric acid, hydroxpropyl cellulose, hydroxypropyl-o-cyclodextrin (HPBCD), hypromellose (hydroxypropyl methylcellulose (HPMC)), lanolin, lanolin alcohols, lecithin, medium-chain triglycerides, metallic soaps, methylcellulose, mineral oil, monobasic sodium phosphate, monoethanolamine, oleic acid, polyyethylene glycols (PEG 3350, PEG 4000, PEG 6000), polyoxyethylene-polyoxypropylene copolymer (poloxamer), polyoxyethylene alkyl ethers, polyoxyethylene castor oil, polyoxyethylene castor oil derivatives, polyoxyethylene sorbitan fatty acid esters, polyoxyethylene stearates, polysorbate, polyoxyethylene (20) sorbitan monolaurate (Tween 20, Polysorbate 20), polyoxyethylene (20) sorbitan monooleate (Tween 80, Polysorbate 80), povidone, propylene glycol alginate, saline, sodium chloride, sodium citrate, sodium citrate dihydrate, sodium hydroxide, sodium lauryl sulfate, sodium phosphate monobasic, sodium phosphate dibasic, sorbitan esters, stearic acid, stearyl alcohol, sunflower oil, tragacanth, triethanolamine, vegetable oils, water, xanthan gum, or combinations thereof.

In further embodiments, the pharmaceutical acceptable carrier comprises dextrose, glycerin, histidine, hydrochloric acid, hydroxpropyl cellulose, hydroxypropyl-o-cyclodextrin (HPBCD), hypromellose (hydroxypropyl methylcellulose (HPMC)), polyoxyethylene (20) sorbitan monolaurate (Tween 20, Polysorbate 20), polyyethylene glycols (PEG 400, PEG 3350, PEG 4000, PEG 6000), polyoxyethylene-polyoxypropylene copolymer (Poloxamer 188, Poloxamer 407), polyoxyethylene (20) sorbitan monooleate (Tween 80, Polysorbate 80), saline, sodium chloride, sodium citrate, sodium citrate dihydrate, sodium lauryl sulfate, sodium phosphate monobasic, sodium phosphate dibasic, or a combination thereof.

In some embodiments, the adenosine derivative, e.g., a compound of formula (1)-(8), formula (1a), formula (1b), or formula (1-A)-(8-A), and the anti-HIV agent, e.g., a CA inhibitor, are combined in a single formulation that can be administered to a subject. In some embodiments, the adenosine derivative and the anti-HIV agent, e.g., a CA inhibitor, are provided in separate formulations that can be administered to a subject simultaneously or sequentially. The pharmaceutical compositions of the present disclosure can also be administered with one or more additional anti-HIV agents, in separate formulations that can be administered to a subject simultaneously.

In some embodiments, the adenosine derivative of the present disclosure is administered to a subject concurrently with, prior to, or after a CA inhibitor. In some embodiments, the adenosine derivative and the CA inhibitor are each administered periodically to a subject.

The pharmaceutical compositions of the present disclosure are suitable for oral, intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, the pharmaceutical composition can be administered via a non-parenteral route, such as a topical, epidermal or mucosal route of administration, e.g., intranasally, orally, vaginally, rectally, sublingually or topically. The pharmaceutical compositions can be in the form of sterile aqueous solutions or dispersions. The pharmaceutical compositions can also be formulated in a microemulsion, liposome, or other ordered structure suitable to high drug concentration.

METHODS OF THE DISCLOSURE

In some embodiments, the present disclosure provides methods of treating or preventing an HIV infection, comprising administering to a subject in need thereof an effective dosage of (a) an anti-HIV agent; and (b) an adenosine derivative disclosed herein, composition thereof, or pharmaceutically acceptable salt, tautomer, or solvate thereof.

In some embodiments, the present disclosure provides methods of treating an HIV infection, comprising administering to a subject in need thereof an effective dosage of (a) an anti-HIV agent; and (b) an adenosine derivative disclosed herein, composition thereof, or pharmaceutically acceptable salt, tautomer, or solvate thereof.

In some embodiments of the disclosed methods, the anti-HIV agent is selected from the group consisting of abacavir, abacavir sulfate, lamivudine, amprenavir, atazanavir, atazanavir sulfate, AZT, bictagrevir, cabotegravir, darunavir, dideoxycytidine, dideoxyinosine, dolutegravir, doravirine, efavirenz, emtricitabine, tenofovir disoproxil fumarate, tenofovir alafenamide, 4'-ethynyl-2-fluoro-2'-deoxyadenosine, elvitegravir, etravirine, fosamprenavir calcium, indinavir, indinavir sulfate, lamivudine, lopinavir, a combination of lopinavir and ritonavir, darunavir, a combination of darunavir and cobicistat, maraviroc, nelfinavir, nelfinavir mesylate, nevirapine, PPL-100, raltegravir, rilpivirine, stavudine, tipranavir, vicriviroc, one or more capsid (CA) inhibitors, and GS-6207 (lenacapavir), or a combination thereof. In some embodiments, the anti-HIV agent is a capsid (CA) inhibitor. Capsid inhibitors (also referred to as HIV-1 capsid inhibitors) are disclosed in WO2018/0145021, which is incorporated by reference herein in its entirety for all purposes. In some embodiments, the capsid inhibitor is a capsid polymerization inhibitor or a capsid disrupting compound, an HIV nucleocapsid p7 (NCp7) inhibitor, or an HIV p24 capsid protein inhibitor. In some embodiments, the CA inhibitor is lenacapavir. In some embodiments, the anti-HIV agent is lenacapavir.

Lenacapavir, as used herein, refers to a compound having the structure:

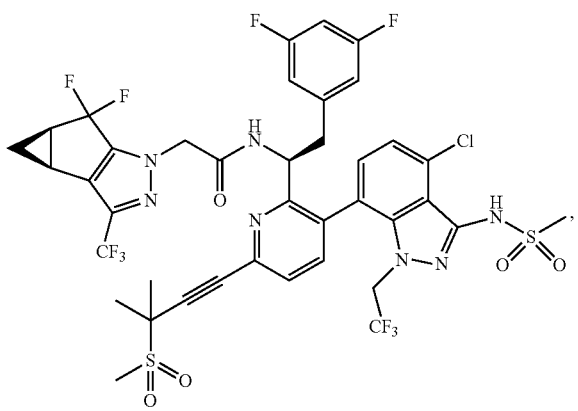 [SMILES: CC(C)(C#Cc1ccc(-c2ccc(Cl)c3c(NS(C)(=O)=O)nn(CC(F)(F)F)c23)c([C@H](Cc2cc(F)cc(F)c2)NC(=O)Cn2nc(C(F)(F)F)c3c2C(F)(F)[C@@H]2C[C@H]32)n1)S(C)(=O)=O]

or a pharmaceutically acceptable salt, tautomer, or solvate thereof. Commercially available lenacapavir can be suitable in the disclosed methods.

In some embodiments, the present disclosure provides methods of treating or preventing an HIV infection, comprising administering to a subject in need thereof an effective dosage of (a) a capsid (CA) inhibitor; and (b) an adenosine derivative disclosed herein, composition thereof, or pharmaceutically acceptable salt, tautomer, or solvate thereof. In some embodiments, the capsid inhibitor is lenacapavir.

In some embodiments, the present disclosure provides methods of treating an HIV infection, comprising administering to a subject in need thereof an effective dosage of (a) a capsid (CA) inhibitor; and (b) an adenosine derivative disclosed herein, composition thereof, or pharmaceutically acceptable salt, tautomer, or solvate thereof. In some embodiments, the capsid inhibitor is lenacapavir.

In some embodiments, the capsid (CA) inhibitor, such as the above mentioned lenacapavir, is administered to the subject in a dosage (effective dosage) of 100 mg to 2000 mg, 100 mg to 1800 mg, 100 mg to 1600 mg, 100 mg to 1500 mg, 100 mg to 1400 mg, 100 mg to 1200 mg, 100 mg to 1100 mg, 100 mg to 1000 mg, 100 mg to 900 mg, 100 mg to 800 mg, 100 mg to 700 mg, 100 mg to 600 mg, 100 mg to 500 mg, 100 mg to 400 mg or 100 mg to 300 mg, 200 mg to 1200 mg, 300 mg to 1200 mg, 400 mg to 1200 mg, 500 mg to 1200 mg, 600 mg to 1200 mg, 700 mg to 1200 mg, 800 mg to 1200 mg, 900 mg to 1200 mg, 1000 mg to 1200, 1000 mg to 2000 mg. In some embodiments, the CA inhibitor is administered to the subject in an effective dosage ranging from 700 mg to 1000 mg using one of the administration schedules described above and hereafter. In some embodiments, the CA inhibitor is administered to the subject in a single dosage ranging from 100 mg to 2000 mg every 6 month. The CA inhibitor can be administered to the subject via one or more injections.

In some embodiments, an effective dosage of the capsid (CA) inhibitor, such as the above mentioned lenacapavir, administered to the subject ranges from 100 mg to 2000 mg every 1 to 7 days to about once every 8 weeks. In some embodiments, the effective dosage of the CA inhibitor is 300 mg daily, once every two days, once every 3 days, once every 4 days, once every 5 days, once every 6 days, once every 7 days, once every week (QW), once every two weeks (Q2W), once every 3 weeks (Q3W), once every 4 weeks (Q4W), once every 5 weeks (Q5W), once every 6 weeks (Q6W), once every 7 weeks (Q7W) or once every 8 weeks (Q8W). In some embodiments, the effective dosage of the CA inhibitor is 400 mg daily, once every two days, once every 3 days, once every 4 days, once every 5 days, once every 6 days, once every 7 days, once every week (QW), once every two weeks (Q2W), once every 3 weeks (Q3W), once every 4 weeks (Q4W), once every 5 weeks (Q5W), once every 6 weeks (Q6W), once every 7 weeks (Q7W) or once every 8 weeks (Q8W). In some embodiments, the effective dosage of the CA inhibitor is 500 mg daily, once every two days, once every 3 days, once every 4 days, once every 5 days, once every 6 days, once every 7 days, once every week (QW), once every two weeks (Q2W), once every 3 weeks (Q3W), once every 4 weeks (Q4W), once every 5 weeks (Q5W), once every 6 weeks (Q6W), once every 7 weeks (Q7W) or once every 8 weeks (Q8W). In some embodiments, the effective dosage of the CA inhibitor is 600 mg daily, once every two days, once every 3 days, once every 4 days, once every 5 days, once every 6 days, once every 7 days, once every week (QW), once every two weeks (Q2W), once every 3 weeks (Q3W), once every 4 weeks (Q4W), once every 5 weeks (Q5W), once every 6 weeks (Q6W), once every 7 weeks (Q7W) or once every 8 weeks (Q8W). In some embodiments, the effective dosage of the CA inhibitor is 800 mg daily, once every two days, once every 3 days, once every 4 days, once every 5 days, once every 6 days, once every 7 days, once every week (QW), once every two weeks (Q2W), once every 3 weeks (Q3W), once every 4 weeks (Q4W), once every 5 weeks (Q5W), once every 6 weeks (Q6W), once every 7 weeks (Q7W) or once every 8 weeks (Q8W). In some embodiments, the effective dosage of the CA inhibitor is 900 mg daily, once every two days, once every 3 days, once every 4 days, once every 5 days, once every 6 days, once every 7 days, once every week (QW), once every two weeks (Q2W), once every 3 weeks (Q3W), once every 4 weeks (Q4W), once every 5 weeks (Q5W), once every 6 weeks (Q6W), once every 7 weeks (Q7W) or once every 8 weeks (Q8W). In some embodiments, the effective dosage of the CA inhibitor is 1000 mg daily, once every two days, once every 3 days, once every 4 days, once every 5 days, once every 6 days, once every 7 days, once every week (QW), once every two weeks (Q2W), once every 3 weeks (Q3W), once every 4 weeks (Q4W), once every 5 weeks (Q5W), once every 6 weeks (Q6W), once every 7 weeks (Q7W) or once every 8 weeks (Q8W). In some embodiments, the effective dosage of the CA inhibitor ranges from 700 mg to 2000 mg once every month (QM). In some embodiments, the effective dosage of the CA inhibitor ranges from 700 mg to 2000 mg once every month (QM). The CA inhibitor can be administered to the subject orally with or without food. The CA inhibitor can also be administered to the subject via injections, such as in the abdomen via subcutaneous injections.

In some embodiments, the lenacapavir is administered orally to the subject. In some embodiments, the lenacapavir is administered orally to the subject at a dose of 100 mg to 1000 mg per day. In some embodiments, the lenacapavir is administered orally at a dose of 300 mg to 600 mg per day. In some embodiments, the lenacapavir is administered orally at a dose of 300 mg or 600 mg per day.

In some embodiments, the lenacapavir is dosed by injection subcutaneously. In some embodiments, the lenacapavir is administered subcutaneously. In some embodiments, the lenacapavir is administered subcutaneously at a dose of 500 mg to 1500 mg per day. In some embodiments, the lenacapavir is administered subcutaneously at a dose of 800 mg to 100 mg per day. In some embodiments, the lenacapavir is administered subcutaneously at a dose of 927 mg per day.

The adenosine derivative suitable for use in the disclosed methods can be any adenosine derivative, pharmaceutically acceptable salt, tautomer, or solvate thereof disclosed herein.

In some embodiments, the adenosine derivative for use in the disclosed methods is a compound of formula (1):

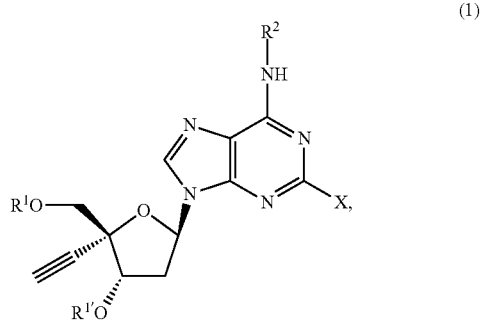

(1)

or pharmaceutically acceptable salt, tautomer, or solvate thereof, wherein:

R[1], R[1'], and R[2] each is independently H, —C(O)N(R[3])(R[3']), —C(O)OR[4], —R[5], -L[1]-R[5], or —Z-L[4]-R[5], wherein at least one of R[1] and R[2] is not H;

R[3], R[3'] and R[4] each is independently H, C1-C10 alkyl, C2-C10 alkenyl, C3-C10 cycloalkyl, 3- to 10-membered heterocycloalkyl, aryl, or heteroaryl;

R[5] is:

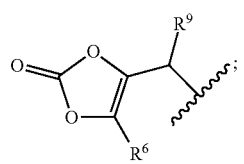

R[6] is H, C1-C10 alkyl, C2-C10 alkenyl, C3-C10 cycloalkyl, 3- to 10-membered heterocycloalkyl, aryl, or heteroaryl;

-L[1]-R[5] is —(C1-C10 alkylene)-N(R[7])—R[5], —(C1-C10 alkylene)-O—R[5], —(C1-C10 alkyl)-S—R[5], —(C2-C10 alkenylene)-N(R[7])—R[5], —(C2-C10 alkenylene)-O—R[5], —(C2-C10 alkenylene)-S—R[5], —C(O)O—R[5], —C(O)O-L[2]-N(R[7])—R[5], —C(O)O-L[2]-O—R[5], —C(O)O-L[2]-S—R[5], —C(O)O-L[2]-C(O)O—R[5], —C(O)O-L[2]-C(O)N(R[7])—R[5], —C(O)O-L[2]-C(O)N(R[7])-L[3]-N(R[7])—R[5], —C(O)O-L[2]-C(O)N(R[7])-L[3]-O—R[5], —C(O)O-L[2]-C(O)N(R[7])-L[3]-S—R[5], —C(O)N(R[7])—R[5], —C(O)N(R[7])-L[2]-N(R[7])—R[5], —C(O)N(R[7])-L[2]-O—R[5], —C(O)N(R[7])-L[2]-S—R[5], —C(O)N(R[7])-L[2]-C(O)O—R[5], —C(O)N(R[7])-L[2]-C(O)N(R[8])—R[5]—, —C(O)N(R[7])-L[2]-C(O)N(R[8])-L[3]-N(R[7])—R[5], —C(O)O-L[2]-N(R[7])C(O)O—R[5], —C(O)N(R[8])-L[2]-N(R[7])C(O)O—R[5], —C(O)O-L[2]-N(R[7])C(O)N(R[8])—R[5], —C(O)N(R[7])-L[2]-N(R[7])C(O)N(R[8])—R[5], —C(O)N(R[7])-L[2]-C(O)N(R[8])-L[3]-O—R[5] or —C(O)N(R[7])-L[2]-C(O)N(R[8])-L[3]-S—R[5];

—Z— is —C(O)—, —C(O)O—, or —C(O)N(R[7])—;

-L[4]-R[5] is —(C1-C10 alkylene)-N(R[7])—R[5], —(C1-C10 alkylene)-O—R[5], —(C1-C10 alkylene)-S—R[5], —(C2-C10 alkenylene)-N(R[7])—R[5], —(C2-C10 alkenylene)-O—R[5] or —(C2-C10 alkenylene)-S—R[5];

R[7] and R[8] each is independently H, C1-C10 alkyl, or C2-C10 alkenyl;

R[9] is independently H, —F, C1-C10 alkyl, or C2-C10 alkenyl;

L[2] and L[3] each is divalent —(C1-C10 alkylene)-, or —(C2-C10 alkenylene)-; and X is a halogen atom.

In some embodiments, the adenosine derivative for use in the disclosed methods is a compound of formula (1)-(8), formula (1a), formula (1b), formula (1-A)-(8-A), formula (4-B), or formula (4-C). In some embodiments, the adenosine derivative for use in the disclosed methods is a compound of formula (4-A) or formula (4-C). In some embodiments, the adenosine derivative for use in the disclosed methods is a compound of formula (4-A) having the structure:

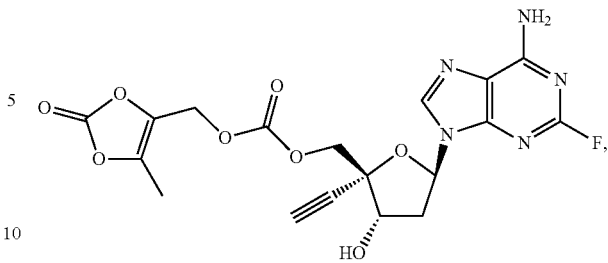

or a pharmaceutically acceptable salt, tautomer, or solvate thereof.

In some embodiments of the present methods, the adenosine derivative is an isomer of formula (1)-(8), formula (1a), formula (1b), formula (1-A)-(8-A), formula (4-B), or formula (4-C). Isomers described above, such as tautomers, stereoisomers, cis/trans isomers or a combination thereof can be suitable. In some embodiments, the stereoisomer of an adenosine derivative disclosed herein is an enantiomer and/or a diastereomer. In some embodiments, the isomer is an inhibitor of reverse transcriptase that has in vivo activity.

In some embodiments of the present methods, the adenosine derivatives of formula (1) comprise a C1-C10 alkyl and/or C2-C10 alkenyl that is linear or branched. In some embodiments, the adenosine derivative comprises a combination of C1-C10 alkyl, C2-C10 alkenyl, C3-C10 cycloalkyl, 3- to 10-membered heterocycloalkyl, aryl and heteroaryl.

In some embodiments of the present methods, the adenosine derivative includes linker L[1] that comprises one or more repeats of a same group or a combination of different groups as disclosed herein. Non-limiting examples of the linker L[1] and other chemically possible combinations include those described above, e.g., in formula (1).

In some embodiments, X is a halogen atom selected from the group consisting of fluorine, chlorine, bromine and iodine (alternatively referred to as fluoro (F), chloro (Cl), bromo (Br), and iodo (I)). In one embodiment, X is F. In another embodiment, X is Cl. In yet another embodiment, X is Br. Non-limiting examples of adenosine derivatives of the present disclosure are provided herein.

In some embodiments, the adenosine derivative for use in the disclosed methods is a compound of formula (1a):

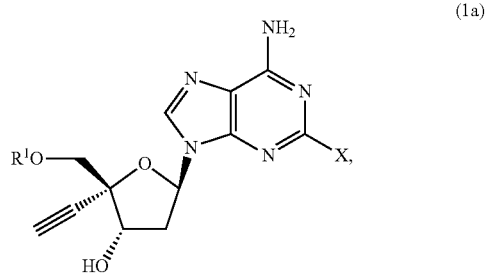

or pharmaceutically acceptable salt, tautomer, or solvate thereof, wherein R[1] and X are as defined above for formula (1).

In some embodiments, the adenosine derivative for use in the disclosed methods is a compound of formula (1b):

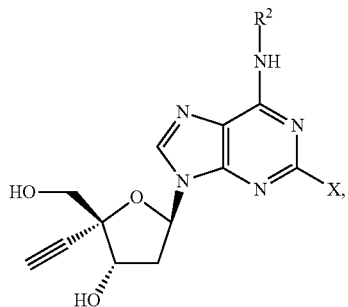

(1b)

or pharmaceutically acceptable salt, tautomer, or solvate thereof, wherein $R^2$ and X are as defined above for formula (1).

In some embodiments, the methods disclosed herein comprise an adenosine derivative having a formula selected from the group consisting of:

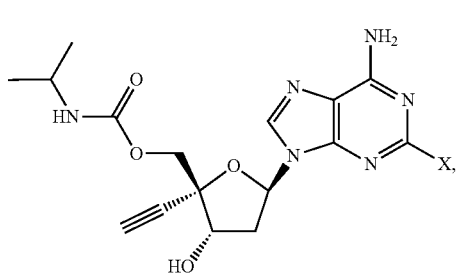

formula (2)

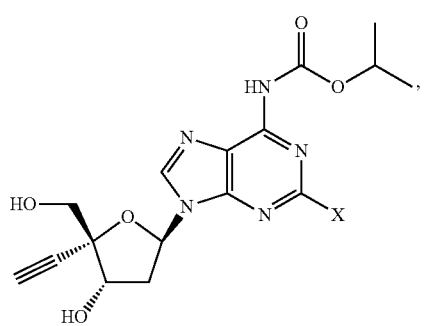

formula (3)

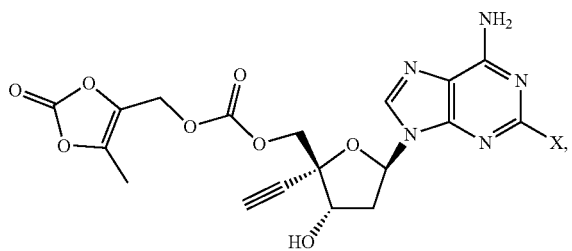

formula (4)

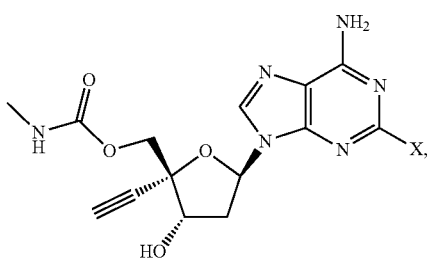

formula (5)

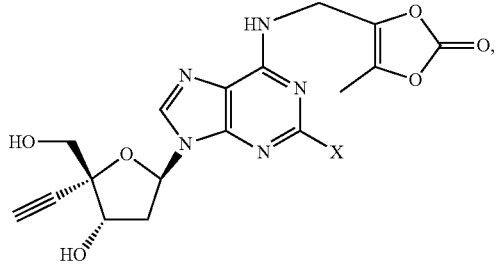

formula (6)

formula (7)

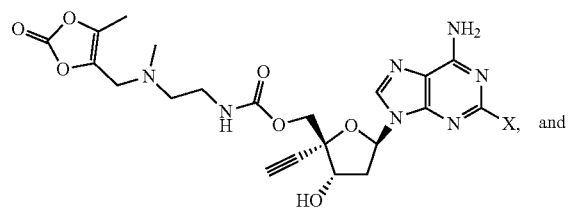

formula (8)

formula (4-B)

or a pharmaceutically acceptable salt, tautomer, or solvate thereof.

In some embodiments, X is Cl, F or Br. In some embodiments, X is F.

In some embodiments, the methods disclosed herein comprise an adenosine derivative having a formula selected from the group consisting of:

formula (2-A)

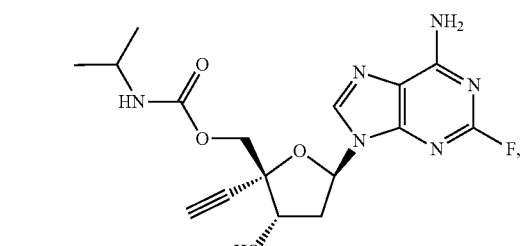

formula (3-A)

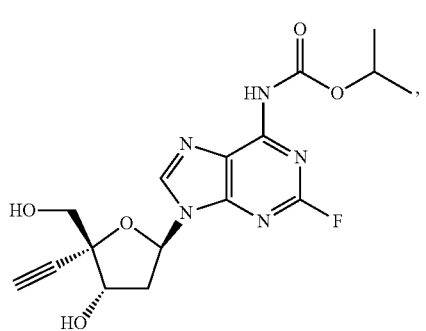

formula (4-A)

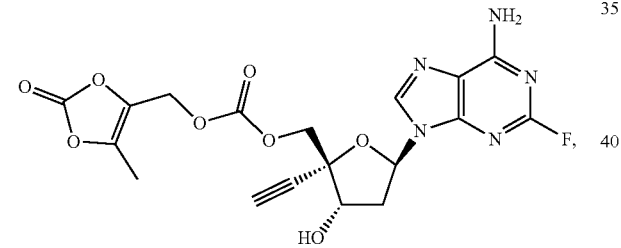

formula (5-A)

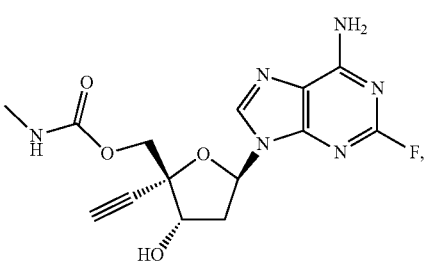

formula (6-A)

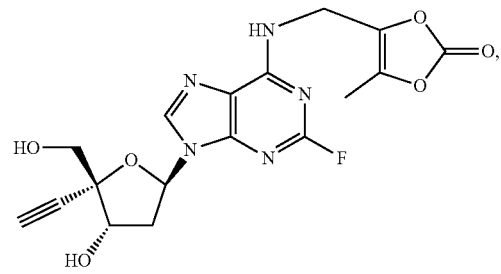

formula (7-A)

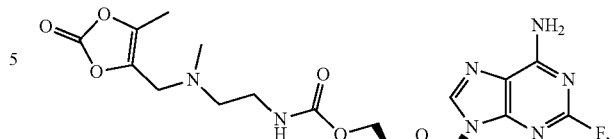

formula (8-A)

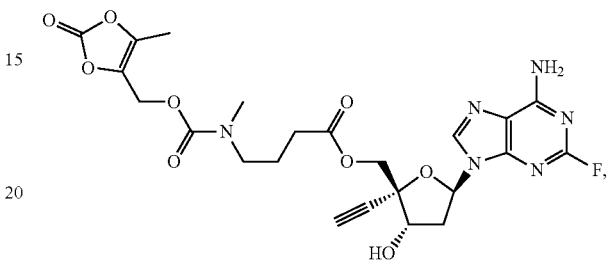

formula (4-C)

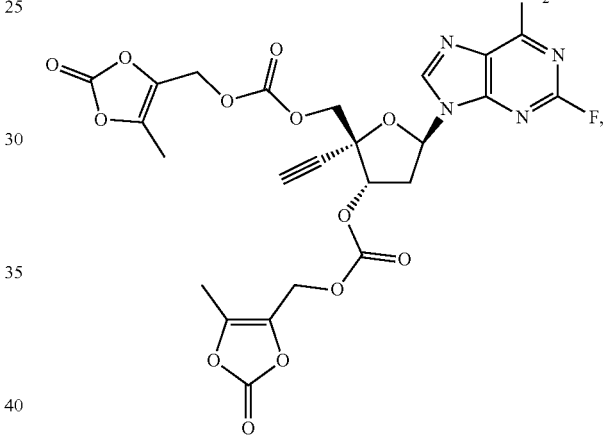

or a pharmaceutically acceptable salt, tautomer, or solvate thereof.

In some embodiments, the methods of the present disclosure comprise an adenosine derivative selected from the group consisting of: ((2R,3S,5R)-5-(6-amino-2-fluoro-9H-purin-9-yl)-2-ethynyl-3-hydroxytetrahydrofuran-2-yl) methyl isopropylcarbamate, isopropyl (9-((2R,4S,5R)-5-ethynyl-4-hydroxy-5-(hydroxymethyl)tetrahydrofuran-2-yl)-2-fluoro-9H-purin-6-yl)carbamate, ((2R,3S,5R)-5-(6-amino-2-fluoro-9H-purin-9-yl)-2-ethynyl-3-hydroxytetrahydrofuran-2-yl)methyl ((5-methyl-2-oxo-1,3-dioxol-4-yl)methyl) carbonate, ((2R,3S,5R)-5-(6-amino-2-fluoro-9H-purin-9-yl)-2-ethynyl-3-hydroxytetrahydrofuran-2-yl)methyl methylcarbamate, 4-(((9-((2R,4S,5R)-5-ethynyl-4-hydroxy-5-(hydroxymethyl)tetrahydrofuran-2-yl)-2-fluoro-9H-purin-6-yl)amino)methyl)-5-methyl-1,3-dioxol-2-one, ((2R,3S,5R)-5-(6-amino-2-fluoro-9H-purin-9-yl)-2-ethynyl-3-hydroxytetrahydrofuran-2-yl)methyl (2-(methyl((5-methyl-2-oxo-1,3-dioxol-4-yl)methyl)amino) ethyl)carbamate, [(2R,3S,5R)-5-(6-amino-2-fluoro-purin-9-yl)-2-ethynyl-3-hydroxy-tetrahydrofuran-2-yl]methyl 4-[methyl-[(5-methyl-2-oxo-1,3-dioxol-4-yl)methoxycarbonyl]amino]butanoate, and pharmaceutically acceptable salts thereof.

As disclosed above, an adenosine derivative suitable for use in the disclosed methods can be free from monophosphate group, diphosphate group, tri-phosphate group or a combination thereof. In some embodiments, an $R^1$ and/or $R^2$ group of an adenosine derivative of disclosed herein is free from monophosphate group, diphosphate group, tri-phosphate group or a combination thereof.

In some embodiments, the adenosine derivative or pharmaceutically acceptable salt, tautomer, or solvate thereof is administered to the subject in a dosage (effective dosage) ranging from about 10 mg to about 2000 mg, e.g., about 10 mg, about 25 mg, about 50 mg, about 75 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, or about 2000 mg, including all ranges and values therebetween. In some embodiments, the adenosine derivative or pharmaceutically acceptable salt, tautomer, or solvate thereof is administered to the subject in a dosage (effective dosage) ranging from 100 mg to 2000 mg, 100 mg to 1900 mg, 100 mg to 1800 mg, 100 mg to 1700 mg, 100 mg to 1600 mg, 100 mg to 1500 mg, 100 mg to 1400 mg, 100 mg to 1300 mg, 100 mg to 1200 mg, 100 mg to 1100 mg, 100 mg to 1000 mg, 100 mg to 900 mg, 100 mg to 800 mg, 100 mg to 700 mg, 100 mg to 600 mg, 100 mg to 500 mg, 100 mg to 400 mg or 100 mg to 300 mg, 200 mg to 1000 mg, 300 mg to 1000 mg, 400 mg to 1000 mg, 500 mg to 1000 mg, 600 mg to 1000 mg, 700 mg to 1000 mg, 800 mg to 1000 mg, 900 mg to 1000 mg, 200 mg to 1200 mg, 300 mg to 1200 mg, 400 mg to 1200 mg, 500 mg to 1200 mg, 600 mg to 1200 mg, 700 mg to 1200 mg, 800 mg to 1200 mg, 900 mg to 1200 mg, 1000 mg to 1200, 200 mg to 2000 mg, 300 mg to 2000 mg, 400 mg to 2000 mg, 500 mg to 2000 mg, 600 mg to 2000 mg, 700 mg to 2000 mg, 800 mg to 2000 mg, 900 mg to 2000 mg, or 1000 mg to 2000. In some embodiments, the adenosine derivative or pharmaceutically acceptable salt, tautomer, or solvate thereof is administered to the subject in a dosage (effective dosage) ranging from 700 mg to 2000 mg. In some embodiments, the adenosine derivative or pharmaceutically acceptable salt, tautomer, or solvate thereof is administered to the subject in a dosage (effective dosage) ranging from 700 mg to 1200 mg.

In some embodiments, the adenosine derivative, or pharmaceutically acceptable salt, tautomer, or solvate thereof is administered to a subject via intramuscular (IM) injection, subcutaneous (SC) injection, intravenous (IV) injection, oral administration, implant application or a combination thereof. In some embodiments, the adenosine derivative, or pharmaceutically acceptable salt, tautomer, or solvate thereof is administered to a subject via IM and/or SC administration. An implant application can include an implantable device or a film that contains the pharmaceutical composition disclosed herein. The implant application can comprise vaginal ring, film, membrane, patch, other devices, or a combination thereof.

In some embodiments, the methods disclosed herein comprise administering the effective doses via oral administration and/or by injection. In some embodiments, the methods disclosed herein comprise administering the effective doses via oral administration. In some embodiments, the method disclosed herein comprise administering the subject the effective dosages orally, such as by taking one or more tablets, once per week (QW) to once per 8 weeks (Q8W). In some embodiments, the method disclosed herein comprise administering the subject the effective dosages by injection, such as by one or more injections every month, every two months, every three months, every four months, every five months, every six months, every seven months, every eight months, every nine months, every ten months, every eleven months or every twelve months. In some embodiments, the effective dosages are administered by subcutaneous and/or intramuscular injection.

In some embodiments, the capsid (CA) inhibitor or composition thereof and the adenosine derivative or composition thereof are administered to the subject simultaneously or sequentially. In some embodiments, the CA inhibitor or composition and the adenosine derivative or composition thereof are administered to the subject simultaneously. The term "simultaneously" refers to the CA inhibitor or composition and the adenosine derivative or composition thereof being administered to the subject at the same time or within a time period of a few seconds, such as 0 to 60 seconds to a few minutes, such as 1 to 5 minutes. In some embodiments, the CA inhibitor or composition and the adenosine derivative or composition thereof are administered to the subject sequentially within a time period in a range of from 0.1 minute to 72 hours, 0.1 minute to 48 hours, 0.1 minute to 24 hours, 0.1 minute to 12 hours, 0.1 minute to 4 hours, 0.1 minute to 1 hour, 0.1 minute to 30 minutes, 0.1 minute to about 5 minutes, or 0.1 minute to about 1 minute. When tablet forms are used, one or more tablets comprising the CA inhibitor and one or more tablets comprising the adenosine derivative are administered to the subject by one oral intake or within a time period described above. Any of the time ranges disclosed herein are either before or after. In some embodiments, the CA inhibitor or composition thereof is administered before the adenosine derivative or composition thereof is administered. In some embodiments, the CA inhibitor or composition thereof is administered after the adenosine derivative or composition thereof is administered.

In some embodiments, the capsid (CA) inhibitor or composition thereof and the adenosine derivative or composition thereof are administered to the subject once every day to once every 12 months. In some embodiments, the CA inhibitor or composition thereof and the adenosine derivative or composition thereof are administered to the subject once every 3 months, every 4 months, every 5 months, every 6 months, every 7 months, every 8 months, every 9 months, every 10 months, every 11 months, or every 12 months. In some embodiments, the CA inhibitor or composition thereof and the adenosine derivative or composition thereof are administered to the subject once every 6 months. The CA inhibitor or composition thereof and the adenosine derivative or composition thereof are administered to the subject simultaneously or sequentially as describe above and hereafter. In some embodiments, the CA inhibitor or composition thereof and the adenosine derivative or composition thereof are administered to the subject once every one to 8 weeks. In some embodiments, the CA inhibitor or composition thereof and the adenosine derivative or composition thereof are administered to the subject once every one week (QW), once every two weeks (Q2W), once every 3 weeks (Q3W), once every 4 weeks (Q4W), once every 5 weeks (Q5W), once every 6 weeks (Q6W), once every 7 weeks (Q7W) or once every 8 weeks (Q8W). In some embodiments, the CA inhibitor or composition thereof and the adenosine derivative or composition thereof are administered to the subject once every month (QM). In some embodiments, the CA inhibitor or composition thereof and the adenosine derivative or composition thereof are administered to the subject orally using one or more tablets. In some embodiments, the CA inhibitor or composition thereof and the adenosine derivative or composition thereof are administered to the subject orally using one or more tablets once every week (QW). The administration timing and frequency described above and hereafter are hereby collectively referred to as "administration schedule" or "administering schedule", in plural or singular form.

In some embodiments, the capsid (CA) inhibitor or composition thereof and the adenosine derivative or composition thereof are administered to the subject using a combination of oral and injection administrations simultaneously or sequentially as describe above and hereafter. In some embodiments, the CA inhibitor or composition thereof is administered to the subject every 6 months via injection and the adenosine derivative or composition thereof is administered to the subject orally once every week (QW), once every two weeks (Q2W), once every 3 weeks (Q3W), once every 4 weeks (Q4W), once every 5 weeks (Q5W), once every 6 weeks (Q6W), once every 7 weeks (Q7W) or once every 8 weeks (Q8W). In some embodiments, the CA inhibitor or composition thereof is administered to the subject every month (QM) via injection or orally and the adenosine derivative or composition thereof are administered to the subject orally once every month (QM).

In some embodiments, the effective dosage of the capsid (CA) inhibitor is in a range of from 300 mg to 2000 mg once every week (QW) to once every 8 weeks (Q8W) and the effective dosage of the adenosine derivative or composition thereof is a range of from 100 mg to 2000 mg of the adenosine derivative once every week (QW) to once every 8 weeks (Q8W). In some embodiments, the effective dosage of the CA inhibitor is in a range of from 300 mg to 2000 mg once every month (QM) and the effective dosage of the adenosine derivative, or composition thereof is a range of from 100 mg to 2000 mg of the adenosine derivative once every month (QM). In some embodiments, the effective dosage of the CA inhibitor is in a range of from 300 mg to 1200 mg once every month (QM) and the effective dosage of the adenosine derivative is in a range of from 100 mg to 1200 mg of the adenosine derivative once every month (QM).

In some embodiments, an effective dosage of an anti-HIV agent and an adenosine derivative disclosed herein, or pharmaceutically acceptable salt, tautomer, or solvate thereof provides a synergistic effect in the treatment of a disease, wherein the disease is Acquired Immune Deficiency Syndrome (AIDS), wild-type HIV-1, NRTI-resistant HIV-1, HIV-2, HIV having M184V mutations, HIV having K65R, multidrug resistant HIV, or an RNA virus infection. In some embodiments, an effective dosage of a CA inhibitor and an adenosine derivative disclosed herein, or pharmaceutically acceptable salt, tautomer, or solvate thereof provides a synergistic effect in the treatment of a disease, wherein the disease is Acquired Immune Deficiency Syndrome (AIDS), wild-type HIV-1, NRTI-resistant HIV-1, HIV-2, HIV having M184V mutations, HIV having K65R, multidrug resistant HIV, or an RNA virus infection. In some embodiments the disease is HIV-1. In some embodiments, the CA inhibitor is lenacapavir and the adenosine derivative is a compound having the structure of formula (4-A).

The effective dosage of the capsid (CA) inhibitor and the effective dosage of the adenosine derivative disclosed herein individually or in combination is suitable. For example, the effective dosage of the CA inhibitor is administered once every week (QW) and the effective dosage of the adenosine derivative is administered from once every week (QW) to once every 8 weeks (Q8W). In another example, the effective dosage of the adenosine derivative is administered once every week (QW) and the effective dosage of the CA inhibitor is administered from once every week (QW) to once every 8 weeks (Q8W). A combination of once every week (QW) is preferred. In some embodiments, the effective dosage of the CA inhibitor is in a range of from 300 mg to 600 mg once every week (QW) and the effective dosage of the adenosine derivative is a range of from 600 mg to 900 mg of the adenosine derivative once every week (QW). In some embodiments, the effective dosage of the CA inhibitor is in a range of from 300 mg to 600 mg once every week (QW) via one or more oral tablets and the effective dosage of the adenosine derivative is a range of from 600 mg to 900 mg of the adenosine derivative once every week (QW) via one or more oral tablets. In some embodiments, the effective dosage of the CA inhibitor is in a range of from 600 mg to 2000 mg once every month (QM), the effective dosage of the adenosine derivative is a range of from 600 mg to 2000 mg of the adenosine derivative once every month (QM), or a combination thereof. In some embodiments, the effective dosage of the CA inhibitor is in a range of from 300 mg to 600 mg once every week (QW) of the lenacapavir and the effective dosage of the adenosine derivative is in a range of from 100 mg to 2000 mg of the adenosine derivative once every week (QW) to once every 8 weeks (Q8W). In some embodiments, the effective dosage of the CA inhibitor is in a range of from 900 mg to 2000 mg once every month (QM) of the lenacapavir and the effective dosage of the adenosine derivative is in a range of from 100 mg to 1200 mg once every week (QW) to 100 mg to 2000 mg once every 8 weeks (Q8W) of the adenosine derivative.

In some embodiments, at least one of the capsid (CA) inhibitor or composition thereof and the adenosine derivative or composition thereof is administered to a subject once every month (QM). In some embodiments, the CA inhibitor or composition thereof is administered to a subject once every month (QM) and the adenosine derivative or composition thereof is administered to a subject from once every week (QW) to once every 12 months as described above and hereafter. In some embodiments, the adenosine derivative or composition thereof is administered to a subject once every month (QM) and the CA inhibitor or composition thereof is administered to a subject from once every week (QW) to once every 12 months as described above and hereafter. In some embodiments, both the adenosine derivative or composition thereof and the CA inhibitor or composition thereof is administered to a subject once every month (QM).

In some embodiments, an adenosine derivative of the present disclosure is administered to a subject at a dosage of 900 mg once per week (QW) together with 900 mg of the CA inhibitor such as GS-6207 (lenacapavir) once every 6 months.

In some embodiments, an adenosine derivative of the present disclosure is administered to a subject at a dosage of 900 mg once per week (QW) together with together with the CA inhibitor such as GS-6207 (lenacapavir) at a dosage in a range of from 100 mg to 900 mg once every 3 months.

In some embodiments, an adenosine derivative or composition thereof is administered to a subject at a dosage of 900 mg once per week (QW) together with the CA inhibitor such as GS-6207 (lenacapavir) at a dosage in a range of from 100 mg to 900 mg once every one month.

In some embodiments, an adenosine derivative of the present disclosure is administered to a subject at a dosage of 900 mg once per week (QW) together with the CA inhibitor such as GS-6207 (lenacapavir) at a dosage in a range of from 100 mg to 900 mg once every two weeks.

In some embodiments, an adenosine derivative of the present disclosure is administered to a subject at a dosage of 900 mg once per week (QW) together with the CA inhibitor such as GS-6207 (lenacapavir) at a dosage in a range of from 100 mg to 900 mg once every week (QW).

In some embodiments, an adenosine derivative of the present disclosure is administered to a subject at a dosage in a range of from 600 mg to 2000 mg once 6 months together with the CA inhibitor such as GS-6207 (lenacapavir) at a dosage of 900 mg to 2000 mg once every 6 months.

In some embodiments, an adenosine derivative of the present disclosure is administered to a subject at a dosage in a range of from 600 mg to 1200 mg once every 6 months together with the CA inhibitor such as GS-6207 (lenacapavir) at a dosage of 900 mg to 1200 mg once every 6 months.

In some embodiments, an adenosine derivative of the present disclosure is administered to a subject at a dosage in a range of from 600 mg to 2000 mg once every 3 months together with the CA inhibitor such as GS-6207 (lenacapavir) at a dosage of 900 mg to 2000 mg once every 6 months.

In some embodiments, an adenosine derivative of the present disclosure is administered to a subject at a dosage in a range of from 600 mg to 2000 mg once every one month together with the CA inhibitor such as GS-6207 (lenacapavir) at a dosage of 900 mg to 2000 mg once every 6 months.

In some embodiments, an adenosine derivative of the present disclosure is administered to a subject at a dosage in a range of from 600 mg to 1200 mg once every two weeks together with the CA inhibitor such as GS-6207 (lenacapavir) at a dosage of 900 mg to 2000 mg once every 6 months.

In some embodiments, an adenosine derivative of the present disclosure is administered to a subject at a dosage in a range of from 600 mg to 1200 mg once every week together with the CA inhibitor such as GS-6207 (lenacapavir) at a dosage of 900 mg to 2000 mg once every 6 months.

In some embodiments, the adenosine derivative of the present disclosure is administered orally in tablet form and the CA inhibitor such as GS-6207 (lenacapavir) is injected. In some embodiments, the CA inhibitor such as GS-6207 (lenacapavir) is administered orally in tablet form.

In some embodiments, the HIV infection is caused by wild-type HIV-1, NRTI-resistant HIV-1, HIV-2, HIV having M184V mutations, HIV having K65R, or multidrug resistant HIV.

In some embodiments, the subject is a person having highly treatment-experienced HIV, a person who has been heavily treated and HIV multidrug-resistant, a person who is HIV-positive, a person who is undertaking pre-exposure prophylaxis (PrEP) by taking one or more anti-HIV medications, a woman at risk of HIV, or a man at risk of HIV.

In some embodiments, a capsid inhibitor and an adenosine derivative disclosed herein or pharmaceutically acceptable salt, tautomer, or solvate thereof provide synergistic antiviral activity in the treatment of HIV, AIDS, or RNA virus when administered to a subject according to the methods disclosed herein. In some embodiments, the synergistic antiviral activity is measured by a synergy volume. In some embodiments, a synergy volume of 50-100 indicates synergistic antiviral activity. A synergy volume of >100 indicates highly synergistic antiviral activity. As used herein, synergy is achieved when the combined effect of the adenosine derivative and the capsid inhibitor is larger than the additive effect of each individual drug.

In some embodiments, the method of the present disclosure further comprises measuring a specimen of the subject to determine a measured level of a target drug in the specimen, wherein the target drug can have a formula (T-1):

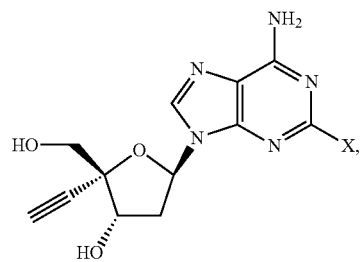

an isomer thereof, or a pharmaceutically acceptable salt thereof. In some embodiments, X is a halogen selected from the group consisting of F, Cl, Br and I. In some embodiments X is I.

In some embodiments, the target drug has a formula (T-1A):

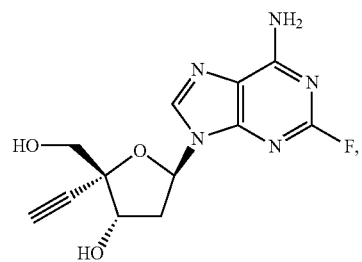

an isomer thereof, or a pharmaceutically acceptable salt thereof.

In some embodiments, the target drug is (2R,3S,5R)-5-(6-amino-2-fluoro-9H-purin-9-yl)-2-ethynyl-2-(hydroxymethyl)tetrahydrofuran-3-ol (also referred to as 4'-ethynyl-2-fluoro-2'-deoxyadenosine, EFdA), or a pharmaceutically acceptable salt thereof.

In some embodiments, the target drug is a degradation or metabolized product of the compound (T-1), (T-1A) or EFdA.

The specimen is a blood sample, a urine sample, a body fluid sample, a tissue sample or a combination thereof from the subject, such as a patient.

The measured level of the target drug is determined with analytical method known to those skilled in the art, such as, but not limited to, HPLC, GC, MS, GC-MS, or a combination thereof.

The method of the present disclosure further comprises adjusting the effective dosage to produce a modified effective dosage if the measured level of the target drug is different from a predetermined target level of the target drug and administering the modified effective dosage to the subject.

In some embodiments, the target drug is a compound of formula (T-1A):

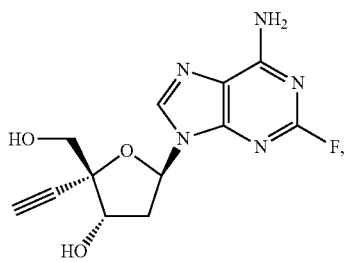 [SMILES: C#C[C@]1(CO)O[C@@H](n2cnc3c(N)nc(F)nc32)C[C@@H]1O]

an isomer thereof, or a pharmaceutically acceptable salt thereof.

In some embodiments, the target drug is (2R,3S,5R)-5-(6-amino-2-fluoro-9H-purin-9-yl)-2-ethynyl-2-(hydroxymethyl)tetrahydrofuran-3-ol (also referred to as 4'-ethynyl-2-fluoro-2'-deoxyadenosine, EFdA), or a pharmaceutically acceptable salt thereof.

In some embodiments, the target drug is a degradation or metabolized product of the compound (T-1), (T-TA) or EFdA.

The specimen can be a blood sample, a urine sample, a body fluid sample, a tissue sample or a combination thereof from the subject, such as a patient.

The measured level of the target drug can be determined with analytical method known to those skilled in the art, such as, but not limited to, HPLC, GC, MS, GC-MS, or a combination thereof.

The methods of the present disclosure can further comprise adjusting the effective dosage to produce a modified effective dosage if the measured level of the target drug is different from a predetermined target level of the target drug and administering the modified effective dosage to the subject.

In some embodiments, the methods of the present disclosure further comprise administering to a subject an effective dosage of one or more additional anti-HIV agents selected from the group consisting of abacavir, abacavir sulfate, lamivudine, amprenavir, atazanavir, atazanavir sulfate, AZT, bictagrevir, cabotegravir, darunavir, dideoxycytidine, dideoxyinosine, dolutegravir, doravirine, efavirenz, emtricitabine, tenofovir disoproxil fumarate, tenofovir alafenamide, 4'-ethynyl-2-fluoro-2'-deoxyadenosine, elvitegravir, etravirine, fosamprenavir calcium, indinavir, indinavir sulfate, lamivudine, lopinavir, a combination of lopinavir and ritonavir, darunavir, a combination of darunavir and cobicistat, maraviroc, nelfinavir, nelfinavir mesylate, nevirapine, PPL-100, raltegravir, rilpivirine, stavudine, tipranavir, and vicriviroc or a combination thereof. Other anti-HIV agents identified or developed, or combination thereof, can also be suitable.

The present disclosure is further directed to a use of the adenosine derivative and a capsid (CA) inhibitor, optionally, one or more pharmaceutically acceptable carriers, disclosed herein for manufacturing a medicament for treating a disease, wherein the disease is Acquired Immune Deficiency Syndrome (AIDS), wild-type HIV-1, NRTI-resistant HIV-1, HIV-2, HIV having M184V mutations, HIV having K65R, multidrug resistant HIV, or an RNA virus infection. Any of the aforementioned adenosine derivatives can be suitable. Any of the aforementioned pharmaceutically acceptable carriers can be suitable.

The present disclosure is further directed to a method for the prevention of infection in a subject in need thereof, the method comprising administering the subject an effective dosage of any one of the pharmaceutical compositions or the therapeutical compositions disclosed herein, wherein the subject is free from detectable symptoms of the infection. In some embodiments, the infection comprises a disease selected from Acquired Immune Deficiency Syndrome (AIDS), an infection of wild-type HIV-1, NRTI-resistant HIV-1, HIV-2, HIV having M184V mutations, HIV having K65R, multidrug resistant HIV, an RNA virus infection, or a combination thereof.

The detectable symptoms can include, but are not limited to, symptoms of Acquired Immune Deficiency Syndrome (AIDS), symptoms of infection of HIV viruses comprising wild-type HIV-1, NRTI-resistant HIV-1, HIV-2, HIV having M184V mutations, HIV having K65R, multidrug resistant HIV, or a combination thereof. The detection of the HIV viruses can be done by PCR, reverse PCR, immunodetection of an antigen or an antibody related to AIDS or HIV.

Without being bound by any particular theory, an advantage of the present compositions and methods is that the adenosine derivatives disclosed herein can have a fast conversion to the target drug. As described below in the Examples, greater than about 60% of the adenosine derivatives of the present disclosure surprisingly and unexpectedly can be converted to the target drug within about 30 min in contact with human plasma.

One advantage of the combination of the adenosine derivatives and the capsid (CA) inhibitor such as GS-6207 (lenacapavir) can be the potential benefits for the prevention of HIV infection via Pre-exposure prophylaxis (or PrEP), which is a way for people who do not have HIV but who are at very high risk of getting HIV to prevent HIV infection by taking a medication regularly. Currently, a medication available under the brand name Truvada contains two medicines (tenofovir and emtricitabine) that are used in combination with other medicines to treat HIV. When someone is exposed to HIV, these medicines can work to keep the virus from establishing a permanent infection. The combination of the adenosine derivatives and the capsid (CA) inhibitor such as GS-6207 (lenacapavir) disclosed herein can provide an additional PrEP for HIV prevention, preferably with once per week (QW) schedule. It is known that when taken consistently, PrEP is highly effective for preventing HIV. PrEP is much less effective if it is not taken consistently. The weekly schedule (QW) of the combination of the adenosine derivatives and the capsid (CA) inhibitor such as GS-6207 (lenacapavir) disclosed herein can provide convenience and help to maintain a consistent intake of medications and therefore help in HIV prevention.

NUMBERED EMBODIMENTS OF THE DISCLOSURE

Other subject matter contemplated by the present disclosure is set out in the following numbered embodiments:

1. A method of treating or preventing an HIV infection, comprising administering to a subject in need thereof an effective amount of:

(a) a capsid inhibitor; and (b) an adenosine derivative, wherein the adenosine derivative is a compound of formula (1):

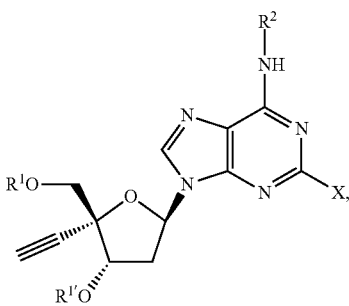

(1)

or pharmaceutically acceptable salt or solvate thereof, wherein:

$R^1$, $R^{1'}$, and $R^2$ each is independently H, —C(O)N($R^3$)($R^{3'}$), —C(O)O$R^4$, —$R^5$, -$L^1$-$R^5$, or —Z-$L^4$-$R^5$, provided that least one of $R^1$ and $R^2$ is not H;

$R^3$, $R^{3'}$ and $R^4$ each is independently H, C1-C10 alkyl, C2-C10 alkenyl, C3-C10 cycloalkyl, 3- to 10-membered heterocycloalkyl, aryl, or heteroaryl;

$R^5$ is:

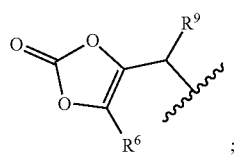

$R^6$ is H, C1-C10 alkyl, C2-C10 alkenyl, C3-C10 cycloalkyl, 3- to 10-membered heterocycloalkyl, aryl, or heteroaryl;

-$L^1$-$R^5$ is —(C1-C10 alkylene)-N($R^7$)—$R^5$, —(C1-C10 alkylene)-O—$R^5$, —(C1-C10 alkylene)-S—$R^5$, —(C2-C10 alkenylene)-N($R^7$)—$R^5$, —(C2-C10 alkenylene)-O—$R^5$, —(C2-C10 alkenylene)-S—$R^5$, —C(O)O—$R^5$, —C(O)O-$L^2$-N($R^7$)—$R^5$, —C(O)O-$L^2$-O—$R^5$, —C(O)O-$L^2$-S—$R^5$, —C(O)O-$L^2$-C(O)O—$R^5$, —C(O)O-$L^2$-C(O)N($R^7$)—$R^5$, —C(O)O-$L^2$-C(O)N($R^7$)-$L^3$-N($R^7$)—$R^5$, —C(O)O-$L^2$-C(O)N($R^7$)-$L^3$-O—$R^5$, —C(O)O-$L^2$-C(O)N($R^7$)-$L^3$-S—$R^5$, —C(O)N($R^7$)—$R^5$, —C(O)N($R^7$)-$L^2$-N($R^7$)—$R^5$, —C(O)N($R^7$)-$L^2$-O—$R^5$, —C(O)N($R^7$)-$L^2$-S—$R^5$, —C(O)N($R^7$)-$L^2$-C(O)O—$R^5$, —C(O)N($R^7$)-$L^2$-C(O)N($R^8$)—$R^5$—, —C(O)N($R^7$)-$L^2$-C(O)N($R^8$)-$L^3$-N($R^7$)—$R^5$, —C(O)O-$L^2$-N($R^7$)C(O)O—$R^5$, —C(O)N($R^8$)-$L^2$-N($R^7$)C(O)O—$R^5$, —C(O)O-$L^2$-N($R^7$)C(O)N($R^8$)—$R^5$, —C(O)N($R^7$)-$L^2$-N($R^7$)C(O)N($R^8$)—$R^5$, —C(O)N($R^7$)-$L^2$-C(O)N($R^8$)-$L^3$-O—$R^5$ or —C(O)N($R^7$)-$L^2$-C(O)N($R^8$)-$L^3$-S—$R^5$;

—Z— is —C(O)—, —C(O)O—, or —C(O)N($R^7$)—;

-$L^4$-$R^5$ is —(C1-C10 alkylene)-N($R^7$)—$R^5$, —(C1-C10 alkylene)-O—$R^5$, —(C1-C10 alkylene)-S—$R^5$, —(C2-C10 alkenylene)-N($R^7$)—$R^5$, —(C2-C10 alkenylene)-O—$R^5$ or —(C2-C10 alkenylene)-S—$R^5$;

$R^7$ and $R^8$ each is independently H, C1-C10 alkyl, or C2-C10 alkenyl;

$R^9$ is independently H, —F, C1-C10 alkyl, or C2-C10 alkenyl;

$L^2$ and $L^3$ each is divalent —(C1-C10 alkylene)-, or —(C2-C10 alkenylene)-; and X is a halogen atom.

2. The method of embodiment 1, wherein $R^1$ and $R^2$ each is independently H, —$R^5$, -$L^1$-$R^{5'}$ or —Z-$L^4$-$R^5$.

3. The method of embodiment 1 or 2, wherein $R^1$ and $R^2$ each is independently H, —$R^5$, or -$L^1$-$R^5$.

4. The method of any one of embodiments 1-3, wherein $R^1$ is -$L^1$-$R^5$.

5. The method of any one of embodiments 1-4, wherein $R^{1'}$ is -$L^1$-$R^5$.

6. The method of any one of embodiments 1-4, wherein $R^{1'}$ is H.

7. The method of any one of embodiments 1-6, wherein -$L^1$-$R^5$ is selected from the group consisting of —(C1-C10 alkylene)-N($R^7$)—$R^5$, —(C1-C10 alkylene)-O—$R^5$, —C(O)O-$L^2$-N($R^7$)—$R^5$, —C(O)O-$L^2$-O—$R^5$, —C(O)O-$L^2$-C(O)O—$R^5$, —C(O)O-$L^2$-C(O)N($R^7$)—$R^5$, —C(O)N($R^7$)—$R^5$, —C(O)N($R^7$)-$L^2$-N($R^7$)—$R^5$, —C(O)N($R^7$)-$L^2$-O—$R^5$, —C(O)O-$L^2$-N($R^7$)C(O)O—$R^5$, —C(O)N($R^8$)-$L^2$-N($R^7$)C(O)O—$R^5$, —C(O)O-$L^2$-N($R^7$)C(O)N($R^8$)—$R^5$, —C(O)N($R^7$)-$L^2$-N($R^7$)C(O)N($R^8$)—$R^5$, —C(O)N($R^7$)-$L^2$-C(O)O—$R^5$, and —C(O)N($R^7$)-$L^2$-C(O)N($R^8$)—$R^5$—.

8. The method of any one of embodiments 1-7, wherein -$L^1$-$R^5$ is selected from the group consisting of —C(O)O—$R^5$, —C(O)O-$L^2$-N($R^7$)—$R^5$, —C(O)O-$L^2$-N($R^7$)C(O)O—$R^5$, —C(O)N($R^8$)-$L^2$-N($R^7$)C(O)O—$R^5$, —C(O)O-$L^2$-N($R^7$)C(O)N($R^8$)—$R^5$, —C(O)N($R^7$)-$L^2$-N($R^7$)C(O)N($R^8$)—$R^5$, —C(O)N($R^7$)-$L^2$-N($R^7$)—$R^5$, and —C(O)N($R^7$)-$L^2$-C(O)N($R^8$)—$R^5$—.

9. The method of any one of embodiments 1-7, wherein -$L^1$-$R^5$ is —C(O)O—$R^5$.

10. The method of any one of embodiments 1-9, wherein $R^2$ is H.

11. The method of any one of embodiments 1-10, wherein $R^3$ and $R^{3'}$ each is independently H, C1-C10 alkyl, or C3-C6 cycloalkyl.

12. The method of any one of embodiments 1-10, wherein $R^3$ and $R^{3'}$ each is independently H or C1-C3 alkyl.

13. The method of embodiment 1, wherein $R^4$ is C1-C10 alkyl, or C3-C6 cycloalkyl.

14. The method of embodiment 1 or 2, wherein —Z-$L^4$-$R^5$ is Z—(C1-C10 alkylene)-N($R^7$)—$R^5$ or Z—(C1-C10 alkylene)-O—$R^5$.

15. The method of any one of embodiments 1, 2, and 14, wherein —Z— is —C(O)N($R^7$)—.

16. The method of any one of embodiments 1-15, wherein $R^6$ is C1-C5 alkyl.

17. The method of embodiment 16, wherein $R^6$ is methyl.

18. The method of any one of embodiments 1-17, wherein $R^7$ is H or C1-C5 alkyl.

19. The method of embodiment 18, wherein $R^7$ is H or methyl.

20. The method of any one of embodiments 1-19, wherein $R^8$ is H or C1-C5 alkyl.

21. The method of embodiment 20, wherein $R^8$ is H or methyl.

22. The method of any one of embodiments 1-21, wherein $R^9$ is H or Me. 22a. The method of embodiment 22, wherein $R^9$ is H.

23. The method of any one of embodiments 1-22a, wherein X is F.

24. The method of embodiment 1, wherein the adenosine derivative has the structure:

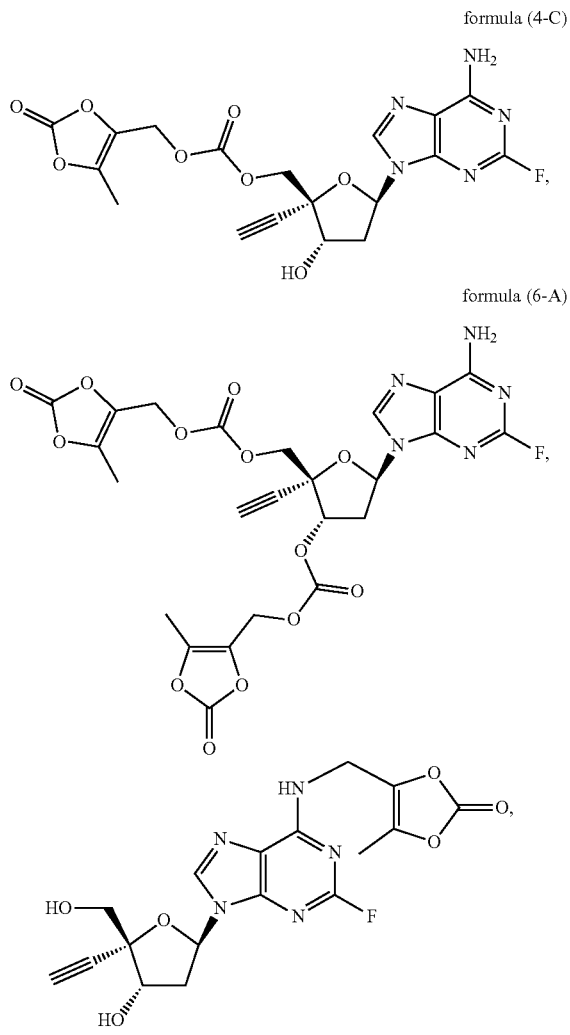

or a pharmaceutically acceptable salt, tautomer, or solvate thereof.

25. The method of embodiment 1, wherein the adenosine derivative is: ((2R,3S,5R)-5-(6-amino-2-fluoro-9H-purin-9-yl)-2-ethynyl-3-hydroxytetrahydrofuran-2-yl)methyl ((5-methyl-2-oxo-1,3-dioxol-4-yl)methyl) carbonate, 4-(((9-((2R,4S,5R)-5-ethynyl-4-hydroxy-5-(hydroxymethyl)tetrahydrofuran-2-yl)-2-fluoro-9H-purin-6-yl)amino)methyl)-5-methyl-1,3-dioxol-2-one, or ((2R,3S,5R)-5-(6-amino-2-fluoro-9H-purin-9-yl)-2-ethynyl-3-((((5-methyl-2-oxo-1,3-dioxol-4-yl)methoxy)carbonyl)oxy)tetrahydrofuran-2-yl)methyl ((5-methyl-2-oxo-1,3-dioxol-4-yl)methyl) carbonate, or pharmaceutically acceptable salt or solvate thereof.

26. The method of any one of embodiments 1-25, wherein the adenosine derivative is a reverse transcriptase inhibitor activity in vivo, a reverse transcriptase chain terminator activity in vivo, a DNA translocation inhibitor activity in vivo, or a combination thereof.

27. The method of any one of embodiments 1-26, wherein the adenosine derivative, or pharmaceutically acceptable salt or solvate thereof is administered orally.

28. The method of any one of embodiments 1-27, wherein the capsid (CA) inhibitor and the adenosine derivative, or pharmaceutically acceptable salt or solvate thereof are administered to the subject simultaneously or sequentially.

29. The method of embodiment 28, wherein the CA inhibitor and the adenosine derivative or pharmaceutically acceptable salt or solvate thereof are administered to the subject sequentially within a time period in a range of from 0.1 minute to 72 hours.

30. The method of any one of embodiments 1-29, wherein the CA inhibitor and the adenosine derivative or pharmaceutically acceptable salt or solvate thereof are administered to the subject once every day to once every 12 months.

31. The method of embodiment 30, wherein the CA inhibitor and the adenosine derivative or pharmaceutically acceptable salt or solvate thereof are administered to the subject once every 6 months.

32. The method of embodiment 30, wherein the CA inhibitor and the adenosine derivative or pharmaceutically acceptable salt or solvate thereof are administered to the subject once every one to 8 weeks.

33. The method of embodiment 30, wherein at least one of the CA inhibitor and the adenosine derivative or pharmaceutically acceptable salt or solvate thereof is administered to the subject once every month.

34. The method of any one of embodiments 1-33, wherein the CA inhibitor is a compound having the structure:

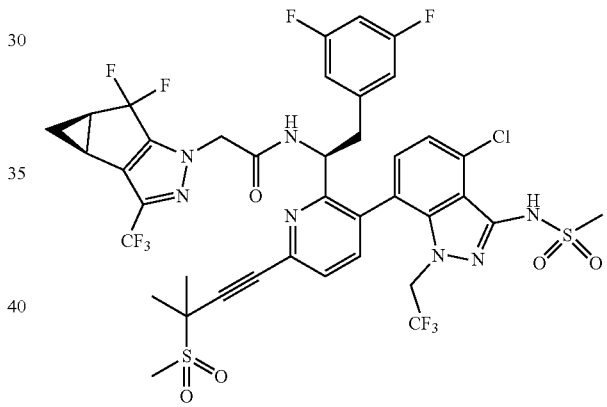

or a pharmaceutically acceptable salt, tautomer, or solvate thereof.

35. The method of embodiment 34, wherein the effective dosage of the CA inhibitor is a single dosage in a range of from 100 mg to 2000 mg administered every 6 months.

36. The method of embodiment 34, wherein the effective dosage of the CA inhibitor is in a range of from 200 mg to 1200 mg administered every 1 to 7 days.

37. The method of embodiment 34, wherein the effective dosage of the CA inhibitor is in a range of from 300 mg to 1200 mg administered once every week (QW) and the effective dosage of the adenosine derivative or pharmaceutically acceptable salt or solvate thereof is a range of from 100 mg to 2000 mg administered once every week (QW) to once every 8 weeks (Q8W).

38. The method of embodiment 34, wherein the effective dosage of the CA inhibitor is in a range of from 900 mg to 2000 mg administered once every month (QM) and the effective dosage of the adenosine derivative or pharmaceutically acceptable salt or solvate thereof is in a range of from 100 mg to 2000 mg administered once every week (QW) to once every 8 weeks (Q8W).

39. The method of any one of embodiments 1-38, wherein the HIV infection is caused by wild-type HIV-1, NRTI-resistant HIV-1, HIV-2, HIV having M184V mutations, HIV having K65R, or multidrug resistant HIV.

40. The method of any one of embodiments 1-39, wherein the subject is a person having highly treatment-experienced HIV, a person who has been heavily treated and HIV multidrug-resistant, a person who is HIV-positive, a person who is undertaking pre-exposure prophylaxis (PrEP) by taking one or more anti-HIV medications, a woman at risk of HIV, or a man at risk of HIV.

40a. The method of any one of embodiments 1-40, wherein the capsid inhibitor is administered orally.

40b. The method of any one of embodiments 1-40, wherein the capsid inhibitor is administered parentally.

40c. The method of embodiment 40b, wherein the parental administration is by intramuscular and/or subcutaneous injection.

40d. The method of any one of embodiments 1-40, wherein the adenosine derivative or pharmaceutically acceptable salt or solvate thereof is administered orally.

40e. The method of any one of embodiments 1-40, wherein the adenosine derivative or pharmaceutically acceptable salt or solvate thereof is administered parentally.

40f. The method of embodiment 40e, wherein the parental administration is by intramuscular and/or subcutaneous injection.

41. A pharmaceutical composition, comprising an effective amount of:
(a) a capsid (CA) inhibitor; and
(b) an adenosine derivative or pharmaceutically acceptable salt, tautomer, or solvate thereof,
wherein the adenosine derivative is a compound having a structure of formula (1):

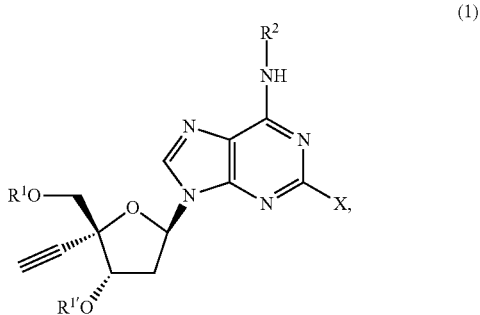

(1)

wherein,
$R^1$, $R^{1'}$, and $R^2$ each is independently H, —C(O)N($R^3$)($R^{3'}$), —C(O)O$R^4$, —$R^5$, -$L^1$-$R^5$, or —Z-$L^4$-$R^5$, provided that at least one of $R^1$ and $R^2$ is not H;

$R^3$, $R^{3'}$ and $R^4$ each is independently H, C1-C10 alkyl, C2-C10 alkenyl, C3-C10 cycloalkyl, 3- to 10-membered heterocycloalkyl, aryl, or heteroaryl;

$R^5$ is:

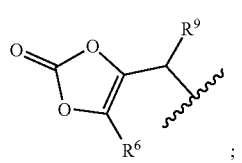

;

$R^6$ is H, C1-C10 alkyl, C2-C10 alkenyl, C3-C10 cycloalkyl, 3- to 10-membered heterocycloalkyl, aryl, or heteroaryl;

-$L^1$-$R^5$ is —(C1-C10 alkylene)-N($R^7$)—$R^5$, —(C1-C10 alkylene)-O—$R^5$, —(C1-C10 alkylene)-S—$R^5$, —(C2-C10 alkenylene)-N($R^7$)—$R^5$, —(C2-C10 alkenylene)-O—$R^5$, —(C2-C10 alkenylene)-S—$R^5$, —C(O)O—$R^5$, —C(O)O-$L^2$-N($R^7$)—$R^5$, —C(O)O-$L^2$-O—$R^5$, —C(O)O-$L^2$-S—$R^5$, —C(O)O-$L^2$-C(O)O—$R^5$, —C(O)O-$L^2$-C(O)N($R^7$)—$R^5$, —C(O)O-$L^2$-C(O)N($R^7$)-$L^3$-N($R^7$)—$R^5$, —C(O)O-$L^2$-C(O)N($R^7$)-$L^3$-O—$R^5$, —C(O)O-$L^2$-C(O)N($R^7$)-$L^3$-S—$R^5$, —C(O)N($R^7$)—$R^5$, —C(O)N($R^7$)-$L^2$-N($R^7$)—$R^5$, —C(O)N($R^7$)-$L^2$-O—$R^5$, —C(O)N($R^7$)-$L^2$-S—$R^5$, —C(O)N($R^7$)-$L^2$-C(O)O—$R^5$, —C(O)N($R^7$)-$L^2$-C(O)N($R^8$)—$R^5$, —C(O)N($R^7$)-$L^2$-C(O)N($R^8$)-$L^3$-N($R^7$)—$R^5$, —C(O)O-$L^2$-N($R^7$)C(O)O—$R^5$, —C(O)N($R^8$)-$L^2$-N($R^7$)C(O)O—$R^5$, —C(O)O-$L^2$-N($R^7$)C(O)N($R^8$)—$R^5$, —C(O)N($R^7$)-$L^2$-N($R^7$)C(O)N($R^8$)—$R^5$, —C(O)N($R^7$)-$L^2$-C(O)N($R^8$)-$L^3$-O—$R^5$ or —C(O)N($R^7$)-$L^2$-C(O)N($R^8$)-$L^3$-S—$R^5$;

—Z— is —C(O)—, —C(O)O—, or —C(O)N($R^7$)—;

-$L^4$-$R^5$ is —(C1-C10 alkylene)-N($R^7$)—$R^5$, —(C1-C10 alkylene)-O—$R^5$, —(C1-C10 alkyl)-S—$R^5$, —(C2-C10 alkenylene)-N($R^7$)—$R^5$, —(C2-C10 alkenylene)-O—$R^5$ or —(C2-C10 alkenylene)-S—$R^5$;

$R^7$ and $R^8$ each is independently H, C1-C10 alkyl, or C2-C10 alkenyl;

$R^9$ is independently H, —F, C1-C10 alkyl, or C2-C10 alkenyl;

$L^2$ and $L^3$ each is —(C1-C10 alkylene)-, or —(C2-C10 alkenylene)-; and

X is a halogen atom.

42. The composition of embodiment 41, wherein $R^1$ and $R^2$ each is independently H, —$R^5$, -$L^1$-$R^{5'}$ or —Z-$L^4$-$R^5$.

43. The composition of embodiment 41 or 42, wherein $R^1$ and $R^2$ each is independently H, —$R^5$, or -$L^1$-$R^5$.

44. The composition of any one of embodiments 41-43, wherein $R^1$ is -$L^1$-$R^5$.

45. The composition of any one of embodiments 41-44, wherein $R^{1'}$ is -$L^1$-$R^5$.

46. The composition of any one of embodiments 41-44, wherein $R^{1'}$ is H.

47. The composition of any one of embodiments 41-46, wherein -$L^1$-$R^5$ is selected from the group consisting of —(C1-C10 alkylene)-N($R^7$)—$R^5$, —(C1-C10 alkylene)-O—$R^5$, —C(O)O-$L^2$-N($R^7$)—$R^5$, —C(O)O-$L^2$-O—$R^5$, —C(O)O-$L^2$-C(O)O—$R^5$, —C(O)O-$L^2$-C(O)N($R^7$)—$R^5$, —C(O)N($R^7$)—$R^5$, —C(O)N($R^7$)-$L^2$-N($R^7$)—$R^5$, —C(O)N($R^7$)-$L^2$-O—$R^5$, —C(O)O-$L^2$-N($R^7$)C(O)O—$R^5$, —C(O)N($R^8$)-$L^2$-N($R^7$)C(O)O—$R^5$, —C(O)O-$L^2$-N($R^7$)C(O)N($R^8$)—$R^5$, —C(O)N($R^7$)-$L^2$-N($R^7$)C(O)N($R^8$)—$R^5$, —C(O)N($R^7$)-$L^2$-C(O)O—$R^5$, and —C(O)N($R^7$)-$L^2$-C(O)N($R^8$)—$R^5$—.

48. The composition of any one of embodiments 41-47, wherein -$L^1$-$R^5$ is selected from the group consisting of —C(O)O—$R^5$, —C(O)O-$L^2$-N($R^7$)—$R^5$, —C(O)O-$L^2$-N($R^7$)C(O)O—$R^5$, —C(O)N($R^8$)-$L^2$-N($R^7$)C(O)O—$R^5$, —C(O)O-$L^2$-N($R^7$)C(O)N($R^8$)—$R^5$, —C(O)N($R^7$)-$L^2$-N($R^7$)C(O)N($R^8$)—$R^5$, —C(O)N($R^7$)-$L^2$-N($R^7$)—$R^5$, and —C(O)N($R^7$)-$L^2$-C(O)N($R^8$)—$R^5$—.

49. The composition of any one of embodiments 41-47, wherein -$L^1$-$R^5$ is —C(O)O—$R^5$.

50. The composition of any one of embodiments 41-49, wherein $R^2$ is H.

51. The composition of any one of embodiments 41-50, wherein $R^3$ and $R^{3'}$ each is independently H, C1-C10 alkyl, or C3-C6 cycloalkyl.

52. The composition of any one of embodiments 41-50, wherein $R^3$ and $R^{3'}$ each is independently H or C1-C3 alkyl.

53. The composition of embodiment 41, wherein $R^4$ is C1-C10 alkyl, or C3-C6 cycloalkyl.

54. The composition of embodiment 41 or 42, wherein —Z-$L^4$-$R^5$ is Z—(C1-C10 alkylene)-N($R^7$)—$R^5$ or Z—(C1-C10 alkylene)-O—$R^5$.

55. The composition of embodiment 54, wherein —Z— is —C(O)N($R^7$)—.

56. The composition of any one of embodiments 41-55, wherein $R^6$ is C1-C5 alkyl.

57. The composition of embodiment 56, wherein $R^6$ is methyl.

58. The composition of any one of embodiments 41-57, wherein $R^7$ is H or C1-C5 alkyl.

59. The composition of embodiment 58, wherein $R^7$ is H or methyl.

60. The composition of any one of embodiments 41-59, wherein $R^8$ is H or C1-C5 alkyl.

61. The composition of embodiment 60, wherein $R^8$ is H or methyl.

62. The composition of any one of embodiments 41-61, wherein $R^9$ is H or Me.

62a. The composition of embodiment 62, wherein $R^9$ is H.

63. The composition of any one of embodiments 41-62a, wherein X is F.

64. The composition of embodiment 41, wherein the adenosine derivative is a compound having a structure of:

formula (2)
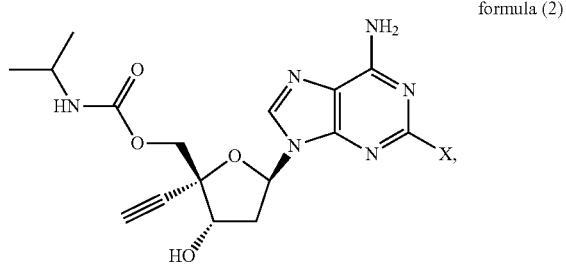

formula (3)
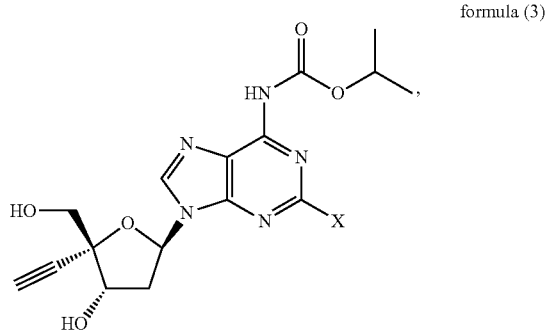

formula (4)
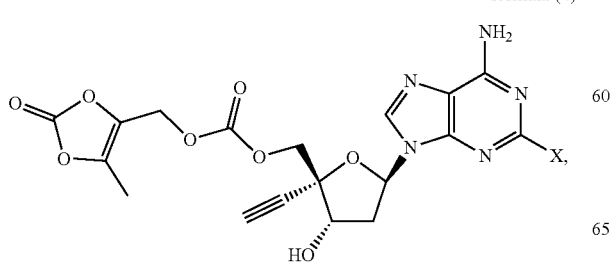

formula (5)
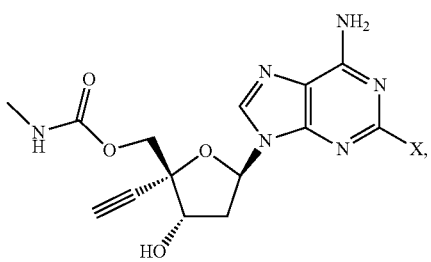

formula (6)
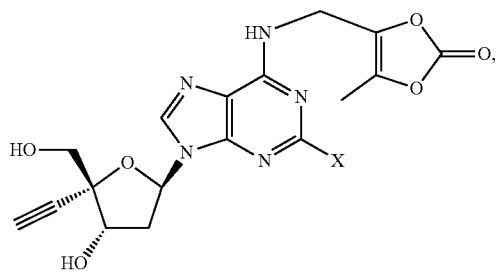

formula (7)
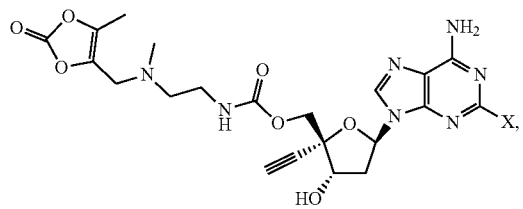

formula (8)
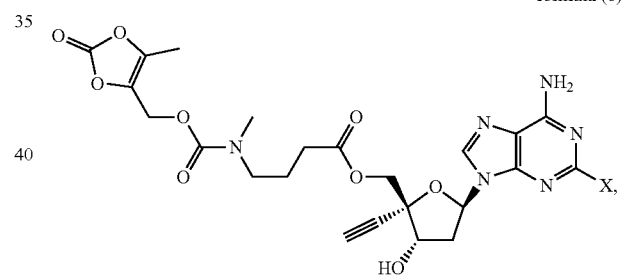

formula (4-B)

or a pharmaceutically acceptable salt, tautomer, or solvate thereof.

65. The composition of embodiment 41, wherein the adenosine derivative is a compound having a structure of:

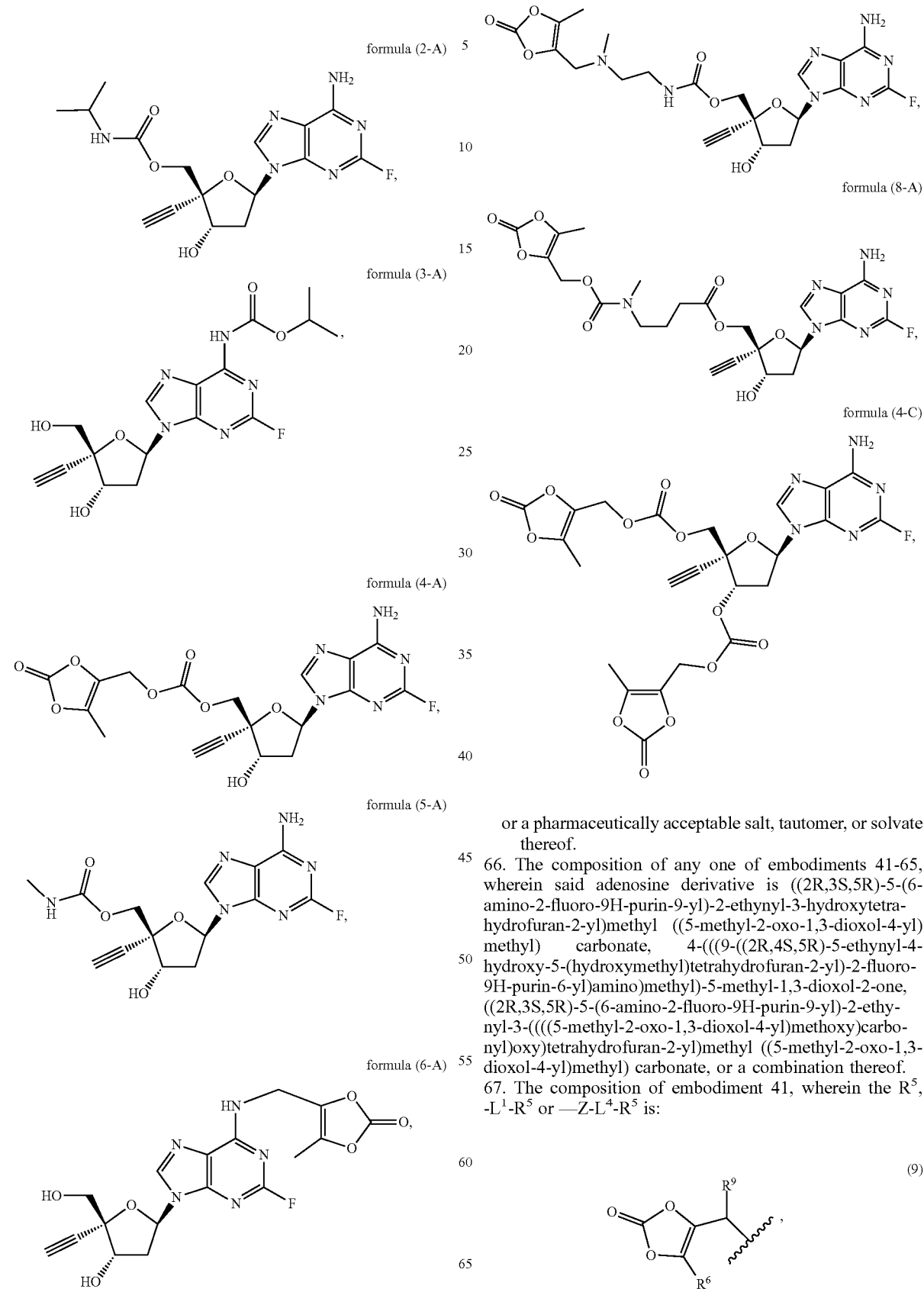

or a pharmaceutically acceptable salt, tautomer, or solvate thereof.

66. The composition of any one of embodiments 41-65, wherein said adenosine derivative is ((2R,3S,5R)-5-(6-amino-2-fluoro-9H-purin-9-yl)-2-ethynyl-3-hydroxytetrahydrofuran-2-yl)methyl ((5-methyl-2-oxo-1,3-dioxol-4-yl)methyl) carbonate, 4-(((9-((2R,4S,5R)-5-ethynyl-4-hydroxy-5-(hydroxymethyl)tetrahydrofuran-2-yl)-2-fluoro-9H-purin-6-yl)amino)methyl)-5-methyl-1,3-dioxol-2-one, ((2R,3S,5R)-5-(6-amino-2-fluoro-9H-purin-9-yl)-2-ethynyl-3-((((5-methyl-2-oxo-1,3-dioxol-4-yl)methoxy)carbonyl)oxy)tetrahydrofuran-2-yl)methyl ((5-methyl-2-oxo-1,3-dioxol-4-yl)methyl) carbonate, or a combination thereof.

67. The composition of embodiment 41, wherein the R⁵, -L¹-R⁵ or —Z-L⁴-R⁵ is:

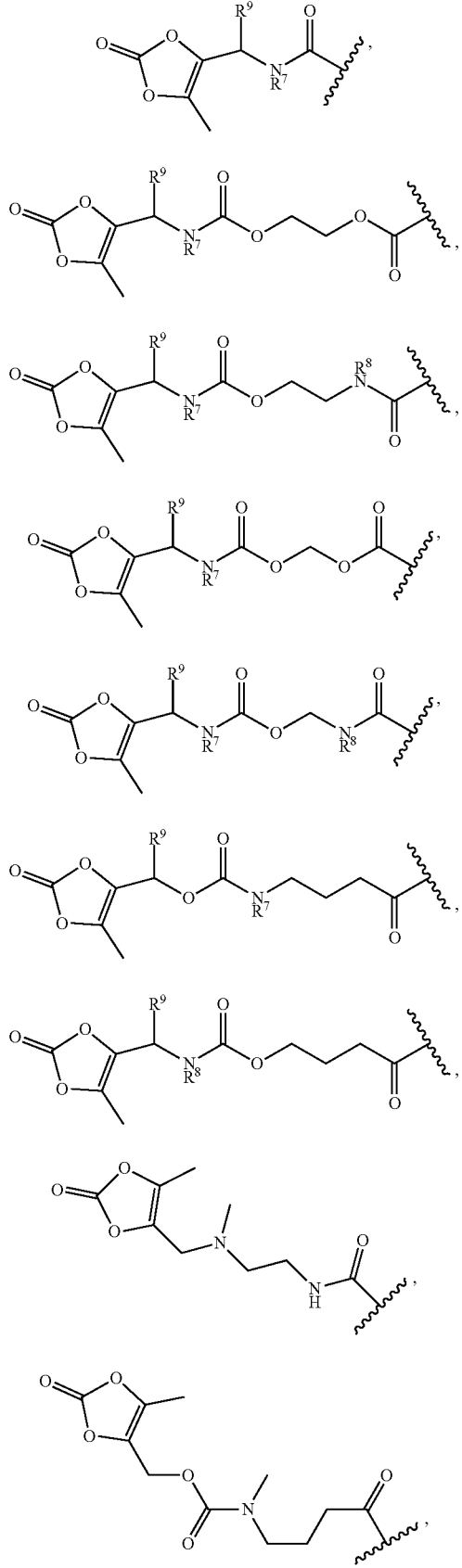
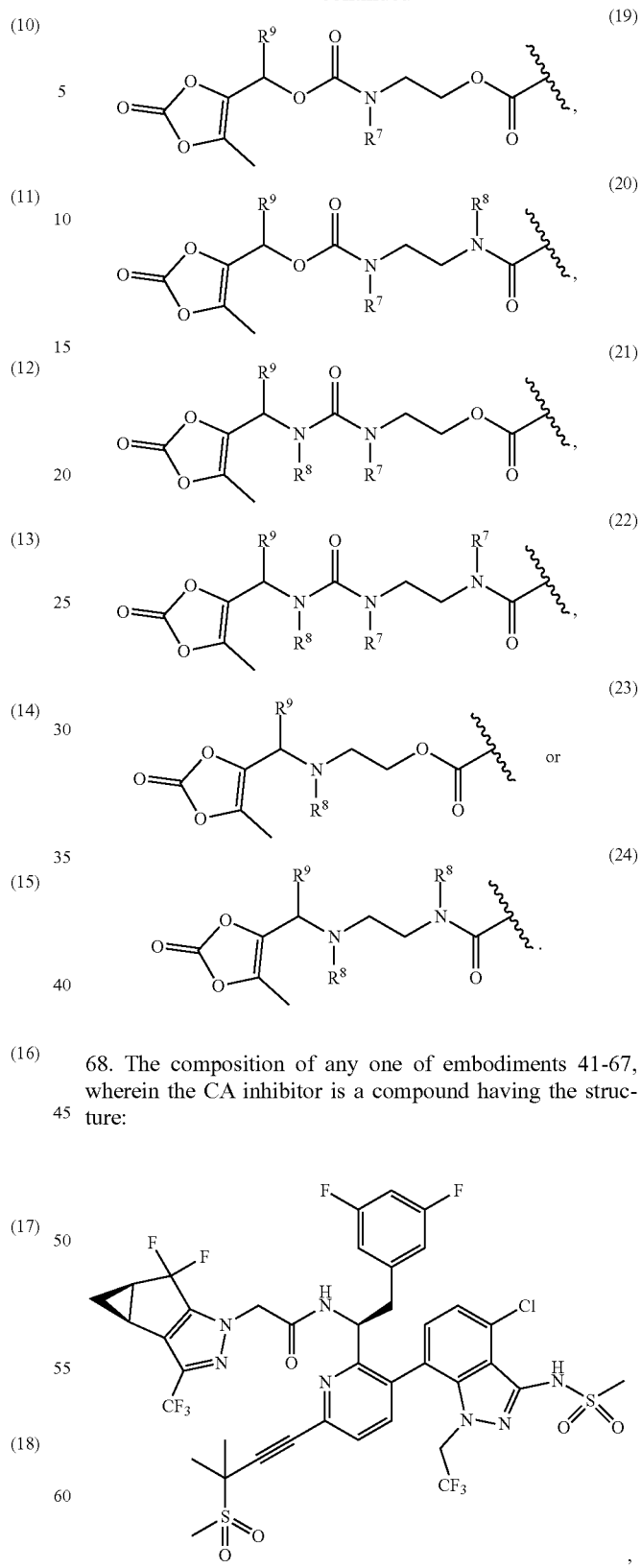
68. The composition of any one of embodiments 41-67, wherein the CA inhibitor is a compound having the structure:
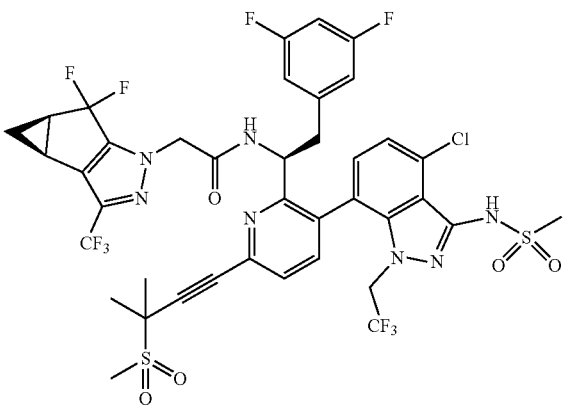
or a pharmaceutically acceptable salt or solvate thereof.
69. The composition of any one of embodiments 41-68, further comprising a pharmaceutically acceptable carrier.

70. The composition of any one of embodiments 41-69, wherein the effective dosage of the adenosine derivative is from 200 mg to 2000 mg and the effective amount of the capsid inhibitor is from 300 mg to 2000 mg.

71. The composition of any one of embodiments 41-70, wherein the pharmaceutical composition is suitable for oral administration.

72. The composition of any one of embodiments 41-70, wherein the pharmaceutical composition is suitable for parenteral administration.

73. The composition of embodiment 72, wherein the parenteral administration is by intramuscular and/or subcutaneous injection.

EXAMPLES

The present invention is further defined in the following non-limiting Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Properties of the Adenosine Derivatives of the Present Disclosure

Properties of the adenosine derivatives are listed in Table 1.

TABLE 1

Nomenclature and properties.

| Formula ID | IUPAC Nomenclature | Molecular Weight |
|---|---|---|
| T-1A (EFdA) | (2R,3S,5R)-5-(6-amino-2-fluoro-9H-purin-9-yl)-2-ethynyl-2-(hydroxymethyl)tetrahydrofuran-3-ol | 293.25 |
| 2-A | ((2R,3S,5R)-5-(6-amino-2-fluoro-9H-purin-9-yl)-2-ethynyl-3-hydroxytetrahydrofuran-2-yl)methyl isopropylcarbamate | 378.36 |
| 3-A | isopropyl (9-((2R,4S,5R)-5-ethynyl-4-hydroxy-5-(hydroxymethyl)tetrahydrofuran-2-yl)-2-fluoro-9H-purin-6-yl)carbamate | 379.34 |
| 4-A | ((2R,3S,5R)-5-(6-amino-2-fluoro-9H-purin-9-yl)-2-ethynyl-3-hydroxytetrahydrofuran-2-yl)methyl ((5-methyl-2-oxo-1,3-dioxol-4-yl)methyl) carbonate | 449.35 |
| 5-A | ((2R,3S,5R)-5-(6-amino-2-fluoro-9H-purin-9-yl)-2-ethynyl-3-hydroxytetrahydrofuran-2-yl)methyl methylcarbamate | 350.31 |
| 6-A | 4-(((9-((2R,4S,5R)-5-ethynyl-4-hydroxy-5-(hydroxymethyl)tetrahydrofuran-2-yl)-2-fluoro-9H-purin-6-yl)amino)methyl)-5-methyl-1,3-dioxol-2-one | 405.34 |
| 7-A | ((2R,3S,5R)-5-(6-amino-2-fluoro-9H-purin-9-yl)-2-ethynyl-3-hydroxytetrahydrofuran-2-yl)methyl (2-(methyl((5-methyl-2-oxo-1,3-dioxol-4-yl)methyl)amino)ethyl)carbamate | 505.46 |
| 8-A | ((2R,3S,5R)-5-(6-amino-2-fluoro-9H-purin-9-yl)-2-ethynyl-3-hydroxytetrahydrofuran-2-yl)methyl 4-(methyl(((5-methyl-2-oxo-1,3-dioxol-4-yl)methoxy)carbonyl)amino)butanoate | 662.51 |
| 4-C | ((2R,3S,5R)-5-(6-amino-2-fluoro-9H-purin-9-yl)-2-ethynyl-3-((((5-methyl-2-oxo-1,3-dioxol-4-yl)methoxy)carbonyl)oxy)tetrahydrofuran-2-yl)methyl ((5-methyl-2-oxo-1,3-dioxol-4-yl)methyl) carbonate | 605.44 |

Example 1

((2R,3S,5R)-5-(6-amino-2-fluoro-9H-purin-9-yl)-2-ethynyl-3-hydroxytetrahydrofuran-2-yl)methyl isopropylcarbamate

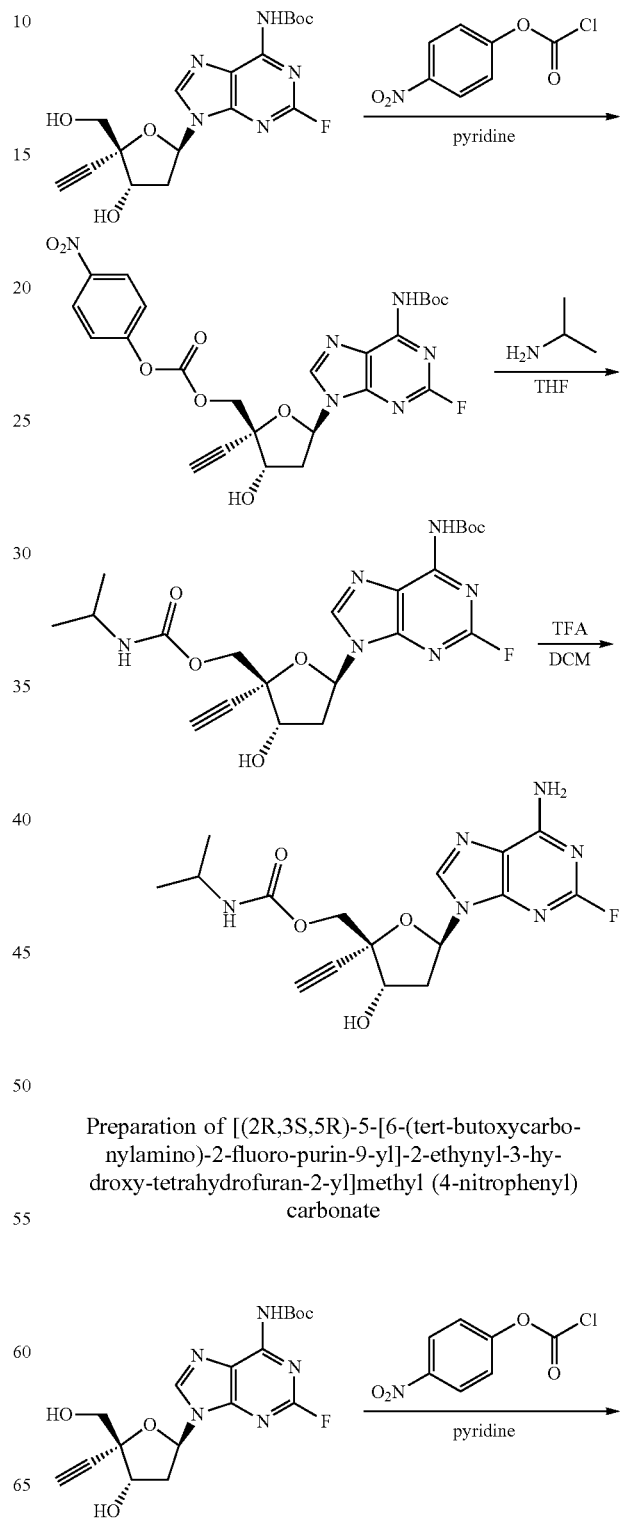

Preparation of [(2R,3S,5R)-5-[6-(tert-butoxycarbonylamino)-2-fluoro-purin-9-yl]-2-ethynyl-3-hydroxy-tetrahydrofuran-2-yl]methyl (4-nitrophenyl) carbonate

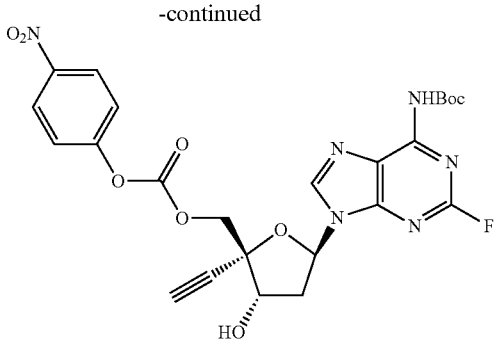

To a solution of tert-butyl N-[9-[(2R,4S,5R)-5-ethynyl-4-hydroxy-5-(hydroxymethyl)tetrahydrofuran-2-yl]-2-fluoropurin-6-yl]carbamate (80 mg, 0.203 mmol, 1 eq) in pyridine (0.8 mL) at 10° C. was added (4-nitrophenyl) carbonochloridate (41 mg, 0.203 mmol, 1 eq) at 10° C. The mixture was stirred at 10° C. for 16 hr, added water (10 mL) and extracted with EtOAc (10 mL). The organic layers were dried over Na2SO4, filtered and concentrated under reduced pressure to yield the crude product [(2R,3S,5R)-5-[6-(tert-butoxycarbonylamino)-2-fluoro-purin-9-yl]-2-ethynyl-3-hydroxy-tetrahydrofuran-2-yl]methyl (4-nitrophenyl) carbonate (114 mg, crude) as a yellow oil, which was used for next reaction without further purification. LCMS (ESI) m/z, $C_{24}H_{23}FN_6O_9$: calculated 558.2, measured (M+H)+: 559.1.

Preparation of tert-butyl N-[9-[(2R,4S,5R)-5-ethynyl-4-hydroxy-5-(isopropylcarbamoyloxymethyl)tetrahydrofuran-2-yl]-2-fluoropurin-6-yl]carbamate

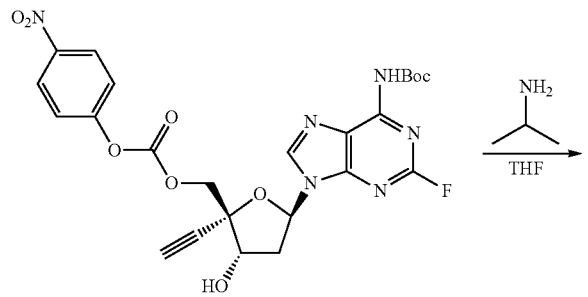

To a mixture of [(2R,3S,5R)-5-[6-(tert-butoxycarbonylamino)-2-fluoro-purin-9-yl]-2-ethynyl-3-hydroxy-tetrahydrofuran-2-yl]methyl (4-nitrophenyl) carbonate (10 mg, 0.018 mmol, 1 eq) and triethylamine (3.6 mg, 0.035 mmol, 2 eq) in THF (0.5 mL) was added propan-2-amine (1.3 mg, 0.021 mmol, 1.2 eq). The mixture was stirred at 15° C. for 2.5 hr, added water (5 mL) and extracted with EtOAc (2×10 mL). The organic layers were concentrated under reduced pressure. The crude product was purified by prep-HPLC (column: Waters Xbridge Prep OBD C18 150*30 10u; mobile phase: [water (10 mM NH4HCO3)-ACN]; B %: 15%-45%, 11 min) to give tert-butyl N-[9-[(2R,4S,5R)-5-ethynyl-4-hydroxy-5-(isopropylcarbamoyloxymethyl)tetrahydrofuran-2-yl]-2-fluoropurin-6-yl]carbamate (3.6 mg, 45.0% yield) as a white solid. LCMS (ESI) m/z, $C_{21}H_{27}FN_6O_6$: calculated 478.2, measured (M+H)+: 479.3; (M+Na)+: 501.2.

Preparation of ((2R,3S,5R)-5-(6-amino-2-fluoro-9H-purin-9-yl)-2-ethynyl-3-hydroxytetrahydrofuran-2-yl)methyl isopropylcarbamate

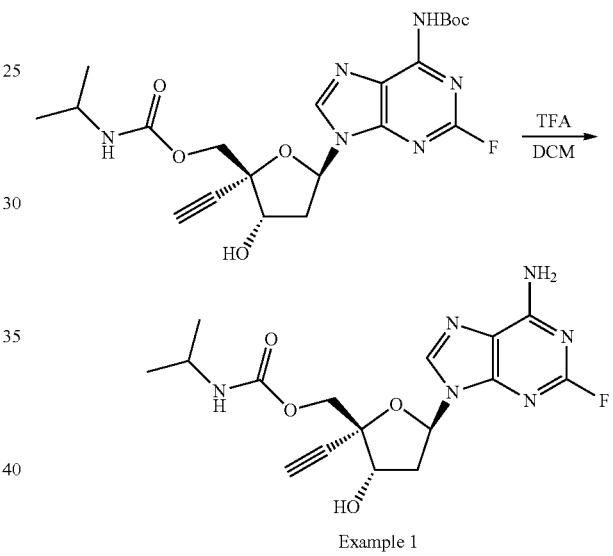

Example 1

To a solution of tert-butyl N-[9-[(2R,4S,5R)-5-ethynyl-4-hydroxy-5-(isopropylcarbamoyloxymethyl)tetrahydrofuran-2-yl]-2-fluoro-purin-6-yl]carbamate (3.6 mg, 0.0075 mmol, 1 eq) in DCM (0.5 mL) was added TFA (77 mg, 0.68 mmol, 0.05 mL, 89.8 eq) at 10° C. The mixture was stirred at 10° C. for 40 hr. The mixture was concentrated under reduced pressure and purified by prep-HPLC (column: Agela DuraShell 150 mm×25 mm×5 um; mobile phase: [water (0.05% HCl)-ACN]; B %: 10%-40%, 8 min) to give ((2R,3S,5R)-5-(6-amino-2-fluoro-9H-purin-9-yl)-2-ethynyl-3-hydroxytetrahydrofuran-2-yl)methyl isopropylcarbamate (1.2 mg, 40.0% yield) as a white solid. LCMS (ESI) m/z, $C_{16}H_{19}FN_6O_4$: calculated 378.2, measured (M+H)+: 379.3; (M+Na)+: 401.2. $^1$H NMR (400 MHz, DMSO-d6) δ (ppm) 1H NMR (DMSO-d6, 400 MHz) 8.27 (s, 1H), 7.85 (br s, 2H), 7.13 (br d, J=4.8 Hz, 1H), 6.24 (dd, J=7.6, 5.2 Hz, 1H), 4.55 (br t, J=6.8 Hz, 1H), 4.35 (br d, J=11.6 Hz, 1H), 4.00 (br d, J=11.6 Hz, 1H), 3.61 (s, 1H), 2.70-2.79 (m, 1H), 2.40-2.43 (m, 1H), 0.98-1.07 (m, 7H). $^{19}$F NMR (376 MHz, DMSO-d6) δ (ppm) −51.79 (s).

Example 2

((2R,3S,5R)-5-(6-amino-2-fluoro-9H-purin-9-yl)-2-ethynyl-3-hydroxytetrahydrofuran-2-yl)methyl methylcarbamate Preparation of ((2R,3S,5R)-5-(6-amino-2-fluoro-9H-purin-9-yl)-2-ethynyl-3-hydroxytetrahydrofuran-2-yl)methyl methylcarbamate

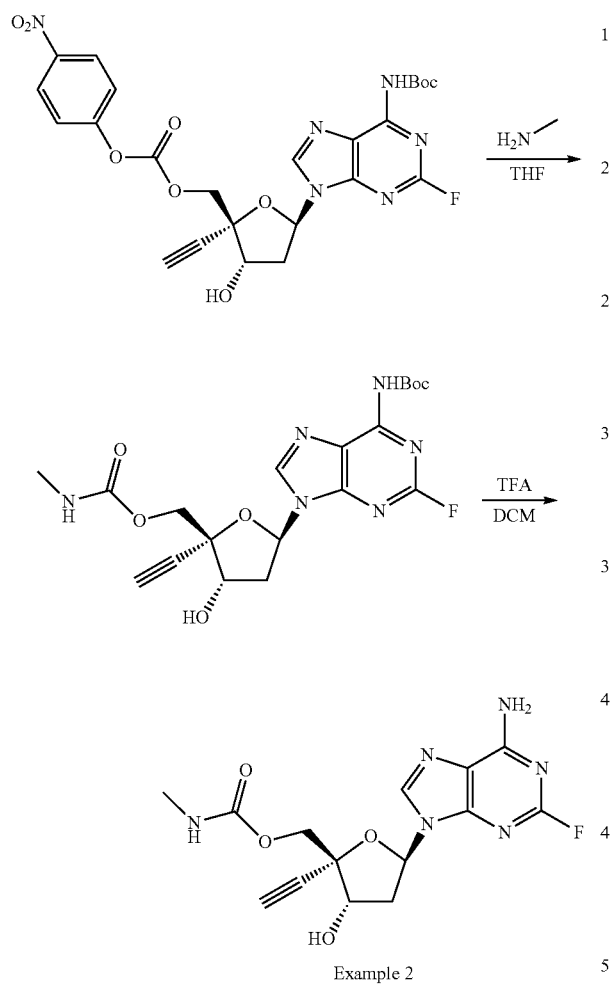

Example 2

((2R,3S,5R)-5-(6-amino-2-fluoro-9H-purin-9-yl)-2-ethynyl-3-hydroxytetrahydrofuran-2-yl)methyl methylcarbamate was prepared using the same procedure as ((2R,3S,5R)-5-(6-amino-2-fluoro-9H-purin-9-yl)-2-ethynyl-3-hydroxytetrahydrofuran-2-yl)methyl isopropylcarbamate except replacing propan-2 amine with methylamine. LCMS (ESI) m/z, $C_{14}H_{15}FN_6O_4$: calculated 350.1, measured (M+H)+: 351.2. $^1$H NMR (400 MHz, DMSO-d6) δ (ppm) 8.26 (s, 1H), 7.87 (br s, 2H), 7.13 (br d, J=4.4 Hz, 1H), 6.24 (dd, J=7.6, 5.0 Hz, 1H), 5.76 (br d, J=4.4 Hz, 1H), 4.55 (br d, J=5.2 Hz, 1H), 4.35 (d, J=11.6 Hz, 1H), 4.03 (d, J=11.6 Hz, 1H), 3.60 (s, 1H), 2.70-2.79 (m, 1H), 2.54 (s, 3H), 2.40-2.45 (m, 1H). $^{19}$F NMR (376 MHz, DMSO-d6) δ (ppm) −51.75 (s).

Example 3 isopropyl (9-((2R,4S,5R)-5-ethynyl-4-hydroxy-5-(hydroxymethyl)tetrahydrofuran-2-yl)-2-fluoro-9H-purin-6-yl)carbamate

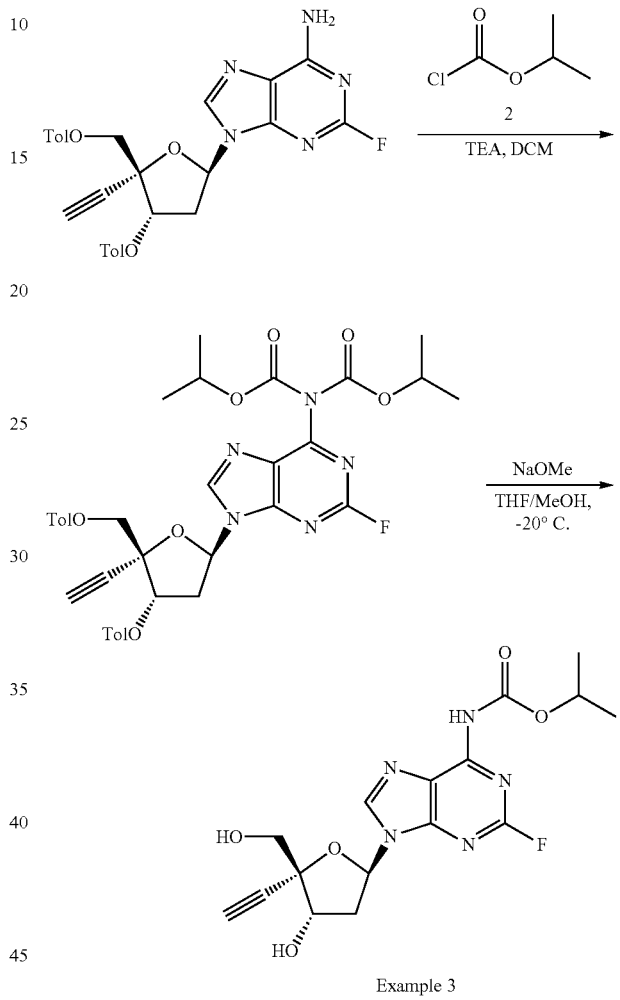

Example 3

Preparation of (2R, 3S, 5R)-5-[6-[bis(isopropoxycarbonyl)amino]-2-fluoro-9H-purin-9-yl]-2-ethynyl-2-(((4-methylbenzoyl)oxy)methyl)-tetrahydrofuran-3-yl 4-methylbenzoate

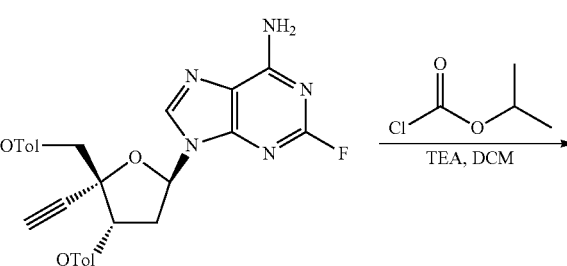

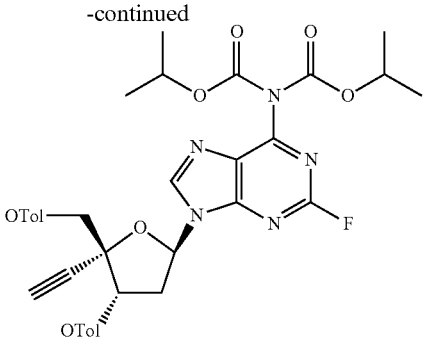

To a mixture of [(2R,3S,5R)-5-(6-amino-2-fluoro-purin-9-yl)-2-ethynyl-3-(4-methylbenzoyl)oxy-tetrahydrofuran-2-yl]methyl 4-methylbenzoate (50 mg, 0.094 mmol, 1 eq) and Et$_3$N (10 mg, 0.094 mmol, 1 eq) in DCM (1 mL) was added isopropyl carbonochloridate (23 mg, 0.19 mmol, 2 eq) at 0° C., the mixture was stirred at 15° C. for 16 hr. The mixture was concentrated under reduced pressure and 2 mL of water was added, extracted with EtOAc (10 mL×2). The combined organic layers were washed with brine (20 mL) and concentrated under reduced pressure to give (2R,3S,5R)-5-(6-(bis(isopropoxycarbonyl)amino)-2-fluoro-9H-purin-9-yl)-2-ethynyl-2-(((4-methylbenzoyl)oxy)methyl)tetrahydrofuran-3-yl 4-methylbenzoate as a crude product, which was used into the next reaction without further purification. LCMS (ESI) m/z, C$_{36}$H$_{36}$FN$_5$O$_9$: calculated 701.3, measured (M+H)$^+$: 702.1.

Preparation of isopropyl (9-((2R,4S,5R)-5-ethynyl-4-hydroxy-5-(hydroxymethyl)tetrahydrofuran-2-yl)-2-fluoro-9H-purin-6-yl)carbamate

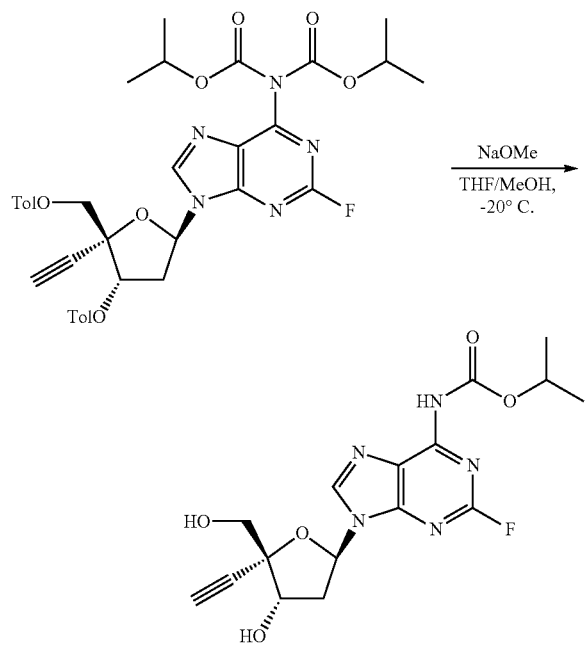

Example 3

To a solution of (2R, 3S, 5R)-5-[6-[bis(isopropoxycarbonyl)amino]-2-fluoro-9H-purin-9-yl]-2-ethynyl-2-(((4-methylbenzoyl)oxy)methyl)tetrahydrofuran-3-yl] 4-methylbenzoate (66 mg, 0.094 mmol) in THF (1 mL) was at −20° C. added NaOMe (34 mg, 0.19 mmol, 30%, 2 eq) and the resulting mixture was stirred for 16 hr at −20° C. Additional NaOMe (17 mg, 0.095 mmol, 30%, 1 eq) was added and the mixture was stirred at −20° C. for another 40 hr. The mixture was neutralized with AcOH (0.1 mL), concentrated under reduced pressure, and purified by flash silica gel chromatography (ISCO®; 4 g SepaFlash® Silica Flash Column, Eluent of 0~8% MeOH/DCM gradient @ 20 mL/min) and again by prep-HPLC (column: Waters Xbridge Prep OBD C18 150×30 5u; mobile phase: [water (10 mM NH$_4$HCO$_3$)-ACN]; B %: 5%-30%, 7 min) to give isopropyl (9-((2R,4S,5R)-5-ethynyl-4-hydroxy-5-(hydroxymethyl)tetrahydrofuran-2-yl)-2-fluoro-9H-purin-6-yl)carbamate (3.5 mg, 11% yield) as a white solid. LCMS (ESI) m/z, C$_{16}$H$_{18}$FN$_5$O$_9$: calculated 379.1 (measured (M+Na)$^+$: 402.1). $^1$H NMR (400 MHz, CDCl$_3$) δ (ppm) 8.17 (s, 1H), 7.98 (s, 2H), 6.41 (dd, J=8.8, 5.6 Hz, 1H), 5.13 (dt, J=12.4, 6.4 Hz, 1H), 5.04 (dd, J=11.0, 3.0 Hz, 1H), 4.70-4.75 (m, 1H), 4.09 (dd, J=12.4, 2.4 Hz, 1H), 3.84-3.93 (m, 1H), 3.06-3.15 (m, 1H), 2.83 (s, 1H), 2.48-2.56 (m, 2H), 1.36 (d, J=6.0 Hz, 6H). $^{19}$F NMR (376 MHz, CDCl$_3$) δ (ppm) −46.89 (s).

Example 4 (Method 1)

((2R,3S,5R)-5-(6-amino-2-fluoro-9H-purin-9-yl)-2-ethynyl-3-hydroxytetrahydrofuran-2-yl)methyl ((5-methyl-2-oxo-1,3-dioxol-4-yl)methyl) carbonate

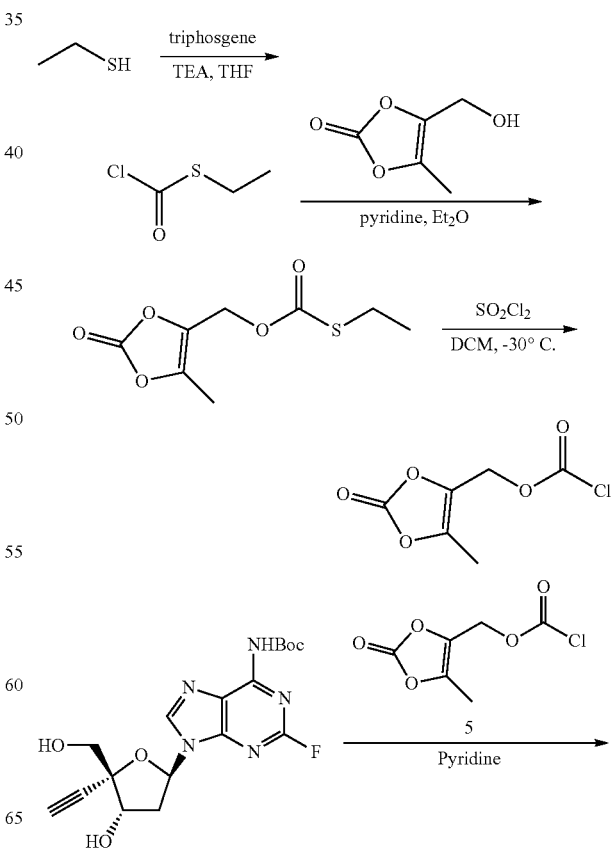

-continued

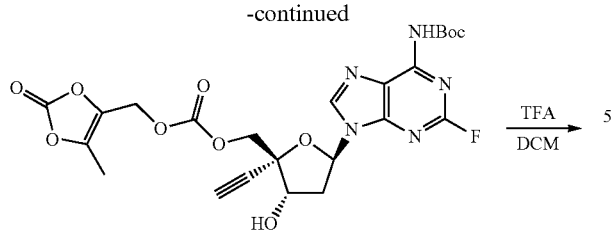

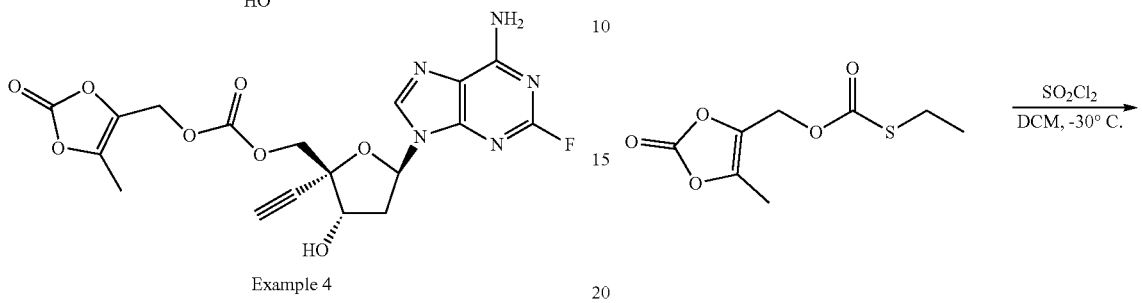

Example 4

Preparation of S-ethyl O-((5-methyl-2-oxo-1,3-di-oxol-4-yl)methyl) carbonothioate

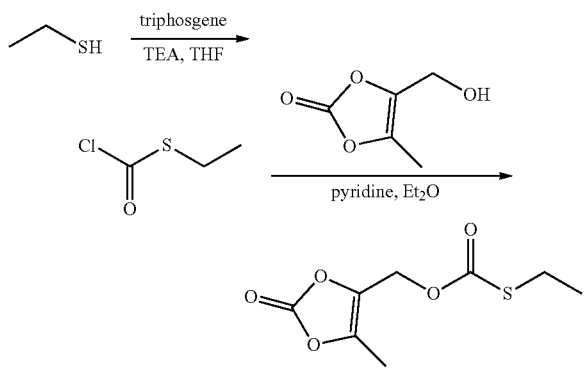

To a mixture of ethanethiol (16 g, 257.5 mmol, 19.1 mL, 1 eq), triethyl amine (26.1 g, 257.5 mmol, 35.8 mL, 1 eq) in THF (1 L) at −15° C. was added bis(trichloromethyl) carbonate (76.4 g, 257.5 mmol, 1 eq) in THF (50 mL). The mixture was warm up to 18° C. and stirred at 18° C. for 2 h. The mixture was filtered, and the filtrate was concentrated in vacuo to give S-ethyl chloromethanethioate (13 g, crude) as a yellow oil which was used for the next reaction directly without further purification.

To a mixture of 4-(hydroxymethyl)-5-methyl-1,3-dioxol-2-one (13 g, 99.9 mmol, 1 eq) in Et$_2$O (800 mL) at 0° C. was added pyridine (7.90 g, 99.9 mmol, 8.1 mL, 1 eq) and S-ethyl chloromethanethioate (12.45 g, 99.9 mmol, 1.0 eq) in Et$_2$O (200 mL), the mixture was stirred at 0° C. for 1 h and warm up to 18° C. and stirred at 18° C. for 16 h. The mixture was filtered and concentrated in vacuo, and then taken up in DCM (150 mL) and washed with sat aq. NaHCO$_3$ (150 mL×2), water (150 mL×2). The mixture was concentrated under reduced pressure and purified by flash silica gel chromatography (ISCO®; 120 g SepaFlash® Silica Flash Column, Eluent of 0~15% ethyl acetate/petroleum ether gradient @ 70 m/min) to give (5-methyl-2-oxo-1,3-dioxol-4-yl)methyl ethylsulfanylformate (9.2 g, 42.2% yield) as a light yellow oil. $^1$H NMR (400 MHz, CDCl$_3$) δ 4.95 (s, 2H), 2.89 (q, J=7.2 Hz, 2H), 2.19 (s, 3H), 1.32 (t, J=7.2 Hz, 3H).

Preparation of (5-methyl-2-oxo-1,3-dioxol-4-yl)methyl carbonochloridate

To a mixture of (5-methyl-2-oxo-1,3-dioxol-4-yl)methyl ethylsulfanylformate (500 mg, 2.29 mmol, 1 eq) in DCM (50 mL) was added sulfuryl chloride (618.5 mg, 4.58 mmol, 0.46 mL, 2 eq). The resulting mixture was stirred at 20° C. for 1 h. The reaction mixture was washed with water (50 mL×2), 5% aq Na$_2$CO$_3$ (50 mL×2), brine (50 mL), dried over Na$_2$SO$_4$, filtered and concentrated under reduced pressure to give (5-methyl-2-oxo-1,3-dioxol-4-yl)methyl carbonochloridate (350 mg, crude) as a yellow oil. The product was dissolved in 10 mL DCM and stored in refrigerator.

Preparation of tert-butyl (9-((2R,4S,5R)-5-ethynyl-4-hydroxy-5-(((((5-methyl-2-oxo-1,3-dioxol-4-yl)methoxy)carbonyl)oxy)methyl)tetrahydrofuran-2-yl)-2-fluoro-9H-purin-6-yl)carbamate

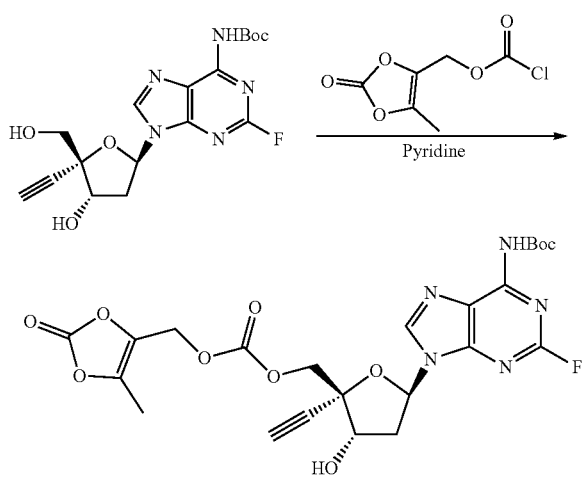

To a mixture of tert-butyl N-[9-[(2R,4S,5R)-5-ethynyl-4-hydroxy-5-(hydroxymethyl)tetrahydrofuran-2-yl]-2-fluoro-purin-6-yl]carbamate (100 mg, 0.25 nmol, 1 eq) in pyridine (2 mL) at 20° C. was added (5-methyl-2-oxo-1,3-dioxol-4-yl)methyl carbonochloridate (140 mg, 0.73 mmol, 4 mL, 2.86 eq, 35 mg/mL in DCM), the mixture was stirred at 20° C. for 16 hr. The mixture was concentrated under reduced pressure, and purified by flash silica gel chromatography (ISCO®; 4 g SepaFlash® Silica Flash Column, Eluent of 0~5% MeOH/DCM gradient @25 mL/min) to give [(2R,3S,5R)-5-[6-(tert-butoxycarbonylamino)-2-fluoro-purin-9-yl]-2-ethynyl-3-hydroxy-tetrahydrofuran-2-yl]methyl(5-methyl-2-oxo-1,3-dioxol-4-yl)methyl carbonate (45 mg, 32.2% yield) as a yellow solid. LCMS (ESI) m/z, $C_{23}H_{24}FN_5O_{10}$: calculated 549.2, measured (M+H)$^+$: 550.1.

Preparation of ((2R,3S,5R)-5-(6-amino-2-fluoro-9H-purin-9-yl)-2-ethynyl-3-hydroxytetrahydrofuran-2-yl)methyl ((5-methyl-2-oxo-1,3-dioxol-4-yl)methyl) carbonate

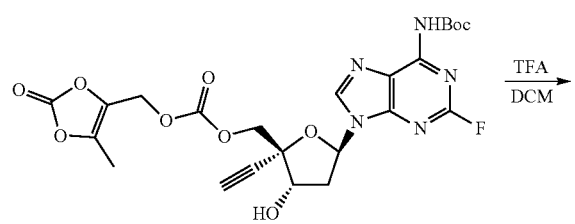

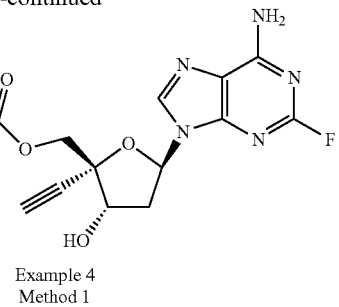

Example 4
Method 1

To a mixture of [(2R,3S,5R)-5-[6-(tert-butoxycarbonylamino)-2-fluoro-purin-9-yl]-2-ethynyl-3-hydroxy-tetrahydrofuran-2-yl]methyl(5-methyl-2-oxo-1,3-dioxol-4-yl) methyl carbonate (45 mg, 0.082 mmol, 1 eq) in toluene (1 mL) at 20° C. was added TFA (154 mg, 1.35 mmol, 0.1 mL, 16.5 eq). The mixture was stirred at 20° C. for 16 hr and then was concentrated under reduced pressure. The resulting residue was purified by prep-HPLC (column: Boston Green ODS 150×30 mm×5 um; mobile phase: [water (0.2% FA)-ACN]; B %: 13%-43%, 8 min) to give ((2R,3S,5R)-5-(6-amino-2-fluoro-9H-purin-9-yl)-2-ethynyl-3-hydroxytetrahydrofuran-2-yl)methyl ((5-methyl-2-oxo-1,3-dioxol-4-yl) methyl) carbonate (11 mg, 25.4% yield) as a white solid. LCMS (ESI) m/z, $C_{18}H_{16}FN_5O_6$: calculated 449.1, measured (M+H)$^+$: 450.1. $^{19}F$ NMR (376 MHz, CD$_3$OD) δ (ppm) −53.00 (s). $^1H$ NMR (400 MHz, CD$_3$CN) 7.92 (s, 1H), 6.41-6.21 (m, 3H), 4.87 (d, J=5.2 Hz, 2H), 4.77-4.67 (m, 1H), 4.51 (d, J=11.6 Hz, 1H), 4.30 (d, J=11.6 Hz, 1H), 3.75 (d, J=6.4 Hz, 1H), 3.00 (s, 1H), 2.89-2.81 (m, 1H), 2.61-2.52 (m, 1H), 2.10 (s, 3H).

Example 4 (Method 2)

((2R,3S,5R)-5-(6-amino-2-fluoro-9H-purin-9-yl)-2-ethynyl-3-hydroxytetrahydrofuran-2-yl)methyl ((5-methyl-2-oxo-1,3-dioxol-4-yl)methyl) carbonate

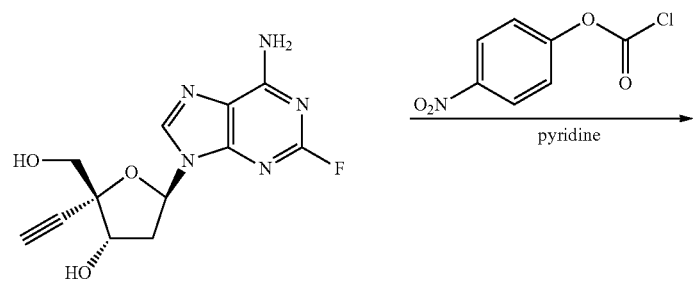

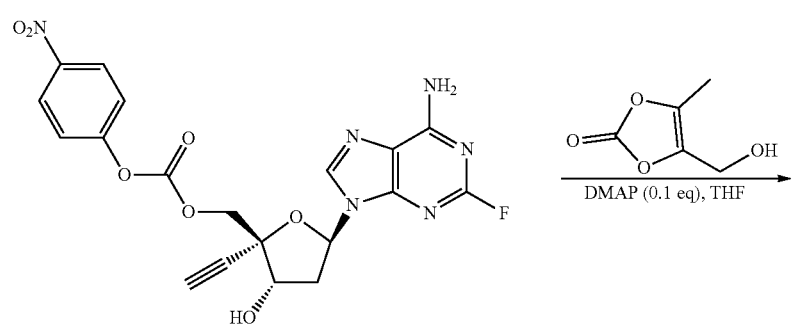

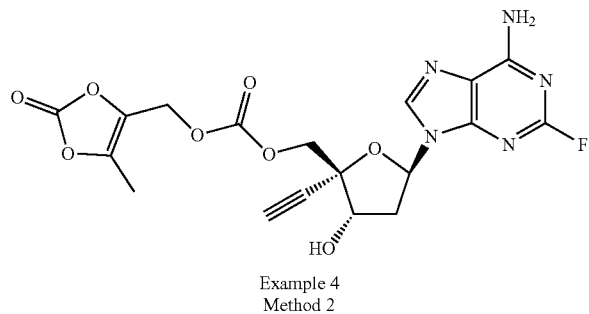

Example 4
Method 2

Preparation of ((2R,3S,5R)-5-(6-amino-2-fluoro-9H-purin-9-yl)-2-ethynyl-3-hydroxytetrahydrofuran-2-yl)methyl (4-nitrophenyl) carbonate

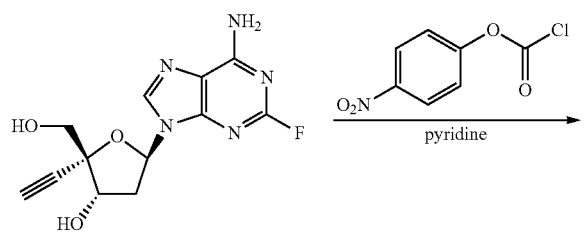

To a mixture of (2R,3S,5R)-5-(6-amino-2-fluoro-purin-9-yl)-2-ethynyl-2-(hydroxymethyl)tetrahydrofuran-3-ol (100 mg, 0.34 mmol, 1 eq) in pyridine (5 mL) was added (4-nitrophenyl) carbonochloridate (82 mg, 0.41 mmol, 1.2 eq), the mixture was stirred at 26° C. for 16 h. (4-nitrophenyl) carbonochloridate (82 mg, 0.41 mmol, 1.2 eq) was added and the mixture was stirred at 26° C. for 24 h. The reaction solution was purified by flash silica gel chromatography (ISCO®; 4 g SepaFlash® Silica Flash Column, Eluent of 0~5% DCM/MeOH gradient @ 25 mL/min) to give [(2R,3S,5R)-5-(6-amino-2-fluoro-purin-9-yl)-2-ethynyl-3-hydroxy-tetrahydrofuran-2-yl]methyl (4-nitrophenyl) carbonate (80 mg, 51.2% yield) as a white solid. LCMS (ESI) m/z, $C_{19}H_{15}FN_6O_7$: calculated 458.4, found $(M+H)^+$: 459.1.

Preparation of ((2R,3S,5R)-5-(6-amino-2-fluoro-9H-purin-9-yl)-2-ethynyl-3-hydroxytetrahydrofuran-2-yl)methyl ((5-methyl-2-oxo-1,3-dioxol-4-yl)methyl) carbonate

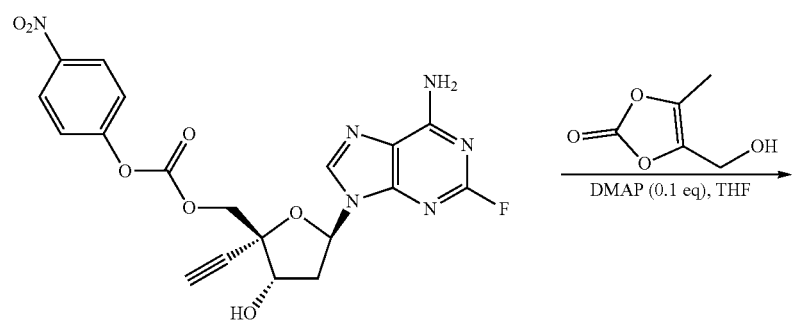

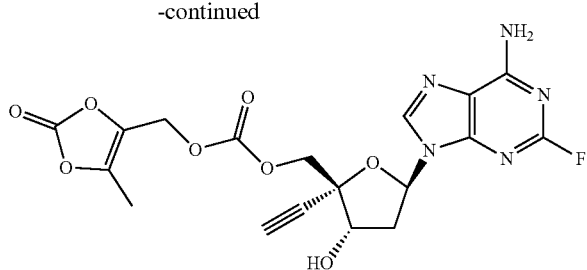

To a mixture of [(2R,3S,5R)-5-(6-amino-2-fluoro-purin-9-yl)-2-ethynyl-3-hydroxy-tetrahydrofuran-2-yl]methyl (4-nitrophenyl) carbonate (150 mg, 0.298 mmol, 1 eq) and 4-(hydroxymethyl)-5-methyl-1,3-dioxol-2-one (96 mg, 0.745 mmol, 2.5 eq) in THF (3 mL) was added DMAP (3.6 mg, 0.023 mmol, 0.1 eq), the mixture was stirred at 25° C. for 2 h. The reaction solution was purified by flash silica gel chromatography (ISCO®; 24 g SepaFlash® Silica Flash Column, Eluent of 0~2.5% DCM/MeOH gradient @ 25 mL/min) to give [(2R,3S,5R)-5-(6-amino-2-fluoro-purin-9-yl)-2-ethynyl-3-hydroxy-tetrahydrofuran-2-yl]methyl(5-methyl-2-oxo-1,3-dioxol-4-yl)methyl carbonate (85 mg, 63.5% yield) as a white solid. LCMS (ESI) m/z, $C_{18}H_{16}FN_5O_8$ calculated 449.4, found 450.1 (M+H)$^+$. $^1$H NMR (400 MHz, CD$_3$CN) δ (ppm) 7.91 (s, 1H), 6.42-6.16 (m, 3H), 4.93-4.79 (m, 2H), 4.76-4.67 (m, 1H), 4.53-4.46 (m, 1H), 4.34-4.25 (m, 1H), 3.77-3.69 (m, 1H), 3.00 (s, 1H), 2.90-2.78 (m, 1H), 2.62-2.50 (m, 1H), 2.10 (s, 3H). $^{19}$F NMR (376 MHz, CD$_3$CN) δ (ppm) −52.87 (s, 1F).

Example 4 (Method 3)

((2R,3S,5R)-5-(6-amino-2-fluoro-9H-purin-9-yl)-2-ethynyl-3-hydroxytetrahydrofuran-2-yl)methyl ((5-methyl-2-oxo-1,3-dioxol-4-yl)methyl) carbonate

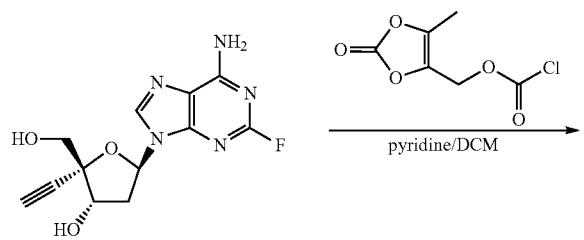

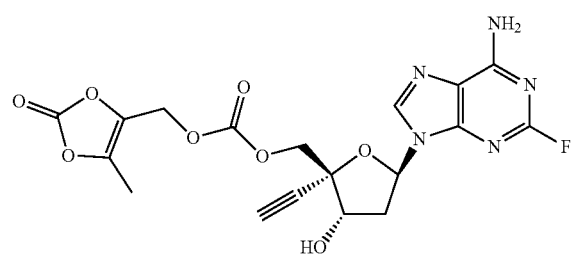

Example 4
Method 3

Preparation of ((2R,3S,5R)-5-(6-amino-2-fluoro-9H-purin-9-yl)-2-ethynyl-3-hydroxytetrahydrofuran-2-yl)methyl (4-nitrophenyl) carbonate

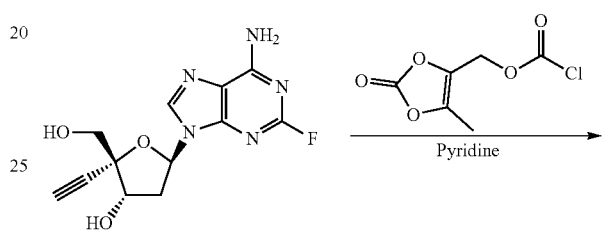

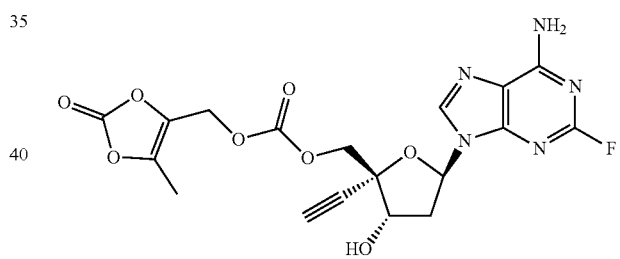

To a mixture of (2R,3S,5R)-5-(6-amino-2-fluoro-purin-9-yl)-2-ethynyl-2-(hydroxymethyl)tetrahydrofuran-3-ol (5 g, 17.05 mmol, 1 eq) in pyridine (50 mL) was dropwise added (5-methyl-2-oxo-1,3-dioxol-4-yl)methyl carbonochloridate (16.42 g, 85.25 mmol, 5 eq) in DCM (16 mL) at 0° C. over a period of 2 h, after that the mixture was stirred at 16° C. for 10 min. The mixture was diluted with DCM (200 mL) and washed with water (150 mL), brine (150 mL×2), dried over Na$_2$SO$_4$, filtered and concentrated. The resulting residue was purified by flash silica gel chromatography (ISCO®; 80 g SepaFlash® Silica Flash Column, Eluent of 0~5% MeOH/DCM gradient @ 65 mL/min) to give [(2R,3S,5R)-5-(6-amino-2-fluoro-purin-9-yl)-2-ethynyl-3-hydroxy-tetrahydrofuran-2-yl]methyl (5-methyl-2-oxo-1,3-dioxol-4-yl)methyl carbonate (5.10 g, 11.35 mmol, 66.6% yield) as a light yellow solid. LCMS (ESI) m/z, $C_{18}H_{16}FN_5O_8$: calculated 449.4, found (M+H)$^+$: 450.1. $^1$H NMR (400 MHz, CD$_3$CN) δ (ppm) 7.92 (s, 1H), 6.34 (br s, 2H), 6.29-6.23 (m, 1H), 4.93-4.81 (m, 2H), 4.77-4.69 (m, 1H), 4.51 (d, J=11.6 Hz, 1H), 4.30 (d, J=11.6 Hz, 1H), 3.74 (d, J=6.4 Hz, 1H), 3.00 (s, 1H), 2.91-2.79 (m, 1H), 2.62-2.51 (m, 1H), 2.10 (s, 3H). $^{19}$F NMR (376 MHz, CD$_3$CN) δ (ppm) −52.84 (s, 1F).

Recrystallization of ((2R,3S,5R)-5-(6-amino-2-fluoro-9H-purin-9-yl)-2-ethynyl-3-hydroxytetrahydrofuran-2-yl)methyl (4-nitrophenyl) carbonate

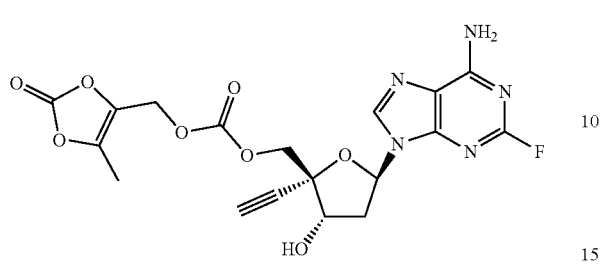

A mixture of [(2R,3S,5R)-5-(6-amino-2-fluoro-purin-9-yl)-2-ethynyl-3-hydroxy-tetrahydrofuran-2-yl]methyl-(5-methyl-2-oxo-1,3-dioxol-4-yl)methyl carbonate (9.5 g, 21.14 mmol, 1 eq) in MeCN (50 mL) and EtOAc (50 mL) was heated at 80° C. for 30 min and dissolution of the solids was observed. After cooling to room temperature (20° C.), the mixture was stirred at 20° C. for 16 h. The mixture was filtered and the filter cake was dried in vacuum to give [(2R,3S,5R)-5-(6-amino-2-fluoro-purin-9-yl)-2-ethynyl-3-hydroxy-tetrahydrofuran-2-yl]methyl (5-methyl-2-oxo-1,3-dioxol-4-yl)methyl carbonate (8.0 g, 17.80 mmol, 84.2% yield) as a white solid. LCMS (ESI) m z, $C_{18}H_{16}FN_5O_8$: calculated 449.4, found (M+H)$^+$: 450.1. $^1$H NMR (400 MHz, CD$_3$CN) δ (ppm) 7.92 (s, 1H), 6.31 (br s, 2H), 6.27-6.24 (m, 1H), 4.92-4.81 (m, 2H), 4.77-4.69 (m, 1H), 4.51 (d, J=11.6 Hz, 1H), 4.30 (d, J=11.6 Hz, 1H), 3.73 (d, J=6.4 Hz, 1H), 3.00 (s, 1H), 2.89-2.81 (m, 1H), 2.62-2.51 (m, 1H), 2.10 (s, 3H). $^{19}$F NMR (376 MHz, CD$_3$CN) δ (ppm) −52.84 (s, 1F).

Example 5 (Method 1)

4-(((9-((2R,4S,5R)-5-ethynyl-4-hydroxy-5-(hydroxymethyl)tetrahydrofuran-2-yl)-2-fluoro-9H-purin-6-yl)amino)methyl)-5-methyl-1,3-dioxol-2-one

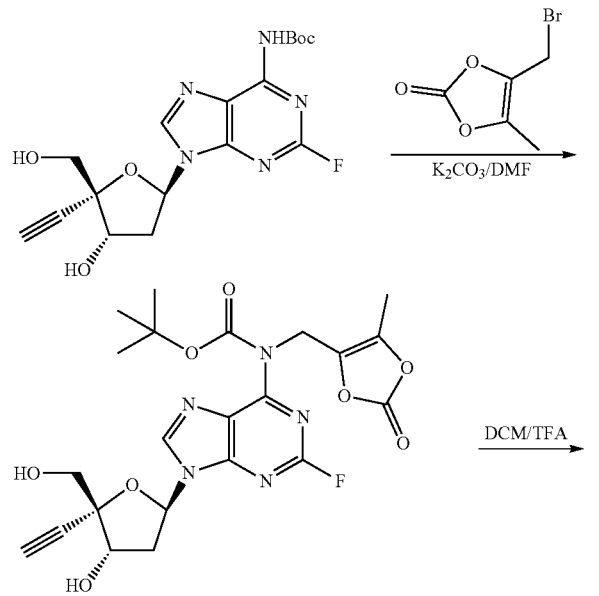

Example 5
Method 1

Preparation of tert-butyl(9-((2R,4S,5R)-5-ethynyl-4-hydroxy-5-(hydroxymethyl)tetrahydrofuran-2-yl)-2-fluoro-9H-purin-6-yl)((5-methyl-2-oxo-1,3-dioxol-4-yl)methyl)carbamate

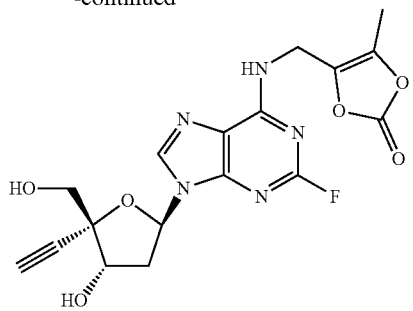

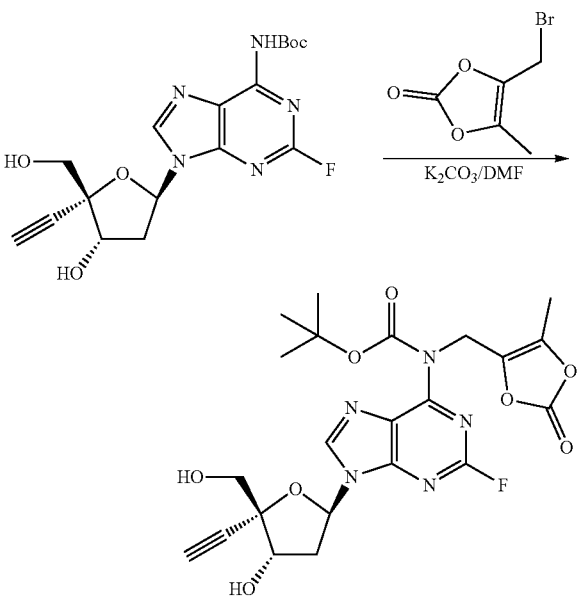

To a mixture of tert-butyl N-[9-[(2R,4S,5R)-5-ethynyl-4-hydroxy-5-(hydroxymethyl)tetrahydrofuran-2-yl]-2-fluoro-purin-6-yl]carbamate (100 mg, 0.25 nmol, 1 eq) in DMF (5 mL) was added K$_2$CO$_3$ (70 mg, 0.51 mmol, 2 eq) and 4-(bromomethyl)-5-methyl-1,3-dioxol-2-one (147 mg, 0.76 mmol, 3 eq). The reaction mixture was then heated at 60° C. for 12 hr, concentrated and then diluted with H$_2$O (30 mL). The resulting mixture was extracted with EtOAc (30×3 mL). The combined organic layers were washed with brine (50 mL), dried over Na2SO$_4$, filtered and concentrated. The resulting residue was purified by flash silica gel chromatography (ISCO®; 4 g SepaFlash® Silica Flash Column, Eluent of 0~10% methanol/dichloromethane gradient @30 mL/min) to give tert-butyl N-[9-[(2R,4S,5R)-5-ethynyl-4-hydroxy-5-(hydroxymethyl)tetrahydrofuran-2-yl]-2-fluoro-purin-6-yl]-N-[(5-methyl-2-oxo-1,3-dioxol-4-yl)methyl] carbamate (45 mg, 35.0% yield) as a light yellow oil. $^1$H NMR (400 MHz, CDCl$_3$) δ (ppm) 8.02 (s, 1H), 6.40-6.43 (m, 1H), 5.02 (s, 2H), 4.70-4.73 (m, 2H), 4.09 (d, J=12 Hz, 1H), 3.90-3.92 (m, 1H), 3.11-3.14 (m, 1H), 2.85 (s, 1H), 2.50-2.55 (m, 1H), 2.45 (bs, 1H), 2.22 (s, 3H), 1.53 (s, 9H).

Preparation of 4-(((9-((2R,4S,5R)-5-ethynyl-4-hydroxy-5-(hydroxymethyl)tetrahydrofuran-2-yl)-2-fluoro-9H-purin-6-yl)amino)methyl)-5-methyl-1,3-dioxol-2-one

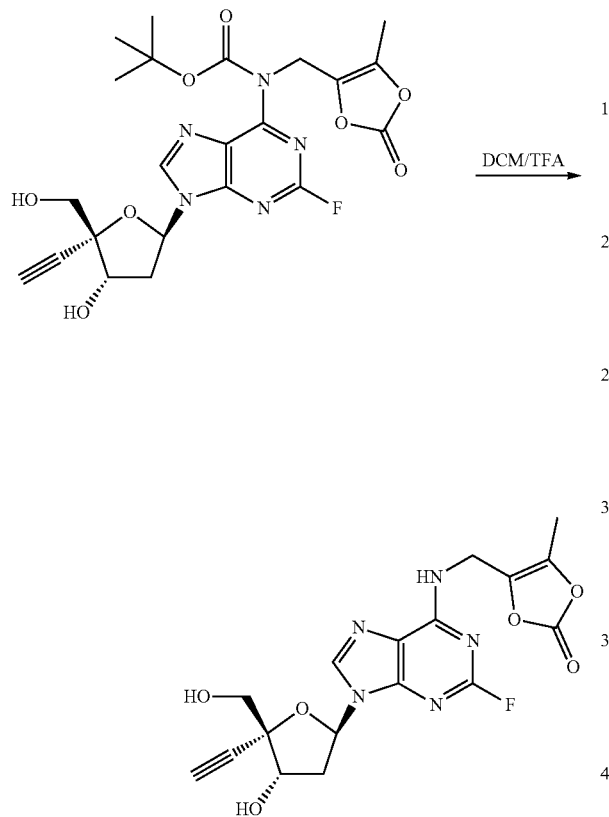

Example 5
Method 1

To a solution of tert-butyl N-[9-[(2R,4S,5R)-5-ethynyl-4-hydroxy-5-(hydroxymethyl)tetrahydrofuran-2-yl]-2-fluoro-purin-6-yl]-N-[(5-methyl-2-oxo-1,3-dioxol-4-yl)methyl]carbamate (40 mg, 0.079 mmol, 1 eq) in dichloromethane (DCM) (3 mL) at 25° C. was added TFA (0.5 mL). The mixture was stirred at 25° C. for 12 hr. The reaction mixture was concentrated and purified by prep-HPLC (column: Boston Green ODS 150*30 mm*5 um; mobile phase: [water (0.2% FA)-ACN]; B %: 15%-45%, 8 min) to give 4-(((9-((2R,4S,5R)-5-ethynyl-4-hydroxy-5-(hydroxymethyl)tetrahydrofuran-2-yl)-2-fluoro-9H-purin-6-yl)amino)methyl)-5-methyl-1,3-dioxol-2-one (1.7 mg, 5% yield) as a white solid. LCMS (ESI) m/z, $C_{17}H_{16}FN_5O_6$: calculated 405.1, measured (M+H)+: 406.1. (M+Na)+: 428.1. $^1$H NMR (400 MHz, $CD_3OD$) δ (ppm) 8.26 (s, 1H), 6.38-6.35 (m, 1H), 4.76-4.72 (m, 1H), 4.51 (s, 1H), 3.87-3.84 (d, J=12 Hz, 1H), 3.78-3.75 (d, J=12 Hz, 1H), 3.09 (s, 2H), 2.80-2.75 (m, 1H), 2.64-2.57 (m, 1H), 2.24 (s, 3H). $^{19}$F NMR (376 MHz, $CD_3OD$) δ (ppm) −53.00.

Example 5 (Method 2)

4-(((9-((2R,4S,5R)-5-ethynyl-4-hydroxy-5-(hydroxymethyl)tetrahydrofuran-2-yl)-2-fluoro-9H-purin-6-yl)amino)methyl)-5-methyl-1,3-dioxol-2-one

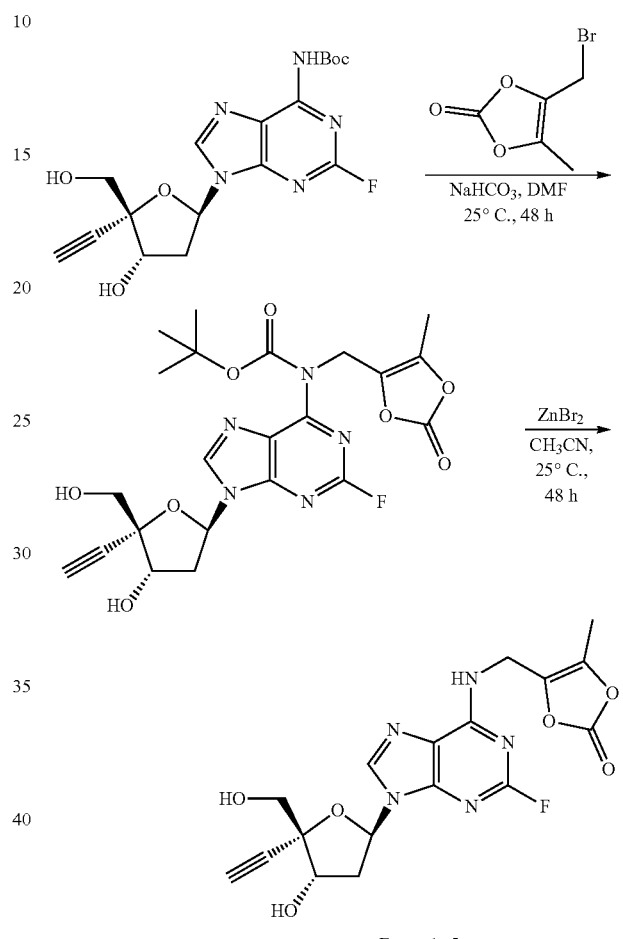

Example 5
Method 2

Preparation of tert-butyl-N-[9-[(2R,4S,5R)-5-ethynyl-4-hydroxy-5-(hydroxymethyl)tetrahydrofuran-2-yl]-2-fluoro-purin-6-yl]-N-[(5-methyl-2-oxo-1,3-dioxol-4-yl)methyl]carbamate

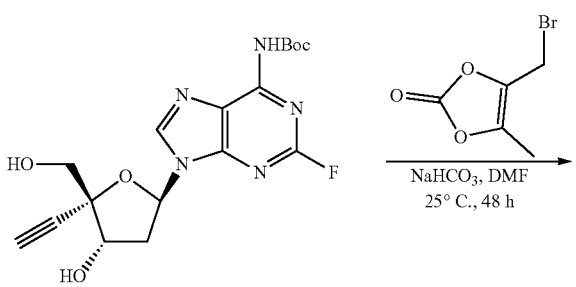

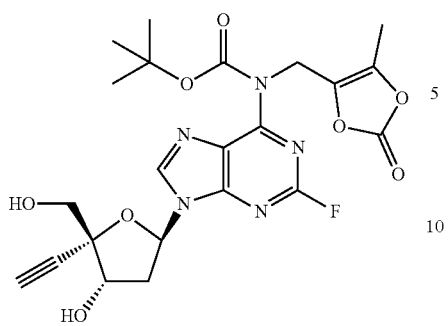

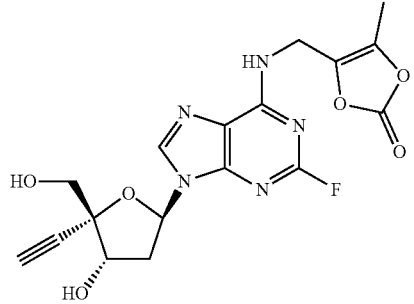

Example 5
Method 2

To a solution of tert-butyl N-[9-[(2R,4S,5R)-5-ethynyl-4-hydroxy-5-(hydroxymethyl) tetrahydrofuran-2-yl]-2-fluoro-purin-6-yl]carbamate (300 mg, 0.76 mmol, 1 eq) in DMF (5 mL) was added NaHCO$_3$ (128 mg, 1.52 mmol, 2 eq), then 4-(bromomethyl)-5-methyl-1,3-dioxol-2-one (294 mg, 1.52 mmol, 2 eq) was added. The mixture was stirred at 25° C. for 48 h. The mixture was concentrated. The resulting residue was purified by flash silica gel chromatography (ISCO®; 4 g SepaFlash® Silica Flash Column, eluent with 0~100% ethyl acetate/petroleum ether gradient @ 20 mL/min) to give tert-butyl N-[9-[(2R,4S, 5R)-5ethynyl-4-hydroxy-5-(hydroxymethyl)tetrahydrofuran-2-yl]-2-fluoro-purin-6-yl]-N-[(5-methyl-2-oxo-1,3-dioxol-4-yl)methyl] carbamate (200 mg, 52% yield) as a white solid. $^1$H NMR (400 MHz, CDCl$_3$) δ (ppm) 7.98 (s, 1H), 6.45-6.33 (m, 1H), 4.99 (s, 1H), 5.03-4.94 (m, 1H), 4.78 (br d, J=11.2 Hz, 1H), 4.71 (br s, 1H), 4.16-4.02 (m, 2H), 3.11 (br s, 1H), 2.80 (s, 1H), 2.49 (br d, J=7.2 Hz, 1H), 2.42 (br s, 1H), 2.19 (s, 3H), 1.55 (s, 9H).

Preparation of 4-[[[9-[(2R,4S,5R)-5-ethynyl-4-hydroxy-5-(hydroxymethyl)tetrahydrofuran-2-yl]-2-fluoro-purin-6-yl]amino]methyl]-5-methyl-1,3-dioxol-2-one To a solution of tert-butyl N-[9-[(2R,4S,5R)-5-ethynyl-4-hydroxy-5-(hydroxymethyl) tetrahydrofuran-2-yl]-2-fluoro-purin-6-yl]-N-[(5-methyl-2-oxo-1,3-dioxol-4-yl)methyl] carbamate (50 mg, 0.10 mmol, 1 eq) in CH$_3$CN (5 mL) was added ZnBr$_2$ (45 mg, 0.20 mmol, 2 eq). The mixture was stirred at 25° C. for 48 h. The reaction was filtered, and the filtrate was concentrated. The resulting residue was purified by prep-HPLC (FA condition; column: 3_Phenomenex Luna C18 75×30 mm×3 um; mobile phase: [water (0.2% FA)-ACN]; B %: 22%-52%, 6 min) to give 4-[[[9-[(2R,4S,5R)-5-ethynyl-4-hydroxy-5-(hydroxymethyl)tetrahydrofuran-2-yl]-2-fluoro-purin-6-yl]amino]methyl]-5-methyl-1,3-dioxol-2-one (19.8 mg, 48.8% yield) as a white solid. LCMS (ESI) m/z, C$_{17}$H$_{16}$FN$_5$O$_6$: calculated 405.34, found (M+H)$^+$: 406.1. $^1$H NMR (400 MHz, CD$_3$OD) δ (ppm) 8.26 (s, 1H), 6.38-6.35 (m, 1H), 4.76-4.72 (m, 1H), 4.51 (br s, 2H), 3.87-3.84 (d, J=12 Hz, 1H), 3.78-3.75 (d, J=12 Hz, 1H), 3.09 (s, 1H), 2.80-2.75 (m, 1H), 2.64-2.57 (m, 1H), 2.24 (s, 3H). $^{19}$F NMR (376 MHz, CD$_3$OD) δ (ppm) −52.33.

Example 6

Conversion and Stability of the Adenosine Derivative Prodrugs

Stability of prodrugs and conversion of the prodrugs to the target drug adenosine derivative (EFdA) (formula T-1A) was measured in both plasma and liver S9 assays and the data are shown in Table 2.

Plasma Stability

The pooled frozen plasma was thawed in a water bath at 37° C. prior to experiment. Plasma was centrifuged at 4000 rpm for 5 min and the clots were removed if any. The pH will be adjusted to 7.4±0.1 if required.

Preparation of test compounds and positive control (propantheline bromide): 1 mM intermediate solution was prepared by diluting 10 μL of the stock solution with 90 μL MeOH; 1 mM intermediate of positive control Propantheline was prepared by diluting 10 μL of the stock solution with 90 μL ultrapure water. 100 μM dosing solution was prepared by diluting 20 μL of the intermediate solution (1 mM) with 180 μL MeOH. 98 μL of blank plasma was spiked with 2 μL of dosing solution (100 μM) to achieve 2 μM of the final concentration in duplicate and samples were incubated at 37° C. in a water bath. At each time point (0, 10, 30, 60 and 120 min), 400 μL of stop solution (0.1% FA in MeOH containing 200 ng/mL tolbutamide and 200 ng/mL Labetalol) was added to precipitate protein and mixed thoroughly. Centrifuged sample plates at 4,000 rpm for 10

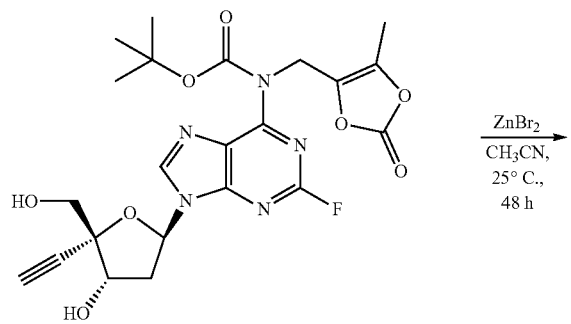

min. An aliquot of supernatant (100 µL) was transferred from each well to another plates.

Data analysis: The % remaining of test compound after incubation in plasma was calculated using following equation:

% Remaining=100×(PAR at appointed incubation time/PAR at T0 time)

where PAR is the peak area ratio of analyte versus internal standard (IS) (LC/MS/MS mobile phase condition: 0.1% Formic Acid in Water/0.1% Formic Acid in Acetonitrile. The appointed incubation time points are T0 (0 min), Tn (n=0, 10, 30, 60, 120 min).

Liver S9 Stability

Intermediate solution: Dilute 5 µL of compounds or controls (7-ethoxycoumarin) from stock solution (10 mM) with 495 µL MeOH (Conc.: 100 µM, 1% DMSO, 99% MeOH). Stop solution: Cold ACN (including 100 ng/mL Tolbutamide and Labetalol as internal standard). Add 2 µL test compound or control working solution/well to all plates (T0, T5, T10, T20, T30, T60, NCF60) except matrix blank. Add 600 µL/well stop solution (cold in 4° C., including 100 ng/mL Tolbutamide/100 ng/mL Labetalol) to terminate the T0 plate, then put it on ice. Dispense 840 µL/well S9 solution to 96-well plate as reservoir according to plate map. Then add 100 µL/well to every plate by Apricot. Incubate S9 solution and compound at 37° C. for about 10 min except NCF60 and T0. After adding S9 solution and 98 µLPB buffer to NCF60, incubate at 37° C. without pre-warming, start timer 1. After 60 min, add 600 µL/well stop solution to terminate the reaction. After pre-warming, dispense 760 µL/well cofactor solution to 96-well plate as reservoir according to plate map. Then add 98 µL/well to every plate by Apricot to start reaction. Incubate at 37° C., start timer 2, Add 600 µL/well stop solution (cold in 4° C., including 100 ng/mL Tolbutamide and Labetalol) to terminate the reaction. Samples are centrifuged at 4000 rpm for 20 min. While centrifuging, load 8×new 96-well plate with 300 µL HPLC water, then transfer 100 µL supernatant, mix with water for LC/MS/MS, transferred to Bioanalytical Services for LC-MS/MS analysis. Use equation of first order kinetics to calculate $t_{1/2}$ and CL: Equation of first order kinetics:

$$C_t = C_0 \cdot e^{-k_e \cdot t}$$
$$C_t = \frac{1}{2}C_0, T_{1/2} = \frac{Ln\ 2}{-k_e} = \frac{0.693}{-k_e}$$
$$CL_{int(S9)} = Vd \cdot k_e$$
$$Vd = 1\ mL/mg$$

The stability results of exemplary compounds in human plasm and human liver S9 are listed in Table 2 below.

TABLE 2

Conversion and Half Life Data.

| Formula | Stability in Human Plasma | | Stability in Human Liver S9 | |
|---|---|---|---|---|
| | Half-life | Formation of EFdA | Half-life | Formation of EFdA |
| 2-A | A | No | B | No |
| 3-A | A | No | B | No |
| 4-A | C | Yes | C | Yes |
| 5-A | A | No | B | No |
| 6-A | C | No | C | Yes |
| 7-A | B | No | C | No |
| 4-C | C | Yes | C | Yes |

Half-life ranges: A: >200 minutes; B: 50-200 minutes; C: <50 minutes.

Data showed that adenosine derivative 4-A and 4-C can be converted to the target drug efficiently in human plasma and liver S9 assays, and 6-A can be converted to the target drug efficiently in liver S9 assay.

Example 7

Antiviral Activity of Prodrugs in Two-Drug Combination Study with Lenacapavir (GS-6207)

Antiviral Activity in Two-Drug Combination with Lenacapavir (GS-6207) Against HIV-1 Laboratory Strain HIV-1 NL4-3 in MT-4 Cells.

Method Compound Preparation: Compound stock solutions (10 mM in DMSO) of prodrug formula 4-A and lenacapavir were prepared and aliquoted. The stocks were stored at −20° C. until the day of assays. Compound stock solutions were used to generate fresh working drug dilutions on each day of assay setup. Each aliquot of compound stock solutions was for single use only and discarded after experiments. Assay working dilutions were made fresh for each experiment from a previously unused aliquot of the stock solutions to avoid compound degradation. Each dilution of formula 4-A was tested in combination with five dilutions of a second anti-HIV drug, capsid inhibitor lenacapavir. In all cases the final DMSO concentration was <0.25%, which has been previously shown to have no effect in the described assays.

Virus Strains and Cell Line: The viruses and cell lines utilized for these evaluations were obtained from the NIH AIDS Research and Reference Reagent Program (Germantown, Maryland). Evaluations were performed using a cytoprotection (CPE) assay.

For each antiviral assay, a pre-titered aliquot of virus was removed from freezer (−80° C.) and quickly thawed. The virus was resuspended and diluted into tissue culture medium such that the amount of virus added to each well was the amount determined to yield 85 to 95% loss of cell viability (CPE assays) due to virus-induced cytopathic effects.

Antiviral Efficacy Assay in MT4 T Cells: MT4 cells were passaged in T-75 flasks prior to use in the antiviral assay. On the day preceding the assay, the cells were split 1:2 to assure they were in an exponential growth phase at the time of infection. Total cell and viability quantifications were performed using a hemacytometer and trypan blue exclusion assay. Cell viability needed to be greater than 95% for the cells to be utilized in the assay. The cells were re-suspended in tissue culture medium and added to the drug-containing microtiter plates in a volume of 110 µl/well and at a seeding density of $5.0 \times 10^3$ cells/well.

For each assay, a pre-titered aliquot of HIV-1 NL4-3 virus was removed from freezer (−80° C.) and allowed to thaw slowly to room temperature in a biological safety cabinet. The virus was re-suspended and diluted into tissue culture medium such that the amount of virus added to each well, in a volume of 50 μL, was the amount determined to give between 85 to 95% cell killing at six days post-infection. $TCID_{50}$ calculations by endpoint titration in MT4 cells indicated that the multiplicity of infection of these assays was approximately 0.01.

A checkerboard plate format was used to test five concentrations of lenacapavir in all possible combinations with eight concentrations of formula 4-A. The combination antiviral efficacy was evaluated on three identical assay plates (i.e., triplicate measurements) that included cell control wells (cells only) and virus control wells (cells plus virus). Combination cytotoxicity was evaluated in parallel on two identical assay plates (i.e., duplicate measurements) that included cell control wells. A compound color control plate was included for background subtraction when color was observed at the concentrations of compound used in the experiments. Antiviral efficacy and cellular toxicity were monitored by MTS staining at the experimental endpoint.

MTS Staining for Cell Viability: At assay termination, the assay plates were stained with the soluble tetrazolium-based dye MTS reagent (CellTiter®96 Reagent, Promega under respective registered trademark) to determine cell viability and quantify compound toxicity. MTS is metabolized by the mitochondria enzymes of metabolically active cells to yield a soluble formazan product, allowing the rapid quantitative analysis of cell viability and compound cytotoxicity. At termination of the assay, 20 μL of MTS reagent was added per well and the microtiter plates were then incubated for 4-6 hours at 37° C., 5% $CO_2$ for the HIV cytoprotection assay; the incubation intervals were chosen based on empirically determined times for optimal dye reduction. Adhesive plate sealers were used in place of the lids, the sealed plates were inverted several times to mix the soluble formazan product and the plates were read spectrophotometrically at 490/650 nm with a Molecular Devices SpectraMax i3 plate reader.

Data Analysis: Combination antiviral assays were performed with MT4 cells utilizing HIV-1 NL4-3 as described above. For each combination assay, five concentrations of lenacapavir were tested in all possible combinations with eight concentrations of formula 4-A. Three replicates were used to determine combination antiviral efficacy, and two replicates were used to determine combination cytotoxicity in uninfected MT4 cells. Each combination assay was performed twice unless otherwise stated.

The drug combination assay data were then analyzed using the MacSynergy II program for data analysis and statistical evaluation. Briefly, the MacSynergy II program calculates the theoretical additive interactions of the drugs based on the Bliss Independence mathematical definition of expected effects for drug-drug interactions. The Bliss Independence model is based on statistical probability and assumes that the drugs act independently to affect virus replication; this Independent Effects model is also referred to as a Dual-Site (DS) model and is used for all combination analyses reported herein.

Theoretical additive interactions were calculated from the dose response curves for each drug used individually. This calculated additive surface, which represents predicted or additive interactions, was then subtracted from the experimentally determined dose-response surface to reveal regions of non-additive activity. The resulting surface would appear on a graph as a horizontal plane at 0% inhibition above calculated if the interactions were merely additive. Any peaks above this plane-of-additivity are indicative of synergy. Similarly, any depressions below the plane-of-additivity are indicative of antagonism. The 95% confidence intervals around the experimental dose-response surface were used to evaluate the data statistically and the volume of the peaks/depressions was calculated and used to quantify the volume of synergy/antagonism produced. The volume of the peaks observed in the synergy plots (in units of concentration times concentration times percent; e.g. $\mu M^2 \%$, $nM^2 \%$, nMpM %, etc.) was calculated by the program. This peak volume was the three-dimensional counterpart of the area under a 3-dimensional dose-response surface and is a quantitative measure of synergy or antagonism. For these studies, synergy was defined as drug combinations yielding synergy volumes greater than 50. Slightly synergistic activity and highly synergistic activity were operationally defined as yielding synergy volumes of 50-100 and >100, respectively. Additive drug interactions had synergy volumes in the range of −50 to 50, while synergy volumes between −50 and −100 were considered slightly antagonistic and those <−100 were highly antagonistic.

Results: Formula 4-A demonstrated synergistic antiviral activity upon combination with lenacapavir in the two-drug combination anti-HIV studies against HIV-1 NL4-3 virus in MT4 cells (Table 3).

TABLE 3

Summary of Antiviral Efficacy Results of Formula 4-A in Combination with Lenacapavir in MT4 T Cells.

| Compound | Mean Synergy/ Antagonism Volume ($nM^2 \%$; n = 2) | Interpretation of Antiviral Combination[1] (Synergy/Antagonism) |
|---|---|---|
| Formula 4-A + lenacapavir | 162/−5.03 | Highly synergistic |
| Stavudine + Ribavirin | 0/−572 | Highly antagonistic |

[1]Synergy is defined as drug combinations yielding synergy volumes greater than 50. Slightly synergistic activity and highly synergistic activity are defined as yielding synergy volumes of 50-100 and >100, respectively. Additive drug interactions have synergy volumes in the range of −50 to 50, while synergy volumes between −50 and −100 are considered slightly antagonistic and those <−100 are highly antagonistic.

A representative example of a Mean 3-D Surface Plot of Formula 4-A and Lenacapavir Antiviral Drug Interactions in MT4 cells with HIV-1 NL-43 is shown in FIG. 1.

Example 8

Plasma Exposures Following Oral Administration of Prodrugs to Beagle Dogs

The pharmacokinetics of EFdA and prodrug formula 4-A were studied in dogs after oral administration of a 5 mg-equivalent/kg EFdA dose.

Formulations: The prodrugs were formulated as solutions at 1.65 mg/mL in 20% PEG400 aqueous solution within 0.5 hour prior to dose.

Dose Administration and Sample Collection: The in-life phase of this study was conducted at the Charles River Laboratory (CRL) at Worcester, MA in accordance with the CRL Institutional Animal Care and Use Committee (IACUC) standard animal procedures along with the IACUC guidelines that are in compliance with the Animal Welfare Act, the Guide for the Care and Use of Laboratory Animals. and was approved by the IACUA Committee. Fasted male beagle dogs (10+/−2 kg) were used for the studies. Each drug was administered as a single dose by oral gavage (5 ml/kg). The prodrug formula 4-A dose (8.25 mg/kg) was dose-equivalent to 5 mg/kg of EFdA. Plasma samples were collected at 0 (pre-dose), 30 min, 1, 2, 4, 6, 8, 12 and 24 h post-dose. Blood (approximately 0.1 to 0.2 mL) was processed immediately for plasma by centrifugation at 3,500 rpm at 5° C. for 10 min immediately after collection. Plasma samples were frozen and maintained at −70° C. until analyzed. To stabilize the prodrug at the sample collection and subsequent analysis, the following stabilizing reagents were added to the blood collection K2EDTA tubes on wet ice prior to sample collection: for each 100 mL of blood, 15 mL of premade inhibitor cocktail consists of 1 mM DFP, 100 mM dichlorvos, 100 mM 2-Hydroxyquinoline, 100 mM PCMB, 1 mM Paraoxon, 100 mM PMSF, 100 mM NaF, 30.0 mM EDTA, and 15 mM Citric Acid, 10 mL of 0.2M eserine, and 10 mL of 0.2M BNPP solutions.

Determination of EFdA and Prodrugs in plasma: Briefly, plasma (20 µL) was mixed with 100 µl acetonitrile to precipitate protein. Consistent with sample collection procedure, the same cocktail protocol was also added to stabilize the prodrug in the standard and QC samples.

Bioanalysis: A Sciex API-6500 triplequadrupole mass spectrometer coupled with a Shimadzu HPLC system (Framingham, MA 01701) was used for quantitative analysis of plasma samples. The column was a Waters HSS T3 column (2.1×50 mm, 1.8 mm). The mobile phases used were: A, 5% acetonitrile in 2 mM ammonium formate buffer; B, 95% acetonitrile in 2 mM ammonium formate buffer, pH 6.0. The flow rate was 0.6 mL/min with a total run time of 3.0 min. The HPLC gradient was initiated at 98% A/2% B for 0.20 min, followed by linear gradient increase to 25% over the next 1.40 min; the gradient was subsequently increased to 100% of mobile B over the next 1.0 min and then held for additional 0.2 min before ramping down to 2% mobile phase B within the following 0.2 min. Detection of the prodrug and EFdA were achieved using positive ion electrospray mass spectroscopic mode using unit resolution mode. Multiple reaction monitoring (MRM) modes were used to quantify both prodrug and EFdA, e.g. the MRM transition for EFdA was 294.0-153.90 Da, and the transition for prodrug 4-A was 450.0-153.9 Da. Peak areas were integrated by the Sciex program Analyst®, version 1.6.3, operating on a Windows 7 computer where concentrations were determined by a weighted (1/×2) linear regression of peak area ratios (peak area of EFdA/peak area of corresponding IS) versus the nominal concentrations of the plasma calibration standards. Calculations were performed on unrounded numbers. Overall, Analyst® determined the precision and accuracy for the calibration standards and QC samples.

Pharmacokinetic Calculations: The noncompartmental (NCA) analysis of EFdA and prodrug individual plasma concentration-time data were conducted using WinNonlin module in the Phoenix PK/PD Platform (version 8.3.0.5005, Certara Inc., Princeton, NJ 08540). Calculations were performed prior to rounding and nominal sampling times were used in the pharmacokinetic analysis. Exposures were expressed as areas under concentration curves in plasma from zero to 24 hours ($AUC_{0-24\ h}$). The AUC values were calculated using the linear trapezoidal rule.

Plasma Concentrations: The results of the PK studies are shown in Tables 3 and 4. These data establish in vivo that prodrug formula 4-A can be readily delivered orally, and can efficiently release EFdA in vivo with minimal prodrug detected in the systemic circulation. For example, prodrug formula 4-A can release significantly more EFdA in vivo than a dose-equivalent EFdA, i.e., 91%, 102%, 55%, 79%, and 200% more at 0.25, 0.5, 1, 2, and 4-hour time points (see Table 4). Further, prodrug formula 4-A can produce a higher AUC and $C_{max}$ than a dose-equivalent EFdA (see Table 4).

TABLE 4

Plasma concentration of EFdA and prodrug formula 4-A after a single oral dose to male beagle dogs.

| Prodrug formula 4-A PO (8.25 mg/kg) Time Points (hrs) | Animal ID | | | Mean | SD | % CV |
|---|---|---|---|---|---|---|
| | 2001 | 2002 | 2003 | | | |
| EFdA Concentrations (ng/mL) in Dog Plasma | | | | | | |
| 0.250 | 463 | 533 | 1040 | 679 | 315 | 46.4% |
| 0.500 | 593 | 621 | 749 | 654 | 83.2 | 12.7% |
| 1.00 | 585 | 555 | 538 | 559 | 23.8 | 4.3% |
| 2.00 | 369 | 410 | 239 | 339 | 89.3 | 26.3% |
| 4.00 | 33.4 | 45.4 | 31.9 | 36.9 | 7.40 | 20.1% |
| 6.00 | 4.93 | 5.39 | 2.45 | 4.26 | 1.58 | 37.1% |
| 8.00 | 1.30 | 1.84 | 1.76 | 1.63 | 0.291 | 17.9% |
| 12.0 | BQL | BQL | BQL | NA | NA | NA |
| 24.0 | BQL | BQL | BQL | NA | NA | NA |
| Prodrug formula 4-A Concentrations (ng/mL) in Dog Plasma | | | | | | |
| 0.250 | 1.13 | 1.63 | 1.09 | 1.28 | 0.301 | 23.5% |
| 0.500 | BQL | 1.68 | BQL | 1.68 | NA | NA |
| 1.00 | BQL | BQL | 1.43 | 1.43 | NA | NA |
| 2.00 | BQL | BQL | BQL | NA | NA | NA |
| 4.00 | BQL | BQL | BQL | NA | NA | NA |
| 6.00 | BQL | BQL | BQL | NA | NA | NA |
| 8.00 | BQL | BQL | BQL | NA | NA | NA |
| 12.0 | BQL | BQL | BQL | NA | NA | NA |
| 24.0 | BQL | BQL | BQL | NA | NA | NA |

TABLE 4-continued

Plasma concentration of EFdA and prodrug formula
4-A after a single oral dose to male beagle dogs.

EFdA Concentrations (ng/mL) in Dog Plasma

| EFdA PO (5 mg/kg) | Animal ID | | | | | |
|---|---|---|---|---|---|---|
| Time Points (hrs) | 4001 | 4002 | 4003 | Mean | SD | % CV |
| 0.250 | 456 | 333 | 276 | 355 | 92.0 | 25.9% |
| 0.500 | 391 | 299 | 280 | 323 | 59.4 | 18.4% |
| 1.00 | 369 | 353 | 361 | 361 | 8.00 | 2.2% |
| 2.00 | 211 | 212 | 143 | 189 | 39.6 | 21.0% |
| 4.00 | 12.6 | 17.9 | 6.30 | 12.3 | 5.81 | 47.2% |
| 6.00 | BQL | BQL | BQL | NA | NA | NA |
| 8.00 | BQL | BQL | BQL | NA | NA | NA |
| 12.0 | BQL | BQL | BQL | NA | NA | NA |
| 24.0 | BQL | BQL | BQL | NA | NA | NA |

BQL = below quantitation level;
NA = not applicable

TABLE 5

EFdA Exposure in Plasma from Oral Administration
of EFdA and Prodrug formula 4-A in Dogs

| Compound | Dose (mg/kg) | AUC (ng*hr/mL) | $C_{max}$ (ng/mL) |
|---|---|---|---|
| EFdA | 5 | 792 | 392 |
| Prodrug formula 4-A | 8.25 (~5 mg eq EFdA) | 1432 | 753 |

Example 9

Plasma Exposures Following Combined Administration of Example 4-A and Lenacapavir to Sprague-Dawley Rats Via Intravenous Infusion The pharmacokinetics of EFdA and prodrug formula 4-A, as well as lenacapavir were studied in rats after IV infusion administration alone or in combination at a dose of 1.0 mg/kg each.

Formulations: The prodrugs and lenacapavir were formulated alone or in combination as solutions at 1.0 mg/mL each in 20% PEG400, 10% Solutol aqueous solution within 0.5 hour prior to dose.

Dose Administration and Sample Collection: The in-life phase of this study was conducted at the WuXi Apptec (WuXi) at Shanghai, China in accordance with the WuXi Institutional Animal Care and Use Committee (IACUC) standard animal procedures along with the IACUC guidelines that are in compliance with the Animal Welfare Act, the Guide for the Care and Use of Laboratory Animals. and was approved by the IACUA Committee. Male Sprague-Dawley rats (0.262+/−0.019 kg) were used for the studies. Each drug was administered as a single dose by 30-min IV infusion (1 ml/kg) alone or in combination. Plasma samples were collected at 0 (pre-dose), 5, 10, 15 and 30 min, 1, 2, 4, 7, 12 and 24 h post-dose. Blood (approximately 0.1 mL) was processed immediately for plasma by centrifugation at 3,200 g at 4° C. for 10 min within half an hour of collection. Plasma samples were frozen and maintained at −70° C. until analyzed. To stabilize the prodrug at the sample collection and subsequent analysis, the following stabilizing reagents were added to the blood collection K2EDTA tubes on wet ice prior to sample collection: for each 100 mL of blood, 10 mL of premade inhibitor cocktail consists of 600 mM Citric Acid, 400 mM PMSF, 400 mM NaF, and 400 mM Dichlorvos.

Determination of EFdA and Prodrugs in plasma: Briefly, plasma (20 µL) was mixed with 100 µl acetonitrile to precipitate protein. Consistent with sample collection procedure, the same cocktail protocol was also added to stabilize the prodrug in the standard and QC samples.

Bioanalysis: A Sciex API-6500 Plus triplequadrupole mass spectrometer coupled with a Waters Acquity UPLC system (Framingham, MA 01701) was used for quantitative analysis of plasma samples. The column was a Waters HSS T3 column (2.1×50 mm, 1.8 micrometer). The mobile phases used were: A, 0.1% formic acid in water; B, 0.1% formic acid in acetonitrile. For the analysis of EFdA and prodrugs in plasma, the flow rate was 0.6 mL/min with a total run time of 2.0 min. The HPLC gradient was initiated at 100% A for 0.30 min, followed by linear gradient increase to 40% B over the next 0.7 min; the gradient was subsequently increased to 100% of mobile B over the next 0.7 min and then held for additional 0.2 min before ramping down to 100% mobile phase A within the following 0.1 min. Detection of the prodrug and EFdA were achieved using positive ion electrospray mass spectroscopic mode using unit resolution mode. Multiple reaction monitoring (MRM) modes were used to quantify both prodrug and EFdA, e.g. the MRM transition for EFdA was 294.0-154.2 Da, and the transition for prodrug 4-A was 449.3-164.9 Da. For the analysis of lenacapavir in plasma, the flow rate was 0.7 m/min with a total run time of 1.5 min. The HPLC gradient was initiated at 95% A/5% B for 0.50 min, followed by linear gradient increase to 10% B over the next 0.2 min; the gradient was subsequently maintained at 100% of mobile B over the next 0.7 min before ramping down to 95% mobile phase A within the following 0.1 min. Detection of lenacapavir was achieved using positive ion electrospray mass spectroscopic mode using unit resolution mode. Multiple reaction monitoring (MRM) modes were used to quantify lenacapavir, e.g. the MRM transition for lenacapavir was 968.1-869.4 Da. Peak areas were integrated by the Sciex program Analyst®, version 1.6.3, operating on a Windows 7 computer where concentrations were determined by a weighted (1/×2) linear regression of peak area ratios (peak area of EFdA/peak area of corresponding IS) versus the nominal concentrations of the plasma calibration standards. Calculations were performed on unrounded numbers. Overall, Analyst® determined the precision and accuracy for the calibration standards and QC samples.

Pharmacokinetic Calculations: The noncompartmental (NCA) analysis of EFdA and prodrug individual plasma concentration-time data were conducted using WinNonlin module in the Phoenix PK/PD Platform (version 8.3.0.5005, Certara Inc., Princeton, NJ 08540). Calculations were performed prior to rounding and nominal sampling times were used in the pharmacokinetic analysis. Exposures were expressed as areas under concentration curves in plasma from zero to 24 hours ($AUC_{0-24\ h}$). The AUC values were calculated using the linear trapezoidal rule.

Plasma Concentrations: The results of the PK studies are shown in Tables 6-13. These data establish in vivo that prodrug formula 4-A can be readily delivered orally and can efficiently release EFdA in vivo with minimal prodrug detected in the systemic circulation in the absence and presences of lenacapavir. In addition, the pharmacokinetic profile of lenacapavir was not affected by co-administration of prodrugs, e.g. formula 4-A.

TABLE 6

Plasma concentration of EFdA and prodrug formula 4-A after a single IV infusion dose to male Sprague-Dawley Rats When Dosed Alone.
EFdA Concentrations (ng/mL) in Rat Plasma When Dosed Alone

| Prodrug formula 4-A IV (1.0 mg/kg) Time Points (hrs) | R01 | R02 | R03 | R04 | Mean | SD | % CV |
|---|---|---|---|---|---|---|---|
| 0.0830 | 106 | 95.3 | 107 | 84.4 | 98.2 | ± | 10.6 |
| 0.167 | 122 | 124 | 150 | 129 | 131 | ± | 12.8 |
| 0.250 | 148 | 170 | 170 | 158 | 162 | ± | 10.6 |
| 0.500 | 122 | 189 | 162 | 208 | 170 | ± | 37.3 |
| 1.00 | 43.4 | 49.4 | 57.2 | 48.0 | 49.5 | ± | 5.74 |
| 2.00 | 9.05 | 7.76 | 10.6 | 9.02 | 9.11 | ± | 1.16 |
| 4.00 | BQL | BQL | 1.30 | 1.58 | 1.44 | ± | ND |
| 7.00 | BQL | BQL | BQL | BQL | ND | ± | ND |
| 12.0 | BQL | BQL | BQL | BQL | ND | ± | ND |
| 24.0 | BQL | BQL | BQL | BQL | ND | ± | ND |

TABLE 7

Plasma concentration of EFdA and prodrug formula 4-A after a single IV infusion dose to male Sprague-Dawley Rats When Dosed with Lenacapavir.
EFdA Concentrations (ng/mL) in Rat Plasma When Dosed with Lenacapavir

| Prodrug formula 4-A IV (1.0 mg/kg) Time Points (hrs) | R09 | R10 | R11 | R12 | Mean | SD | % CV |
|---|---|---|---|---|---|---|---|
| 0.0830 | 105 | 91.2 | 82.1 | 95.7 | 93.5 | ± | 9.53 |
| 0.167 | 154 | 115 | 116 | 119 | 126 | ± | 18.7 |
| 0.250 | 191 | 157 | 161 | 134 | 161 | ± | 23.4 |
| 0.500 | 170 | 178 | 164 | 175 | 172 | ± | 6.13 |
| 1.00 | 41.1 | 51.7 | 50.3 | 40.6 | 45.9 | ± | 5.89 |
| 2.00 | 9.00 | 11.6 | 10.0 | 9.96 | 10.1 | ± | 1.08 |
| 4.00 | 1.89 | 1.70 | 1.43 | 1.36 | 1.60 | ± | 0.245 |
| 7.00 | BQL | BQL | BQL | BQL | ND | ± | ND |
| 12.0 | BQL | BQL | BQL | BQL | ND | ± | ND |
| 24.0 | BQL | BQL | BQL | BQL | ND | ± | ND |
| 48.0 | BQL | BQL | BQL | BQL | ND | ± | ND |
| 72.0 | BQL | BQL | BQL | BQL | ND | ± | ND |

TABLE 8

Plasma Prodrug formula 4A Concentrations (ng/mL) in Rat Plasma When Dosed alone. Prodrug formula 4A Concentrations (ng/mL) in Rat Plasma When Dosed alone

| Prodrug formula 4-A IV (1.0 mg/kg) Time Points (hrs) | R01 | R02 | R03 | R04 | Mean | SD | % CV |
|---|---|---|---|---|---|---|---|
| 0.0830 | BQL | BQL | BQL | BQL | ND | ± | ND |
| 0.167 | BQL | BQL | BQL | BQL | ND | ± | ND |
| 0.250 | BQL | 2.27 | BQL | BQL | ND | ± | ND |
| 0.500 | BQL | BQL | BQL | BQL | ND | ± | ND |
| 1.00 | BQL | BQL | BQL | BQL | ND | ± | ND |
| 2.00 | BQL | BQL | BQL | BQL | ND | ± | ND |
| 4.00 | BQL | BQL | BQL | BQL | ND | ± | ND |
| 7.00 | BQL | BQL | BQL | BQL | ND | ± | ND |
| 12.0 | BQL | BQL | BQL | BQL | ND | ± | ND |
| 24.0 | BQL | BQL | BQL | BQL | ND | ± | ND |

TABLE 9

Plasma Prodrug formula 4A Concentrations (ng/mL) in Rat Plasma When Dosed with Lenacapavir. Prodrug formula 4A Concentrations (ng/mL) in Rat Plasma When Dosed with Lenacapavir

| Prodrug formula 4-A IV (1.0 mg/kg) Time Points (hrs) | R09 | R10 | R11 | R12 | Mean | SD | % CV |
|---|---|---|---|---|---|---|---|
| 0.0830 | 1.37 | 5.19 | 1.54 | 2.80 | 2.73 | ± | 1.76 |
| 0.167 | BQL | BQL | BQL | BQL | ND | ± | ND |
| 0.250 | 1.13 | BQL | 2.38 | BQL | 1.76 | ± | ND |
| 0.500 | 1.13 | BQL | BQL | BQL | ND | ± | ND |
| 1.00 | 1.06 | BQL | BQL | BQL | ND | ± | ND |
| 2.00 | BQL | BQL | BQL | BQL | ND | ± | ND |
| 4.00 | BQL | BQL | BQL | BQL | ND | ± | ND |
| 7.00 | BQL | BQL | BQL | BQL | ND | ± | ND |
| 12.0 | BQL | BQL | BQL | BQL | ND | ± | ND |
| 24.0 | BQL | BQL | BQL | BQL | ND | ± | ND |
| 48.0 | BQL | BQL | BQL | BQL | ND | ± | ND |
| 72.0 | BQL | BQL | BQL | BQL | ND | ± | ND |

TABLE 10

Plasma concentration of Lenacapavir in Rat Plasma When Dosed Alone. Lenacapavir Concentrations (ng/mL) in Rat Plasma When Dosed Alone

| Lenacapavir IV (1.0 mg/kg) Time Points (hrs) | R05 | R06 | R07 | R08 | Mean | SD | % CV |
|---|---|---|---|---|---|---|---|
| 0.0830 | 692 | 485 | 603 | 667 | 612 | ± | 92.4 |
| 0.167 | 694 | 845 | 682 | 734 | 739 | ± | 74.2 |
| 0.250 | 796 | 810 | 801 | 894 | 825 | ± | 46.2 |
| 0.500 | 980 | 612 | 580 | 984 | 789 | ± | 223 |
| 1.00 | 261 | 166 | 222 | 240 | 222 | ± | 40.7 |
| 2.00 | 181 | 104 | 149 | 164 | 150 | ± | 33.0 |
| 4.00 | 171 | 102 | 157 | 195 | 156 | ± | 39.4 |
| 7.00 | 185 | 84.6 | 141 | 142 | 138 | ± | 41.2 |
| 12.0 | 145 | 79.4 | 106 | 139 | 117 | ± | 30.6 |
| 24.0 | 141 | 123 | 141 | 139 | 136 | ± | 8.72 |
| 48.0 | 107 | 69.4 | 68.7 | 79.7 | 81.2 | ± | 17.9 |
| 72.0 | 51.3 | 59.7 | 57.2 | 110 | 69.6 | ± | 27.2 |

TABLE 11

Plasma concentration of Lenacapavir in Rat Plasma When Dosed with Prodrug formula 4-A. Lenacapavir Concentrations (ng/mL) in Rat Plasma When Dosed with Prodrug formula 4-A

| Lenacapavir IV (1.0 mg/kg) Time Points (hrs) | R09 | R10 | R11 | R12 | Mean | SD | % CV |
|---|---|---|---|---|---|---|---|
| 0.0830 | 488 | 460 | 391 | 314 | 413 | ± | 77.7 |
| 0.167 | 546 | 479 | 589 | 415 | 507 | ± | 76.4 |
| 0.250 | 696 | 623 | 664 | 375 | 590 | ± | 146 |
| 0.500 | 774 | 643 | 714 | 448 | 645 | ± | 142 |
| 1.00 | 201 | 170 | 170 | 107 | 162 | ± | 39.5 |
| 2.00 | 174 | 135 | 105 | 94.7 | 127 | ± | 35.6 |
| 4.00 | 98.9 | 93.1 | 101 | 80.9 | 93.5 | ± | 9.02 |
| 7.00 | 140 | 101 | 72.3 | 58.8 | 93.0 | ± | 35.9 |
| 12.0 | 139 | 137 | 158 | 78.6 | 128 | ± | 34.4 |
| 24.0 | 129 | 164 | 176 | 62.5 | 133 | ± | 51.0 |
| 48.0 | 66.2 | 64.1 | 113 | 59.5 | 75.7 | ± | 25.0 |
| 72.0 | 40.1 | 97.8 | 97.2 | 98.0 | 83.3 | ± | 28.8 |

BQL = below quantitation level;
ND = not determined

TABLE 12

EFdA Exposure in Plasma from IV Administration of Prodrug formula 4-A alone or in combination with Lenacapavir in Rats

| Dosing Method | Dose (mg/kg) | AUC (ng*hr/mL) | $C_{max}$ (ng/mL) |
|---|---|---|---|
| Alone | 1 | 147 | 179 |
| In combination with lenacapavir | 1 | 149 | 177 |

TABLE 13

Lenacapavir Exposure in Plasma from IV Administration of Lenacapavir alone or in combination with Prodrug formula 4-A in Rats

| Dosing Method | Dose (mg/kg) | AUC (ng*hr/mL) | $C_{max}$ (ng/mL) |
|---|---|---|---|
| Alone | 1 | 7976 | 903 |
| In combination with Prodrug formula 4-A | 1 | 7483 | 645 |

INCORPORATION BY REFERENCE

All publications, patents, and patent applications mentioned in this specification are herein incorporated by reference to the same extent as if each individual publication, patent, or patent application was specifically and individually indicated to be incorporated by reference.

The invention claimed is:

1. A method of treating or preventing an HIV infection, comprising administering to a subject in need thereof an effective amount of:

(a) a capsid inhibitor; and (b) an adenosine derivative, wherein the adenosine derivative is a compound of formula (1):

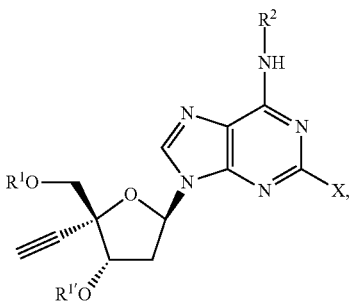

(1)

or a pharmaceutically acceptable salt thereof,
wherein:
$R^1$ is H, -$L^1$-$R^5$, or —Z-$L^4$-$R^5$;
$R^{1'}$ is H or -$L^1$-$R^5$;
$R^2$ is H or —$R^5$, provided that least one of $R^1$ and $R^2$ is not H;
$R^5$ is:

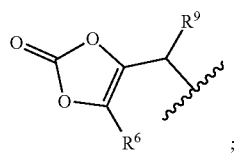

;

$R^6$ is H, C1-C10 alkyl, C2-C10 alkenyl, C3-C10 cycloalkyl, 3- to 10-membered heterocycloalkyl, aryl, or heteroaryl;
-$L^1$-$R^5$ is —(C1-C10 alkylene)-N($R^7$)—$R^5$, —(C1-C10 alkylene)-O—$R^5$, —(C1-C10 alkylene)-S—$R^5$, —(C2-C10 alkenylene)-N($R^7$)—$R^5$, —(C2-C10 alkenylene)-O—$R^5$, —(C2-C10 alkenylene)-S—$R^5$, —C(O)O—$R^5$, —C(O)O-$L^2$-N($R^7$)—$R^5$, —C(O)O-$L^2$-O—$R^5$, —C(O)O-$L^2$-S—$R^5$, —C(O)O-$L^2$-C(O)O—$R^5$, —C(O)O-$L^2$-C(O)N($R^7$)—$R^5$, —C(O)O-$L^2$-C(O)N($R^7$)-$L^3$-N($R^7$)—$R^5$, —C(O)O-$L^2$-C(O)N($R^7$)-$L^3$-O—$R^5$, —C(O)O-$L^2$-C(O)N($R^7$)-$L^3$-S—$R^5$, —C(O)N($R^7$)—$R^5$, —C(O)N($R^7$)-$L^2$-N($R^7$)—$R^5$, —C(O)N($R^7$)-$L^2$-O—$R^5$, —C(O)N($R^7$)-$L^2$-S—$R^5$, —C(O)N($R^7$)-$L^2$-C(O)O—$R^5$, —C(O)N($R^7$)-$L^2$-C(O)N($R^8$)—$R^5$—, —C(O)N($R^7$)-$L^2$-C(O)N($R^8$)-$L^3$-N($R^7$)—$R^5$, —C(O)O-$L^2$-N($R^7$)C(O)O—$R^5$, —C(O)N($R^8$)-$L^2$-N($R^7$)C(O)O—$R^5$, —C(O)O-$L^2$-N($R^7$)C(O)N($R^8$)—$R^5$, —C(O)N($R^7$)-$L^2$-N($R^7$)C(O)N($R^8$)—$R^5$, —C(O)N($R^7$)-$L^2$-C(O)N($R^8$)-$L^3$-O—$R^5$ or —C(O)N($R^7$)-$L^2$-C(O)N($R^8$)-$L^3$-S—$R^5$;
—Z— is —C(O)—, —C(O)O—, or —C(O)N($R^7$)—;
-$L^4$-$R^5$ is —(C1-C10 alkylene)-N($R^7$)—$R^5$, —(C1-C10 alkylene)-O—$R^5$, —(C1-C10 alkylene)-S—$R^5$, —(C2-C10 alkenylene)-N($R^7$)—$R^5$, —(C2-C10 alkenylene)-O—$R^5$, —(C2-C10 alkenylene)-S—$R^5$ or —(C3 alkylene)-N($R^7$)—C(O)—$R^5$;
$R^7$ and $R^8$ each is independently H, C1-C10 alkyl, or C2-C10 alkenyl;
$R^9$ is independently H, —F, C1-C10 alkyl, or C2-C10 alkenyl;
$L^2$ and $L^3$ each is divalent —(C1-C10 alkylene)- or —(C2-C10 alkenylene)-; and
X is a halogen atom.

2. The method of claim 1, wherein $R^1$ is -$L^1$-$R^5$.
3. The method of claim 1, wherein $R^{1'}$ is H.
4. The method of claim 1, wherein -$L^1$-$R^5$ is selected from the group consisting of C(O)O—$R^5$, —C(O)O-$L^2$-N($R^7$)—$R^5$, —C(O)O-$L^2$-O—$R^5$, —C(O)O-$L^2$-C(O)O—$R^5$, —C(O)O-$L^2$-C(O)N($R^7$)—$R^5$, —C(O)N($R^7$)-$L^2$-N($R^7$)—$R^5$, —C(O)N($R^7$)-$L^2$-O—$R^5$, —C(O)O-$L^2$-N($R^7$)C(O)O—$R^5$, —C(O)N($R^8$)-$L^2$-N($R^7$)C(O)O—$R^5$, —C(O)O-$L^2$-N($R^7$)C(O)N($R^8$)—$R^5$, —C(O)N($R^7$)-$L^2$-N($R^7$)C(O)N($R^8$)—$R^5$, —C(O)N($R^7$)-$L^2$-C(O)O—$R^5$, and —C(O)N($R^7$)-$L^2$-C(O)N($R^8$)—$R^5$—.

5. The method of claim 4, wherein -$L^1$-$R^5$ is —C(O)O—$R^5$ or —C(O)N($R^7$)-$L^2$-N($R^7$)—$R^5$.

6. The method of claim 4, wherein -$L^1$-$R^5$ is —C(O)O—$R^5$.

7. The method of claim 1, wherein $R^2$ is H.

8. The method of claim 1, wherein -$L^4$-$R^5$ is —(C1-C10 alkylene)-N($R^7$)—$R^5$ or —(C3 alkylene)-N($R^7$)—C(O)—$R^5$.

9. The method of claim 1, wherein —Z— is —C(O)— or —C(O)N($R^7$)—.

10. The method of claim 1, wherein $R^6$ is C1-C5 alkyl.

11. The method of claim 10, wherein $R^6$ is methyl.

12. The method of claim 1, wherein $R^7$ and $R^8$ each is independently H or C1-C5 alkyl.

13. The method of claim 12, wherein $R^7$ and $R^8$ each is independently H or methyl.

14. The method of claim 1, wherein $R^9$ is H or Me.

15. The method of claim 14, wherein $R^9$ is H.

16. The method of claim 1, wherein the adenosine derivative is a compound having the structure:

formula (4-A)

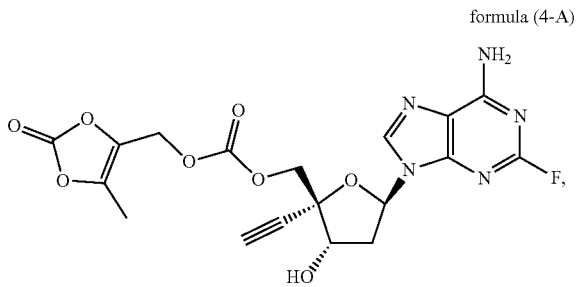

formula (4-C)

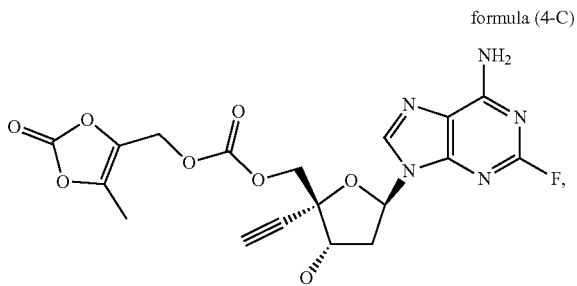

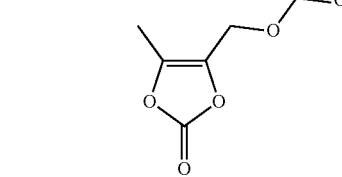

-continued formula (6-A)

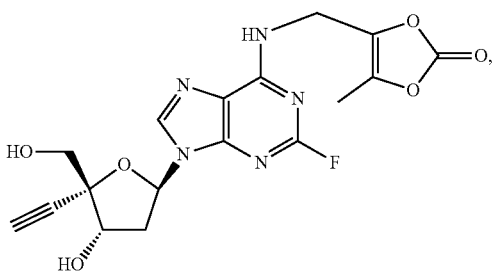

or a pharmaceutically acceptable salt thereof.

17. The method of claim 1, wherein the adenosine derivative or pharmaceutically acceptable salt thereof is administered orally.

18. The method of claim 1, wherein the capsid (CA) inhibitor and the adenosine derivative, or pharmaceutically acceptable salt thereof are administered to the subject simultaneously or sequentially.

19. The method of claim 18, wherein the CA inhibitor and the adenosine derivative or pharmaceutically acceptable salt thereof are administered to the subject sequentially within a time period in a range of from 0.1 minute to 72 hours.

20. The method of claim 1, wherein the CA inhibitor and the adenosine derivative or pharmaceutically acceptable salt thereof are administered to the subject once every day to once every 12 months.

21. The method of claim 20, wherein the CA inhibitor and the adenosine derivative or pharmaceutically acceptable salt thereof are administered to the subject once every 6 months.

22. The method of claim 20, wherein the CA inhibitor and the adenosine derivative or pharmaceutically acceptable salt thereof are administered to the subject once every one to 8 weeks.

23. The method of claim 20, wherein at least one of the CA inhibitor and the adenosine derivative or pharmaceutically acceptable salt thereof is administered to the subject once every month.

24. The method of claim 1, wherein the CA inhibitor is a compound having the structure:

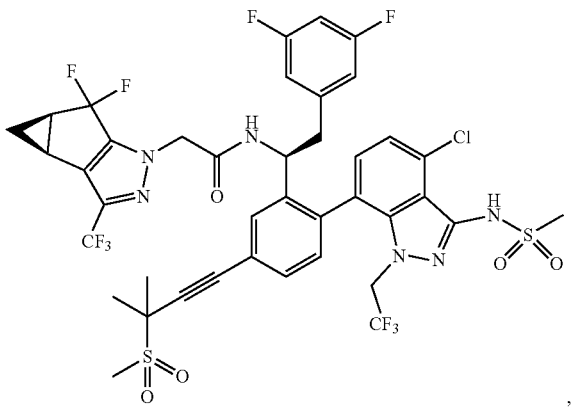 [SMILES: CC(C)(C#Cc1ccc(-c2ccc(Cl)c3c(NS(C)(=O)=O)nn(CC(F)(F)F)c23)c([C@H](Cc2cc(F)cc(F)c2)NC(=O)Cn2nc(C(F)(F)F)c3c2C(F)(F)[C@@H]2C[C@H]32)n1)S(C)(=O)=O]

or a pharmaceutically acceptable salt, tautomer, or solvate thereof.

25. The method of claim 24, wherein the effective dosage of the CA inhibitor is a single dosage in a range of from 100 mg to 2000 mg administered every 6 months.

26. The method of claim 24, wherein the effective dosage of the CA inhibitor is in a range of from 200 mg to 1200 mg administered every 1 to 7 days.

27. The method of claim 24, wherein the effective dosage of the CA inhibitor is in a range of from 300 mg to 1200 mg administered once every week (QW) and the effective dosage of the adenosine derivative or pharmaceutically acceptable salt or solvate thereof is a range of from 100 mg to 2000 mg administered once every week (QW) to once every 8 weeks (Q8W).

28. The method of claim 24, wherein the effective dosage of the CA inhibitor is in a range of from 900 mg to 2000 mg administered once every month (QM) and the effective dosage of the adenosine derivative or pharmaceutically acceptable salt thereof is in a range of from 100 mg to 2000 mg administered once every week (QW) to once every 8 weeks (Q8W).

29. The method of claim 1, wherein the HIV infection is caused by wild-type HIV-1, NRTI-resistant HIV-1, HIV-2, HIV having M184V mutations, HIV having K65R, or multidrug resistant HIV.

30. The method of claim 1, wherein the subject is a person having highly treatment-experienced HIV, a person who has been heavily treated and HIV multidrug-resistant, a person who is HIV-positive, a person who is undertaking pre-exposure prophylaxis (PrEP) by taking one or more anti-HIV medications, a woman at risk of HIV, or a man at risk of HIV.

31. A pharmaceutical composition, comprising an effective amount of:
(a) a capsid (CA) inhibitor; and
(b) an adenosine derivative or a pharmaceutically acceptable salt thereof,
wherein the adenosine derivative is a compound having a structure of formula (1):

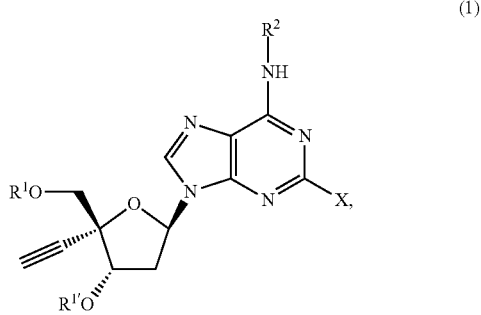

wherein,
$R^1$ is H, $-L^1-R^5$, or $-Z-L^4-R^5$;
$R^{1'}$ is H or $-L^1-R^5$;
$R^2$ is H or $-R^5$, provided that at least one of $R^1$ and $R^2$ is not H;
$R^5$ is:

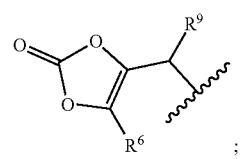

R$^6$ is H, C1-C10 alkyl, C2-C10 alkenyl, C3-C10 cycloalkyl, 3- to 10-membered heterocycloalkyl, aryl, or heteroaryl;

-L$^1$-R$^5$ is —(C1-C10 alkylene)-N(R$^7$)—R$^5$, —(C1-C10 alkylene)-O—R, —(C1-C10 alkylene)-S—R$^5$, —(C2-C10 alkenylene)-N(R$^7$)—RN, —(C2-C10 alkenylene)-O—R$^5$, —(C2-C10 alkenylene)-S—R$^5$, —C(O)O—R$^5$, —C(O)O-L$^2$-N(R$^7$)—R$^5$, —C(O)O-L$^2$-O—R$^5$, —C(O)O-L$^2$-S—R$^5$, —C(O)O-L$^2$-C(O)O—R$^5$, —C(O)O-L$^2$-C(O)N(R$^7$)—R$^5$, —C(O)O-L$^2$-C(O)N(R$^7$)-L$^3$-N(R$^7$)—R$^5$, —C(O)O-L$^2$-C(O)N(R$^7$)-L$^3$-O—R$^5$, —C(O)O-L$^2$-C(O)N(R$^7$)-L$^3$-S—R$^5$, —C(O)N(R$^7$)—R$^5$, —C(O)N(R$^7$)-L$^2$-N(R$^7$)—R$^5$, —C(O)N(R$^7$)-L$^2$-O—R$^5$, —C(O)N(R$^7$)-L$^2$-S—R$^5$, —C(O)N(R$^7$)-L$^2$-C(O)O—R$^5$, —C(O)N(R$^7$)-L$^2$-C(O)N(R$^8$)—R$^5$—, —C(O)N(R$^7$)-L$^2$-C(O)N(R$^8$)-L$^3$-N(R$^7$)—R$^5$, —C(O)O-L$^2$-N(R$^7$)C(O)O—R$^5$, —C(O)N(R$^8$)-L$^2$-N(R$^7$)C(O)O—R$^5$, —C(O)O-L$^2$-N(R$^7$)C(O)N(R$^8$)—R$^5$, —C(O)N(R$^7$)-L$^2$-N(R$^7$)C(O)N(R$^8$)—R$^5$, —C(O)N(R$^7$)-L$^2$-C(O)N(R$^8$)-L$^3$-O—R$^5$ or —C(O)N(R$^7$)-L$^2$-C(O)N(R$^8$)-L$^3$-S—R$^5$;

—Z— is —C(O)—, —C(O)O—, or —C(O)N(R$^7$)—;

-L$^4$-R$^5$ is —(C1-C10 alkylene)-N(R$^7$)—R$^5$, —(C1-C10 alkylene)-O—R$^5$, —(C1-C10 alkyl)-S—R$^5$, —(C2-C10 alkenylene)-N(R$^7$)—R$^5$, —(C2-C10 alkenylene)-O—R$^5$ or —(C2-C10 alkenylene)-S—R$^5$;

R$^7$ and R$^8$ each is independently H, C1-C10 alkyl, or C2-C10 alkenyl;

R$^9$ is independently H, —F, C1-C10 alkyl, or C2-C10 alkenyl;

L$^2$ and L$^3$ each is —(C1-C10 alkylene)-, or —(C2-C10 alkenylene)-; and

X is a halogen atom.

32. The method of claim 1, wherein the capsid inhibitor is administered orally.

33. The method of claim 1, wherein the capsid inhibitor is administered parentally.

34. The method of claim 33, wherein the parental administration is by intramuscular and/or subcutaneous injection.

35. The method of claim 1, wherein the adenosine derivative or pharmaceutically acceptable salt thereof is administered orally.

36. The method of claim 1, wherein the adenosine derivative or pharmaceutically acceptable salt thereof is administered parentally.

37. The method of claim 36, wherein the parental administration is by intramuscular and/or subcutaneous injection.

38. The method of claim 1, wherein the adenosine derivative is a compound having the structure:

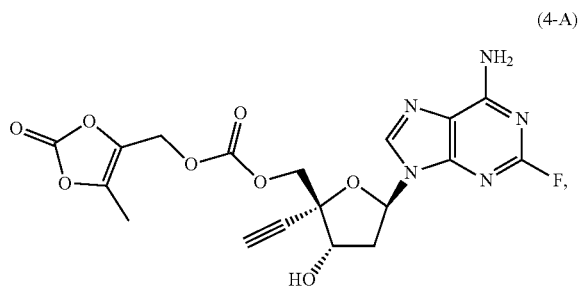 [SMILES: C#C[C@]1(COC(=O)OCc2oc(=O)oc2C)O[C@@H](n2cnc3c(N)nc(F)nc32)C[C@@H]1O]

(4-A)

or a pharmaceutically acceptable salt thereof.

39. The method of claim 1, wherein X is F.

40. The method of claim 1, wherein R$^5$ is

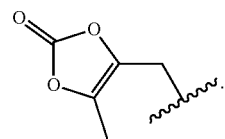 [SMILES: *Cc1oc(=O)oc1C]

41. The method of claim 1, wherein -L$^1$-R$^5$ is —C(O)O—R$^5$ or —C(O)N(R$^7$)-L$^2$-N(R$^7$)—R$^5$; -L$^4$-R$^5$ is —(C1-C10 alkylene)-N(R$^7$)—R$^5$ or —(C3 alkylene)-N(R$^7$)—C(O)—R$^5$; and R$^5$ is

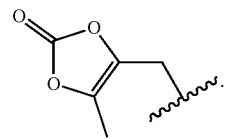

* * * * *

UNITED STATES PATENT AND TRADEMARK OFFICE
CERTIFICATE OF CORRECTION

PATENT NO. : 11,890,297 B2
APPLICATION NO. : 17/583815
DATED : February 6, 2024
INVENTOR(S) : Lianhong Xu et al.

It is certified that error appears in the above-identified patent and that said Letters Patent is hereby corrected as shown below:

In the Claims

At Column 105, Claim 1, Line 20, replace "that least one" with "that at least one".

At Column 106, Claim 4, Line 2, replace "C(O)O—$R^5$" with "—C(O)O—$R^5$".

Signed and Sealed this
Twelfth Day of March, 2024

Katherine Kelly Vidal
*Director of the United States Patent and Trademark Office*